(12) United States Patent
Lazarus et al.

(10) Patent No.: US 9,155,612 B2
(45) Date of Patent: Oct. 13, 2015

(54) COMPOSITE STENT GRAFTS FOR IN SITU ASSEMBLY AND RELATED METHODS

(75) Inventors: Harrison M. Lazarus, Salt Lake City, UT (US); Troy J. Orr, Draper, UT (US)

(73) Assignee: Intermountain Invention Management, LLC, Salt Lake City, UT (US)

( * ) Notice: Subject to any disclaimer, the term of this patent is extended or adjusted under 35 U.S.C. 154(b) by 249 days.

(21) Appl. No.: 13/347,561

(22) Filed: Jan. 10, 2012

(65) Prior Publication Data

US 2012/0179235 A1 Jul. 12, 2012

Related U.S. Application Data

(60) Provisional application No. 61/431,183, filed on Jan. 10, 2011.

(51) Int. Cl.
| | |
|---|---|
| *A61F 2/07* | (2013.01) |
| *A61F 2/954* | (2013.01) |
| *A61F 2/958* | (2013.01) |
| *A61F 2/06* | (2013.01) |
| *A61F 2/89* | (2013.01) |
| *A61F 2/848* | (2013.01) |
| *A61F 2/95* | (2013.01) |

(52) U.S. Cl.
CPC . *A61F 2/07* (2013.01); *A61F 2/954* (2013.01); *A61F 2/958* (2013.01); *A61F 2/848* (2013.01); *A61F 2/89* (2013.01); *A61F 2002/061* (2013.01); *A61F 2002/065* (2013.01); *A61F 2002/067* (2013.01); *A61F 2002/075* (2013.01); *A61F 2002/8486* (2013.01); *A61F 2002/9534* (2013.01); *A61F 2220/0016* (2013.01); *A61F 2220/0025* (2013.01); *A61F 2220/0075* (2013.01); *A61F 2230/0054* (2013.01); *A61F 2250/006* (2013.01); *A61F 2250/0037* (2013.01)

(58) Field of Classification Search
CPC ................... A61F 2002/065; A61F 2002/067
USPC .............................. 623/1.13, 1.16, 1.35, 1.36
See application file for complete search history.

(56) References Cited

U.S. PATENT DOCUMENTS

| | | | |
|---|---|---|---|
| 4,195,623 A | | 4/1980 | Zeff et al. |
| 5,275,580 A | | 1/1994 | Yamazaki |
| 5,387,235 A | | 2/1995 | Chuter |
| 5,405,383 A | | 4/1995 | Barr |
| 5,489,295 A | * | 2/1996 | Piplani et al. ................ 623/1.35 |
| 5,632,763 A | | 5/1997 | Glastra |
| 5,662,675 A | | 9/1997 | Polanskyj Stockert et al. |
| 5,676,697 A | | 10/1997 | McDonald |
| 6,030,414 A | * | 2/2000 | Taheri ............................. 623/1.1 |
| 6,036,723 A | * | 3/2000 | Anidjar et al. ............... 623/1.13 |
| 6,093,203 A | * | 7/2000 | Uflacker ..................... 623/1.12 |

(Continued)

FOREIGN PATENT DOCUMENTS

| | | |
|---|---|---|
| EP | 1135082 A1 | 12/2000 |
| WO | WO 9746175 A1 | 12/1997 |

(Continued)

*Primary Examiner* — Thomas J Sweet
*Assistant Examiner* — Cheryl Miller
(74) *Attorney, Agent, or Firm* — Stoel Rives LLP

(57) ABSTRACT

Composite stent grafts can include separate components that are capable of being repositioned relative to each other in situ. In some examples, a stent and a graft that are attached to each other in an insertion package do not overlap each other. The graft and stent are moved relative to each other in situ.

13 Claims, 48 Drawing Sheets

(56) References Cited

U.S. PATENT DOCUMENTS

| | | |
|---|---|---|
| 6,099,558 A | 8/2000 | White et al. |
| 6,136,025 A | 10/2000 | Barbut et al. |
| 6,162,246 A | 12/2000 | Barone |
| 6,344,056 B1* | 2/2002 | Dehdashtian ............... 623/1.35 |
| 6,454,796 B1* | 9/2002 | Barkman et al. ............ 623/1.35 |
| 6,475,166 B1* | 11/2002 | Escano ....................... 600/585 |
| 6,773,453 B2* | 8/2004 | Ravenscroft ................ 623/1.13 |
| 6,953,475 B2 | 10/2005 | Shaolian et al. |
| 6,986,786 B1 | 1/2006 | Smith |
| 7,105,017 B2 | 9/2006 | Kerr |
| 7,220,274 B1* | 5/2007 | Quinn .......................... 623/1.13 |
| 7,481,836 B2* | 1/2009 | Greenan ...................... 623/1.23 |
| 7,520,894 B2 | 4/2009 | Pavcnik et al. |
| 7,708,771 B2* | 5/2010 | Chuter et al. ................ 623/1.13 |
| 8,211,166 B2* | 7/2012 | Chuter et al. ................ 623/1.35 |
| 8,216,298 B2* | 7/2012 | Wright et al. ............... 623/1.35 |
| 8,257,423 B2* | 9/2012 | Kerr ............................ 623/1.13 |
| 8,628,567 B1* | 1/2014 | Chuter et al. ................ 623/1.35 |
| 2001/0020184 A1 | 9/2001 | Dehdashtian et al. |
| 2002/0198585 A1* | 12/2002 | Wisselink ................... 623/1.11 |
| 2003/0130720 A1 | 7/2003 | DePalma et al. |
| 2003/0199967 A1 | 10/2003 | Hartley et al. |
| 2003/0229389 A1* | 12/2003 | Escano ........................ 623/1.13 |
| 2005/0004654 A1* | 1/2005 | Khosravi et al. ............ 623/1.13 |
| 2005/0010277 A1 | 1/2005 | Chuter |
| 2005/0131516 A1* | 6/2005 | Greenhalgh ................. 623/1.13 |
| 2005/0228476 A1* | 10/2005 | DiMatteo et al. ........... 623/1.11 |
| 2005/0228484 A1 | 10/2005 | Stephens et al. |
| 2005/0288765 A1* | 12/2005 | Taheri .......................... 623/1.12 |
| 2006/0025846 A1* | 2/2006 | Feller et al. ................. 623/1.13 |
| 2006/0161245 A1 | 7/2006 | Rakos et al. |
| 2006/0259125 A1 | 11/2006 | Peacock, III |
| 2007/0027531 A1* | 2/2007 | DiMatteo et al. ........... 623/1.42 |
| 2007/0032852 A1* | 2/2007 | Machek et al. .............. 623/1.13 |
| 2007/0055363 A1* | 3/2007 | Chuter et al. ................ 623/1.35 |
| 2007/0106368 A1* | 5/2007 | Vonderwalde ............... 623/1.13 |
| 2009/0043371 A1* | 2/2009 | Fearnot ........................ 623/1.13 |
| 2009/0177265 A1* | 7/2009 | Dierking et al. ............. 623/1.13 |
| 2009/0228020 A1 | 9/2009 | Wallace et al. |
| 2009/0264821 A1* | 10/2009 | Mafi et al. ................. 604/103.01 |
| 2010/0292775 A1 | 11/2010 | Kerr |
| 2010/0318179 A1* | 12/2010 | Feinstein ..................... 623/1.15 |
| 2011/0040367 A1* | 2/2011 | Vinluan ....................... 623/1.13 |
| 2011/0251664 A1* | 10/2011 | Acosta De Acevedo .... 623/1.11 |
| 2013/0304188 A1* | 11/2013 | Schreck ....................... 623/1.12 |

FOREIGN PATENT DOCUMENTS

| | | |
|---|---|---|
| WO | WO 9853761 A1 | 12/1998 |
| WO | WO 2009046372 A2 | 4/2009 |

* cited by examiner

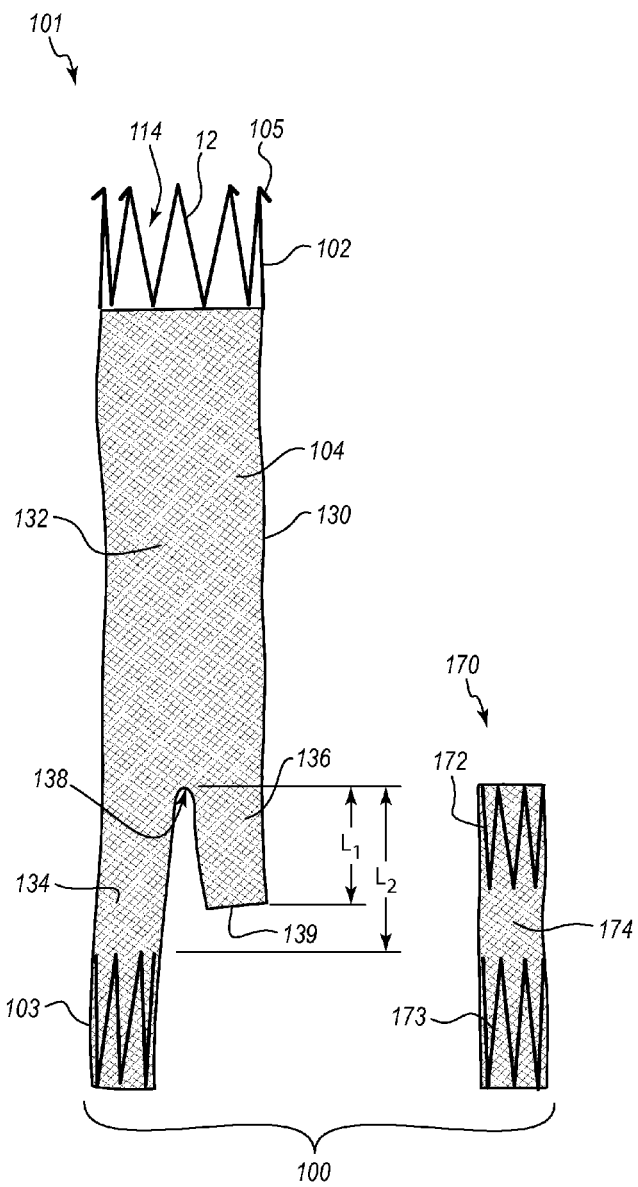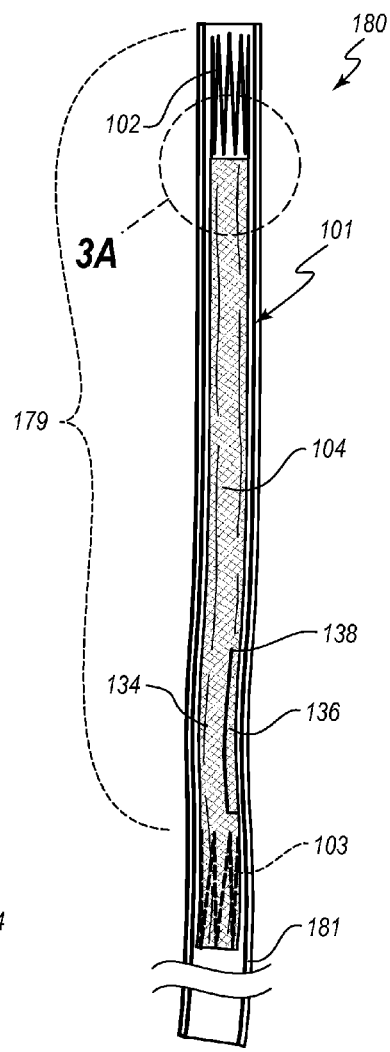
FIG. 2
FIG. 3

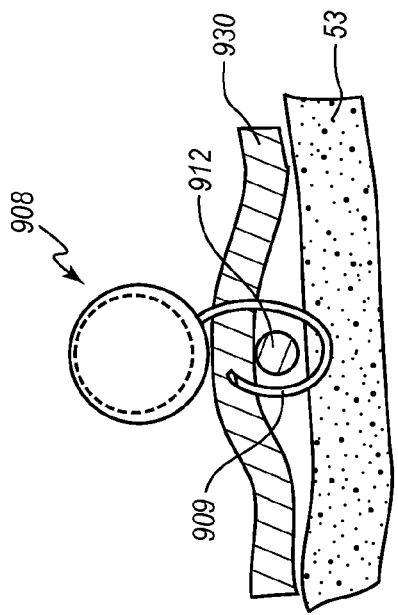
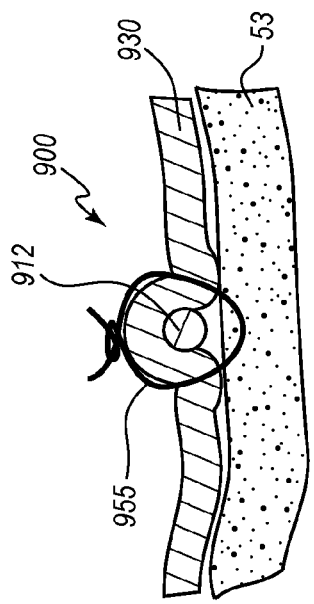
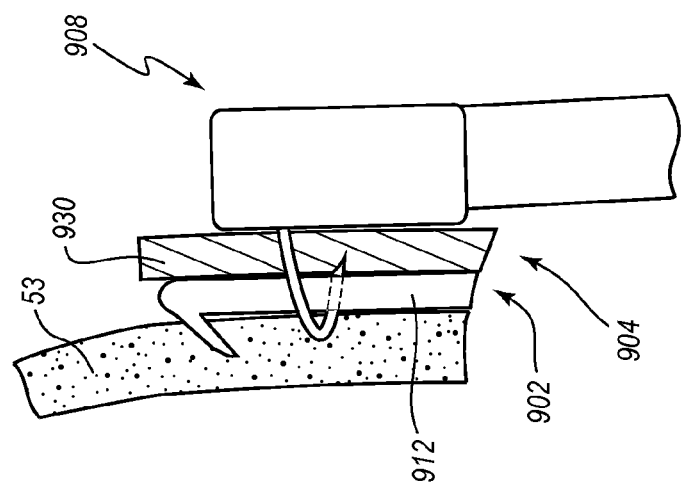
FIG. 42B
FIG. 43
FIG. 42A

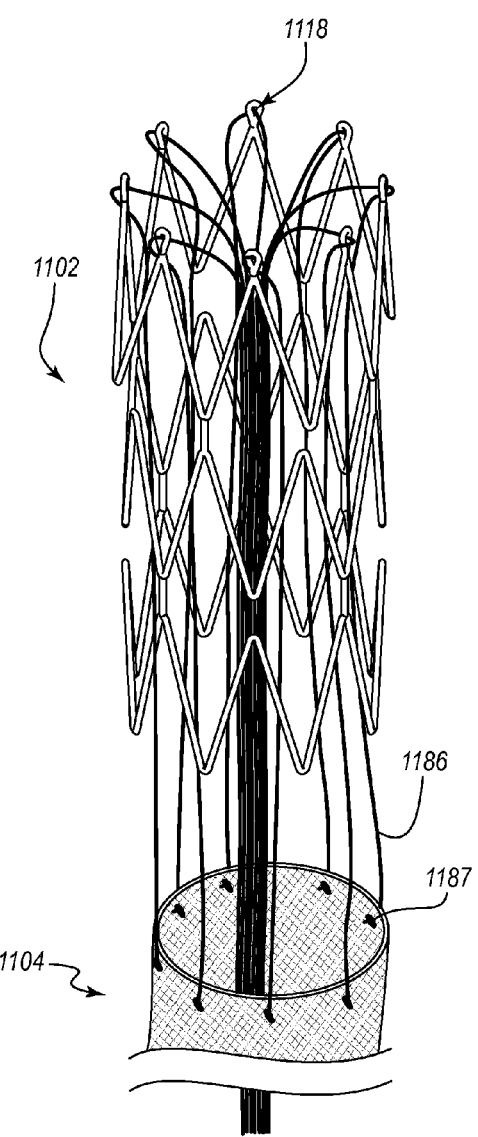
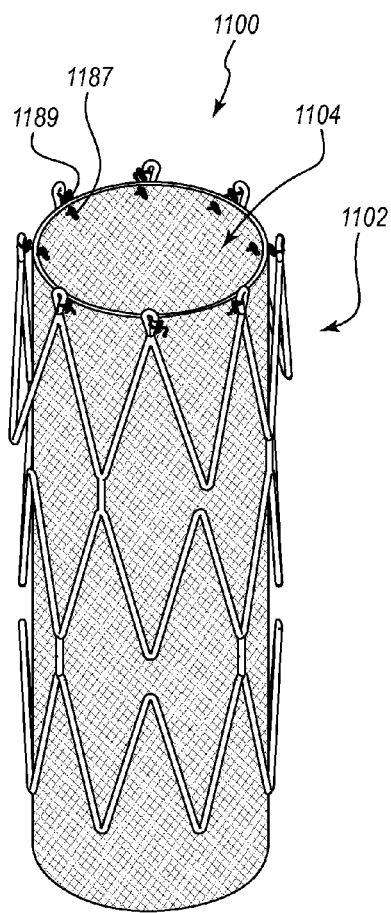
FIG. 45A
FIG. 45B

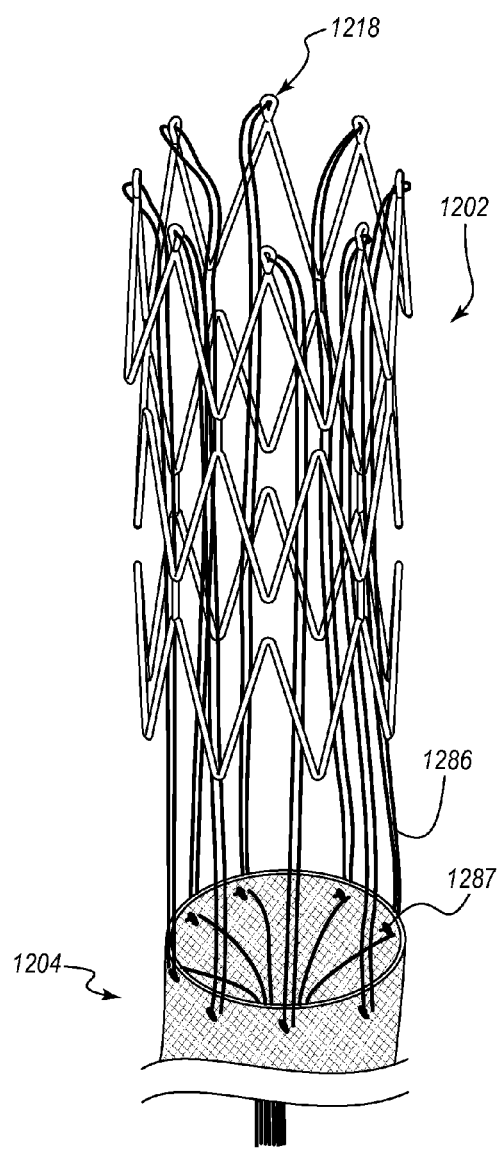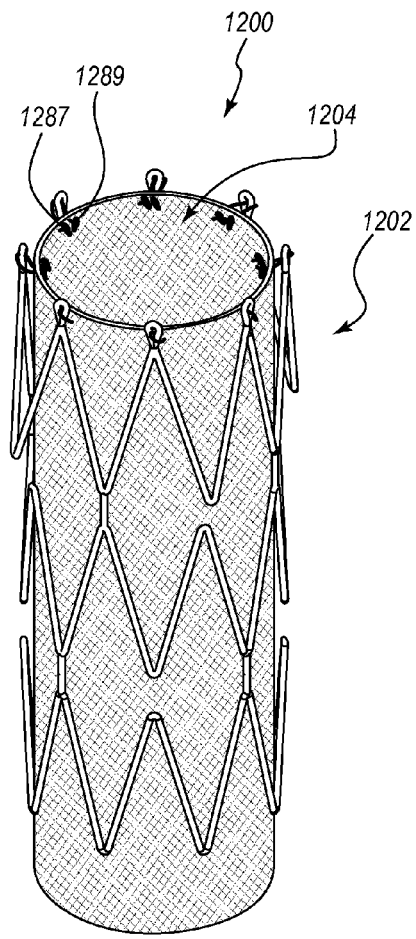
FIG. 46A
FIG. 46B

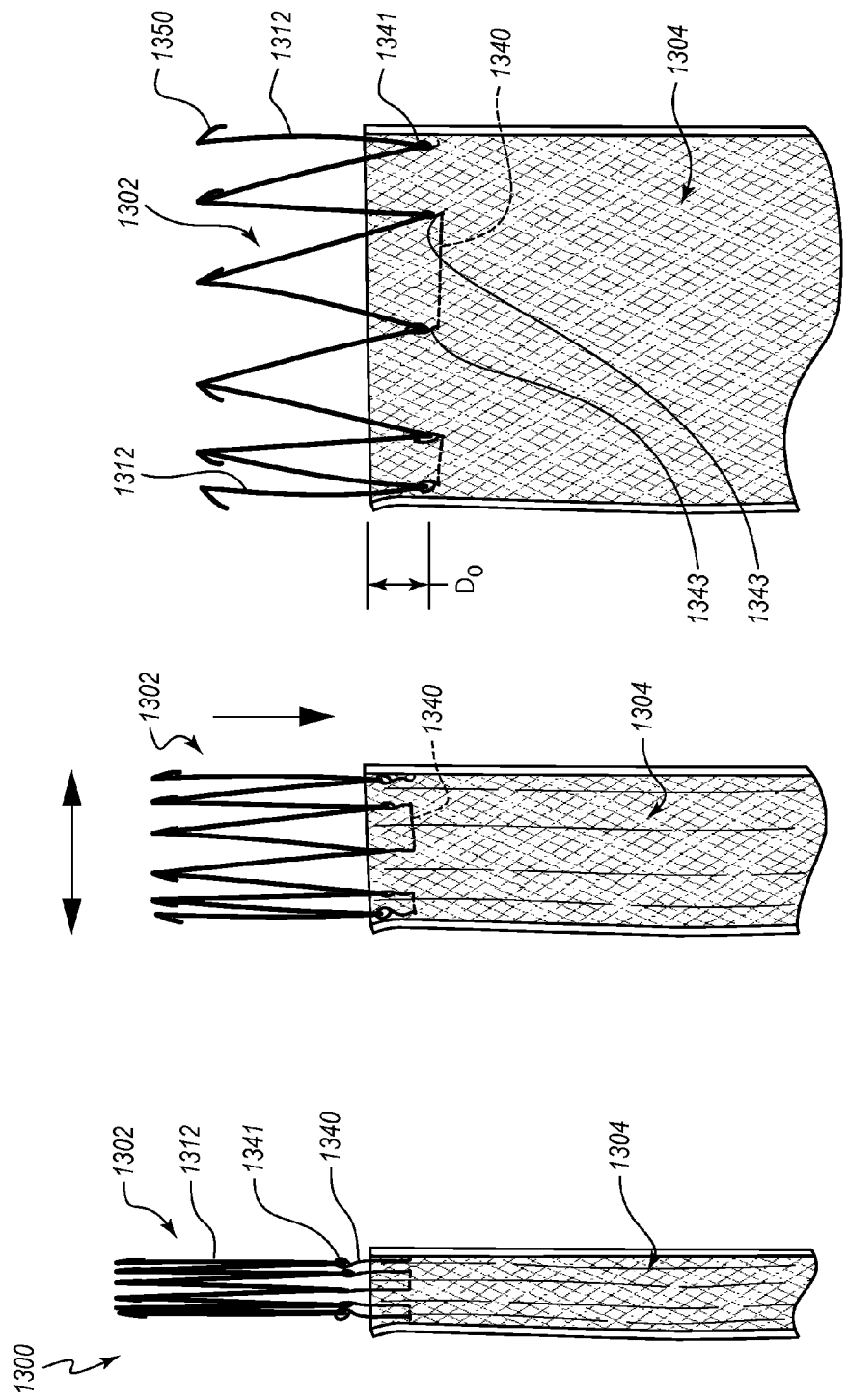

COMPOSITE STENT GRAFTS FOR IN SITU ASSEMBLY AND RELATED METHODS

CROSS-REFERENCE TO RELATED APPLICATIONS

This application claims the benefit under 35 U.S.C. §119 (e) of U.S. Provisional Patent Application No. 61/431,183, titled COMPOSITE STENT GRAFTS FOR IN SITU ASSEMBLY AND RELATED METHODS, which was filed on Jan. 10, 2011, the entire contents of which are hereby incorporated by reference herein.

TECHNICAL FIELD

The present disclosure relates to endovascular stent grafts and methods for their placement within a patient.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 2 is an elevation view of an embodiment of a stent graft assembly configured for implantation in the vasculature of a patient;

FIG. 3 is a cross-sectional view of a portion of the stent graft assembly of FIG. 2 in a packaged state;

FIG. 42A is a partial cross-sectional front view of a stage of an illustrative procedure for implanting another embodiment of a stent graft assembly;

FIG. 42B is a partial cross-sectional top view of the stage of the procedure illustrated in FIG. 42A;

FIG. 43 is a partial cross-sectional top view of another stage of the procedure of FIGS. 42A and 42B;

FIGS. 45A-45B are perspective views of various stages of an illustrative procedure for implanting another embodiment of a stent graft assembly;

FIGS. 46A-46B are perspective views of various stages of an illustrative procedure for implanting another embodiment of a stent graft assembly;

FIGS. 48A-48C are partial cross-sectional views of various stages of the deployment of the stent graft assembly of FIG. 47.

DETAILED DESCRIPTION

Figure 1:
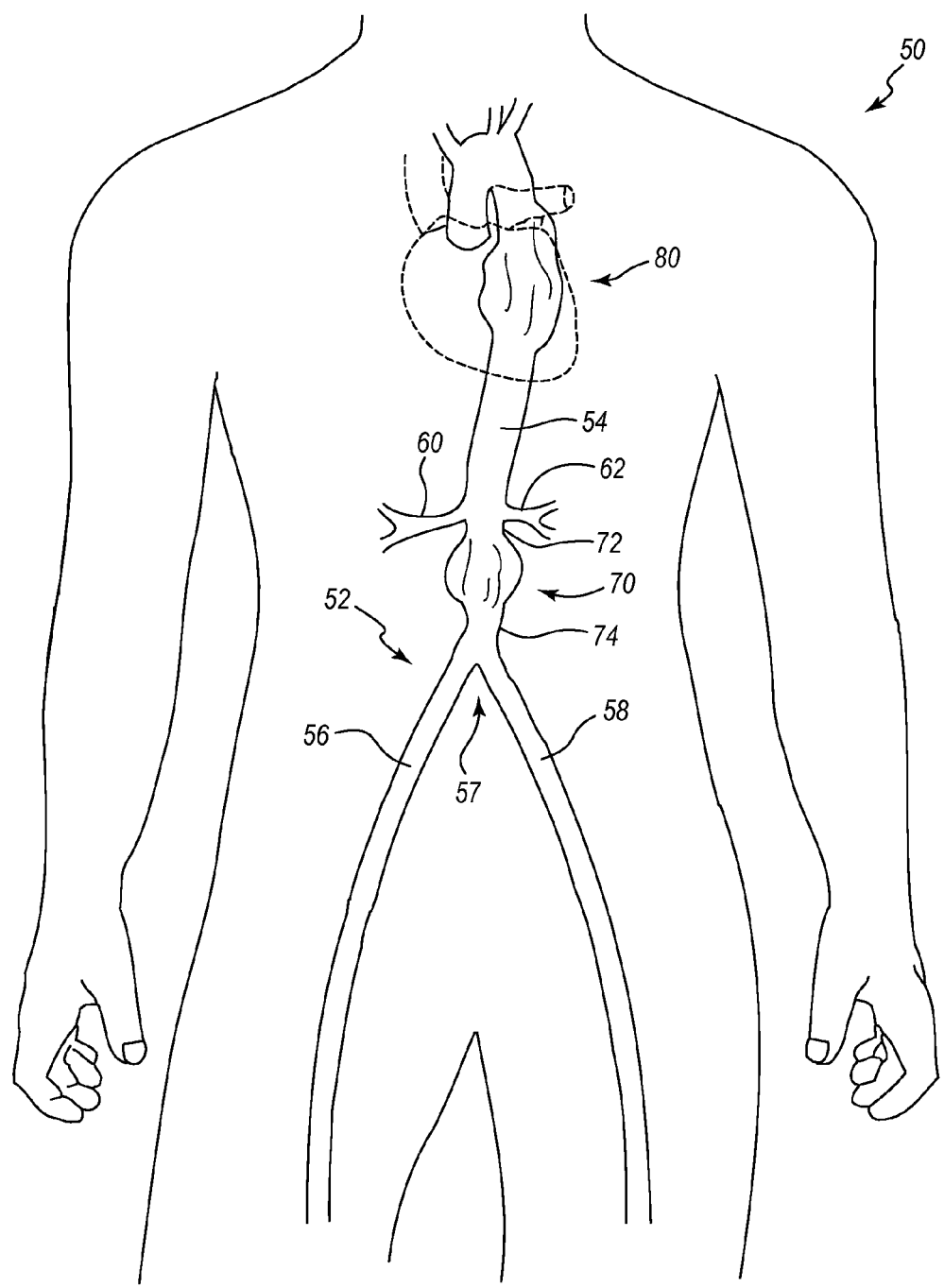
FIG. 1 is a schematic view of a portion of a vasculature of a patient.

Disclosed herein are various embodiments of implantable endovascular prostheses or stent grafts that are suitable for a variety of uses, such as the repair of aortic aneurysms. For example, certain embodiments of the stent grafts may be used to relieve pressure in abdominal aortic aneurysms and/or in thoracic aortic aneurysms. Other embodiments may be used in smaller vessels. For example, various embodiments may be suitable for use in vessels such as the coronaries. Other or further embodiments may be used in vessels having an inner diameter that is within a range of about 2 millimeters to about 30 millimeters, that is no less than about 2, 5, 10, 15, 20, 25, or 30 millimeters, or that is no greater than about 2, 5, 10, 15, 20, 25, or 30 millimeters. Other suitable uses of the stent grafts are also possible.

Certain embodiments of the stent grafts disclosed herein can provide one or more advantages over various stent grafts that are presently known in the art. For example, some known stent grafts can include both a structural stent portion and a conduit-like graft portion that are connected with each other and that are coextensive with each other over a full length (or over substantially a full length) of the implantable device when the device is packaged in a pre-use state. For example, in some arrangements, the stent and the graft are integrated with each other along a full length of the stent graft device prior to implantation of the stent graft. Due to the combined thicknesses of the stent portion and the graft portion, the implantable device can define a relatively large transverse cross-sectional area. Accordingly, in order to insert the device into the vasculature of a patient, a large vessel may be used. Such vessels may be relatively deep such that access thereto is obtained by cutting though a large amount of tissue. Additionally, a relatively large opening in the wall of a blood vessel may be created in order to insert the device into the blood vessel.

Use of a relatively large or deep blood vessel and/or creation of a relatively large opening in a vessel wall can cause discomfort to a patient and/or can result in a lengthy healing period. Moreover, due to the large cross-sectional area of the packaged device, the device may only be implanted within larger vessels. The large cross-sectional area of the packaged device also can pose risks to the patient while the device is being advanced through the vasculature of the patient to a target site. For example, in some portions of the vasculature, the device may fill a substantial area of a vessel such that the device may reduce or prevent blood flow and/or may increase blood pressure within the vessel. In other or further instances, a device that has a larger profile may be relatively prone to damaging other portions of the vasculature and/or dislodging materials from the vessel wall into the bloodstream. For example, portions of the aorta that are distanced from the abdominal aortic aneurysm may be friable, or easily crumbled.

As will be appreciated from the following disclosure, embodiments of the devices, systems, and methods disclosed herein can ameliorate and/or eliminate one or more of the foregoing issues associated with prior art devices. For example, some embodiments may be inserted through and/or implanted in smaller vessels, and smaller openings in the vessels may be used. Other or further advantages of the devices, systems, and methods are also possible. Such advantages may be relative to the illustrative prior art devices discussed above or relative to other known devices and will be evident from the discussion that follows.

FIG. 1 schematically illustrates a patient 50 and a portion of the patient's vascular system 52 (or vasculature 52). As discussed with respect to subsequent figures, various embodiments of stent graft devices can be positioned within various portions of the vasculature 52, including those portions shown in FIG. 1 as well as others. The illustrated portion of the vasculature 52 includes the aorta 54 of the patient 50. As is well known in the art, a variety of arteries branch from the aorta 54, although only several of such branches are illustrated for purposes of clarity. In particular, a terminal end of the aorta 54 branches into the right and left common iliac arteries 56, 58 at a bifurcation 57. Also branching from the aorta 54 at a more intermediate portion thereof are the right and left renal arteries 60, 62.

The illustrated vasculature 52 includes an abdominal aortic aneurysm (AAA) 70, which includes an upper end 72 that is below the renal arteries 60, 62 and a lower end 74 that is above the common iliac arteries 56, 58. Many arrangements of an abdominal aortic aneurysm 70 can differ from that shown in FIG. 1. For example, in some instances, the abdominal aortic aneurysm 70 may extend downwardly into one or more of the common iliac arteries 56, 58 and/or may comprise a collection of individual aneurysms in the vicinity of the terminal branching of the aorta 54.

Aneurysms likewise may form in other portions of the aorta 54. For example, a thoracic aneurysm (TA) 80 is additionally shown in FIG. 1. Patients are more likely to suffer from either a thoracic aneurysm or an abdominal aortic aneurysm, rather than both, although a thoracoabdominal aneurysm (TAA) such as that shown in FIG. 1 is not uncommon. One or more embodiments of devices disclosed herein may be used to repair an abdominal aortic aneurysm and/or a thoracic aneurysm. For the sake of convenience, the illustrative embodiments shown in the drawings and discussed hereafter are configured for use with an abdominal aortic aneurysm 70. It will be apparent from the following discussion that at least some of these embodiments can be readily altered for use with the thoracic aneurysm 80 and/or other target sites within the patient 50. As used herein, the term "target site" refers to any area of a vasculature 52 at which implantation of a stent graft device is desired for any suitable purpose, such as to relieve pressure threat and/or so as to otherwise provide a suitable pathway for blood flow thereby or therethrough. It is also noted that directional terms, such as upper, lower, right, and left, are used herein relative to the orientation of the patient 50 shown in FIG. 1 for the sake of convenience, but are not intended to limit the disclosure. The terms "up" and "down" may also be used with reference to upstream and downstream orientations, respectively.

Figure 3A:
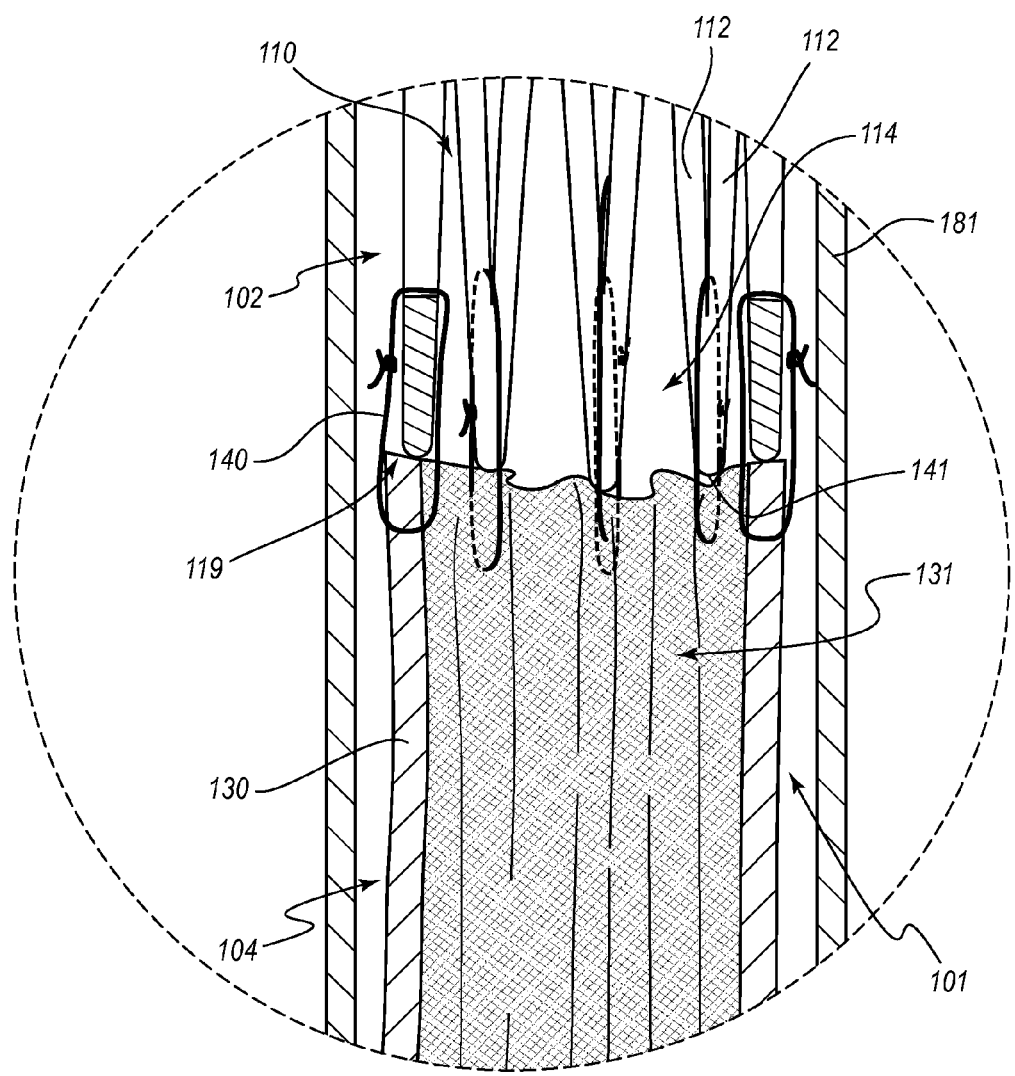
FIG. 3A is an enlarged view of the packaged portion of the stent graft assembly of FIG. 2 taken along the view line 3A in FIG. 3.

FIGS. 2-3A illustrate an embodiment of a stent graft prosthesis or stent graft assembly 100 that is configured to be implanted in the vasculature 52 of the patient 50. FIGS. 4A-4E depict an illustrative procedure for implanting the stent graft assembly 100 within the vasculature 52 of the patient 50. The following discussion describes the stent graft assembly 100 with respect to FIGS. 2-3A and occasional reference to various orientations of the stent graft assembly 100 shown in FIGS. 4A-4E, and thereafter describes the illustrative method depicted in FIGS. 4A-4E. The stent graft assembly 100 can define a small cross-sectional area when packaged in a pre-use state, as compared with known stent graft devices, such that the assembly 100 can be readily introduced through an opening 90 in a wall 53 of the vasculature 52 (see FIG. 4A) and readily advanced or otherwise moved into place through various portions of the vasculature 52.

With reference to FIG. 2, the stent graft assembly 100 can comprise a primary assembly 101 and a secondary assembly 170 that are configured to be joined with each other in situ. The primary assembly 101 may be substantially larger than the secondary assembly 170, and may comprise a trunk region that splits into branches. The secondary assembly 170, which may also be referred to as an extension, can be configured to extend one of the branches and/or anchor one of the branches within the vasculature 52.

The primary assembly 101 can include one or more stents 102, 103 which may also be referred to as anchoring devices, structural members, support elements, or endostructures, and can also include a graft 104. The stents 102, 103 can comprise any suitable material and can define any suitable shape or pattern, such as, for example, those that are presently known in the art and/or those yet to be devised. The stents 102, 103 can be configured to transition from a compressed, contracted, narrowed, restricted, or constricted state, such as that shown in FIGS. 3 and 4A, to an enlarged or expanded state, such as that shown in FIGS. 2 and 4B-4E, whether by self-expansion or by assisted expansion. In some embodiments, one or more of the stents 102, 103 comprise a resilient material and/or a shape-memory material, such as, for example, any suitable metal alloy, such as nickel titanium (e.g., Nitinol). In further embodiments, one or more of the stents 102, 103 may define a pattern that is readily compressed into a pre-use or constricted configuration in which the stent 102, 103 may be maintained until it has been situated as desired within the vasculature 52. Each stent 102, 103 may naturally transition to an expanded configuration when released from this constricted configuration. In other embodiments, each stent 102, 103 may be plastically deformable from its pre-use orientation, such as by a balloon expansion device. Certain embodiments of balloon expansion stents can comprise, for example, stainless steel. Any other suitable materials for one or more of the stents 102, 103 may be used. Additionally, it is possible for each stent 102, 103 to have different properties. For example, in some embodiments, the upper stent 102 may be plastically deformable and may be expanded via balloon inflation, whereas the lower stent 103 may be capable of automatically transitioning from the compressed packaged state to the expanded state.

The following discussion focuses on the upper stent 102, although appropriate portions of the discussion may apply equally to the lower stent 103. The stent 102 can define any suitable framework, design, or pattern. As shown in FIG. 2, the framework substantially defines a repeating "W" shape, where each segment, arm, leg, link, or branch 112 thereof is joined to neighboring branches 112 only at its ends. The branches 112 can define apertures, openings, or interstices 114 between them. In other embodiments, the stent 102 comprises a more densely packed scaffolding, frame, or mesh of interconnected branches, which define interstices of various shapes (for example, the stent 102 can resemble the stent 202 discussed below). Any suitable method for forming the stent 102 may be used, including those known in the art and those yet to be devised.

The stent 102 can provide a supporting or anchoring structure when expanded. For example, the stent 102 can press outwardly relative to portions of the wall 53 of the vasculature 52, and inwardly directed forces from the wall 53 may keep portions of the stent 102 in tension. In some embodiments, the stent 102 comprises a substantially rigid material. However, the structure of the stent 102 may be such that the stent 102 itself is resiliently flexible. The stent 102 can be configured to resist changing from a predetermined structure when displacing forces are applied thereto and/or configured to return to the predetermined structure when displaced therefrom. As shown in FIGS. 4B-4E, in the illustrated embodiment, the stent 102 can be in direct contact with the wall 53 once the stent 102 has been expanded, and the stent 102 may frictionally engage the wall. In other embodiments, only a portion of the stent 102 may directly contact the wall 53. For example, in some embodiments, a portion of the stent 102 may be drawn into the sheath 104 during deployment, such as discussed below with respect to FIGS. 47-48C.

In the illustrated embodiment, the stent 102 includes a projection, snare, or barb 105 at each apex thereof, which can further engage the stent 102 to the wall 53. More or fewer barbs 105 than those shown in FIG. 2 are possible, and the barbs 105 may be located at further or different positions of the stent 102.

As shown in FIGS. 4B-4E, the implanted stent 102 may span the renal arteries 60, 62. The stent 102 may have a generally open configuration with relatively few branches or linkages so as to permit blood flow through the stent 102 into the arteries. In other embodiments, the stent 102 may be positioned below the renal arteries 60, 62. In certain of such embodiments, the stent 102 may have a more closed configuration, which may have a relatively larger number of branches 112.

The graft 104 can comprise any suitable material and can have any suitable arrangement. For example, in some embodiments, the graft 104 comprises a cloth, fabric, or fabric-like material, which may comprise a woven material in some embodiments or a more uniform sheet of material in others. In some embodiments, the graft 104 may also be referred to as a sock. The graft 104 may have little inherent structural integrity such that its shape or configuration may readily change when forces are applied thereto. For example, the graft 104 may be less rigid than the stent 102, and may be expanded by the flow of blood through a lumen defined thereby. However, although the graft 104 may be flexible and compliant, in some embodiments, the graft 104 may be configured to maintain a natural state, or to resist being expanded beyond a natural or uncompressed state. For example, the graft 104 may readily be transitioned from a natural state (e.g., FIG. 2) to a packaged state (e.g., FIG. 3) in any suitable manner, such as by folding, rolling, or any other suitable compression technique. Deployment of the graft 104 within a vessel can transition the graft 104 from the packaged state to the natural state, but substantially no further. For example, pressure provided by blood flowing through a lumen defined by the graft 104 may not expand the graft 104, or may not substantially expand the graft 104, beyond its natural state.

In the illustrated embodiment, the graft 104 includes a flexible or compliant tube that comprises one or more of polytetrafluoroethylene (e.g., Teflon®), polyester (e.g., Dacron®), and urethane. The graft 104 can be configured to transition from the constricted or packaged state to the expanded, natural, or uncompressed state in any suitable manner. In many embodiments, the graft 104 may be folded or bunched when in the constricted state. The graft 104, which may not be formed from shape-memory materials, may be assisted into the expanded state in many embodiments via one or more of the stents 102, 103 and/or an inflation assembly (e.g., a balloon system).

In certain embodiments, a wall 130 of the graft 104 is configured to inhibit or prevent blood from passing therethrough. For example, the wall 130 may be hydrophobic and/or sufficiently thick to prevent seepage therethrough. The wall 130 thus may be configured to permit passage of blood longitudinally through a lumen 131 defined by the graft 104 without permitting the blood to seep laterally through the wall 130 itself, or stated otherwise, through an outer perimeter of the graft 104.

As shown in FIG. 2, the graft 104 can include a primary base, tube, or trunk 132 that splits into two secondary sleeves, tubes, legs, or branches 134, 136 at a bifurcation 138. The trunk 132 defines a greater maximum diameter than do either of the branches 134, 136. With additional reference to FIG. 4B, in the illustrated embodiment, the trunk 132 is configured for placement within the aorta 54, the branch 134 is configured for placement in one of the right and left common iliac arteries 56, 58, and the branch 136 is configured for placement in the other of the right and left common iliac arteries 56, 58. An upper end of the trunk 132 thus may define an inlet opening for receiving blood into the graft 104, and each of the branches 134, 136 can define an outlet opening through which blood exits the graft 104. In the illustrated embodiment, the bifurcation 138 of the graft 104 can be positioned slightly above the bifurcation 57 of the vasculature 52, at which the aorta 54 splits into the right and left common iliac arteries 56, 58.

In the illustrated arrangement, when the graft 104 is implanted, the trunk 132 spans the entirety of the abdominal aortic aneurysm 70, and the branches 134, 136 do not span any portion of the aneurysm 70. However, in other arrangements, such as those in which at least a portion of the abdominal aortic aneurysm 70 is at one or more of the right and left common iliac arteries 56, 58, one or more of the branches 134, 136 may span at least a portion of the aneurysm. In various embodiments, each branch 134, 136 may be configured for delivery to either of the arteries 56, 58.

With reference again to FIG. 2, the branch 134 can be longer than the branch 136. The branch 134 may also be referred to as a primary, extended, or anchoring branch. The extended branch 134 can be coupled with the stent 103 in any suitable manner. In some embodiments, such as that illustrated in FIGS. 1-4E, the stent 103 is attached at an exterior of the extended branch 134, whereas in other embodiments, it is attached at an interior of the extended branch 134. Any suitable attachment mechanisms are contemplated, such as sutures (not shown), adhesives, etc.

The branch 136, which may also be referred to as a secondary, shortened, or unfettered branch, can terminate at a lower edge 139 that is above an upper end of the stent 103. Stated otherwise, in the illustrated embodiment, a distance $L_1$ is defined as the distance between the bifurcation 138 and the lower edge 139; a distance $L_2$ is defined as the distance between the bifurcation 138 and the upper end of the stent 103; and the distance $L_2$ is greater than the distance $L_1$. In other embodiments, the distances $L_1$ and $L_2$ may be about the same. Further discussion regarding the stent 103 and the shortened branch 136 is provided below.

With continued reference to FIG. 2, the secondary assembly or extension 170 can be configured to extend the length of the shortened branch 134. The extension 170 can comprise an extension graft 174, which may also be referred to as a modular, adjunct, accessory, or auxiliary branch, and the extension graft 174 can be coupled with one or more stents 172, 173 in any suitable manner. In the illustrated embodiment, the stents 172, 173 are positioned at an interior of the extension graft 174. In other embodiments, one or more of the stents 172, 173 may be positioned at an exterior of the extension graft 174. As further discussed below, the extension 170 can be joined with the shortened branch 136 in any suitable manner. In some embodiments, an upper end of the extension 170 is inserted into an interior of the shortened branch 136 and then is permitted to expand so as to maintain the shortened branch 136 in an expanded and anchored state. The extension graft 174 can comprise any suitable material, such as, for example, those described above with respect to the graft 104. The stents 172, 173 can comprise any suitable material, such as, for example, those described above with respect to the stents 102, 103.

As discussed further below, the graft assembly 100 can be a modular device, where components thereof are implanted within a patient in different stages. In some embodiments, the primary assembly 101 is implanted first, and the secondary assembly 170 is then joined to the primary assembly 101.

FIG. 3 illustrates the primary assembly 101 in a packaged or constricted state. In some embodiments, a placement system 180 may be used for endovascular placement of the assembly 100. The placement system 180 can include a sheath 181 that is configured to maintain the primary assembly 101 in the constricted state during insertion of the primary assembly 101 into the vasculature 52 and during movement of the primary assembly 101 within the vasculature 52. The sheath 181 can comprise any suitable material and may be of any suitable variety, such as those known in the art or yet to be devised. In some embodiments, the sheath 181 extends upwardly beyond the upper end of the compressed stent 102 and/or extends downwardly beyond the lower end of the primary assembly 101. In the illustrated embodiment, an upper end of the sheath 181 is relatively close to the upper end of the primary assembly 101, wherein as a lower end of the sheath 181 extends downwardly beyond a lower end of the assembly 101 by a greater amount.

When the primary assembly 101 is in the constricted or packaged state, it can define a very small profile. For example, in various embodiments, a maximum diameter of the sheath 181 in which the assembly 100 is packaged can be no greater than about 6, 7, 8, 9, 10, 11, 12, 13, 14, 15, or 16 French. In some embodiments, the small profile can be achieved where the upper stent 102 does not overlap, or substantially does not overlap, an upper end of the graft 104, as discussed below.

The upper stent 102 can be larger (e.g., define a greater diameter) than the lower stent 103. In some embodiments, the lower stent 103 can be coupled with the branch 134 so as to overlap the branch 134 when in the packaged state. The additional bulk of the overlapping region, in which the lower stent 103 and the branch 134 overlap one another may nevertheless have a maximum diameter that is about the same as, or that is smaller than, a maximum diameter defined by the compressed upper stent 102. In other embodiments, the lower stent 103 may be coupled with the branch 134 in a non-overlapping manner, such as in the manner discussed below with respect to the upper stent 102 (with the lower stent 103 being attached to a lower end of the graft branch 134).

Use of a modular extension 170 can assist in reducing the bulk of the packaged primary assembly 101. For example, in the illustrated embodiment, the branch 136 does not include a stent, and instead is formed of flexible graft material that can readily be compressed to a small profile. The lower end of the branch 136 is above an upper end of the stent 103 associated with the neighboring branch 134. Accordingly, in the region where the branch 134 is adjacent to the branch 136, the graft material can be compressed to a low profile having a maximum diameter that is slightly larger than, about the same as, or smaller than a maximum diameter defined by the region of the compressed branch 134 that includes the lower stent 103.

FIG. 3A illustrates a detailed view of an upper end of the primary assembly 101. In particular, FIG. 3A illustrates a manner in which the stent 102 can be connected to the upper end of the graft 104. The illustrated connection can permit the stent 102 and the upper end of the graft 104 to define a low profile when they are in the compressed or packaged state.

In the illustrated embodiment, a plurality of sutures 140 are positioned about a periphery of the primary assembly 101 and connect the stent 102 to the graft 104. In particular, a mesh 110 of the stent 102 defines a pattern in which neighboring links 112 terminate at a nadir 141 at a lower end of the stent 102. A separate suture 140 connects each nadir 141 to the upper end of the graft 104. In some embodiments, such an arrangement can permit each portion of the upper end of the graft 104 that extends between adjacent nadirs 141 to be folded (for example, so as to project radially inwardly) when the primary assembly 101 is in the pre-use or packaged configuration, since the nadirs 141 are closer to each other when the stent 102 is in the constricted state, as compared with the expanded state (see FIG. 2). In other embodiments, the graft 104 is formed of a material that is stretchable and/or compressible, or is configured in some other suitable manner, such that folding or bunching of the graft 104, when the graft 104 is in the constricted state, either may not occur or may not significantly contribute to an overall diameter of the constricted graft 104.

In the illustrated embodiment, the lower end of the stent 102 abuts the upper end of the graft 104. Stated otherwise, the lower end of the stent 102 is radially aligned with the upper end of the graft 104 when in each of the constricted and expanded states. Accordingly, when the primary assembly 101 is in the constricted state shown in FIG. 3A, no portion of the graft 104 overlaps any portion of the stent 102. Stated otherwise, when the primary assembly 101 is in the pre-use, packaged, or constricted state, no portion of the graft 104 is either within (i.e., at an interior of) or without (i.e., at an exterior of) the stent 102 along a full longitudinal length of the stent 102.

With reference to FIG. 2, the primary assembly 101 defines a non-overlapping region 179 of the stent 102 and the graft 104 when the assembly is in the constricted state. As no portion of the stent 102 and the graft 104 overlap each other in the illustrated embodiment, the non-overlapping region 170 extends from the upper end of the stent 102 to the upper end of the stent 103. It can be seen that within the non-overlapping region, an entirety of the stent 102 is longitudinally spaced from the graft 104, except for small interface region 119 (see FIG. 3A) at the upper end of the graft 104 that is in contact with the lower end of the stent 102. The non-overlapping region 179 terminates at the upper end of the lower stent 103, since the lower stent 103 overlaps and adds bulk to the graft 104, as discussed above.

In some embodiments, the non-overlapping region 179 may have a small break or discontinuity at a position where the stent 102 interfaces with the graft 104, as a portion of the constricted graft 104 may in fact overlap a small portion of the stent 102 thereat. For example, the lower end of the stent 102 may extend downwardly past a plane defined by the upper end of the graft 104 so as to longitudinally overlap the graft 104 at an interior and/or exterior thereof.

Arrangements such as those discussed in the foregoing paragraphs can provide for a relatively narrow or small insertion package. Accordingly, the opening 90 in the wall 53 through which the primary assembly 101 is inserted into the vasculature 52 can be relatively small (see FIG. 4A), and the primary assembly 101 can define a low profile such that it occupies a small portion (or smaller portion, as compared with prior art devices) of a lateral cross section of each region of the vasculature 52 through which the primary assembly 101 is advanced.

As can be appreciated from FIG. 2, in the illustrated embodiment, an upper portion of the sheath 181 contains the stent 102 and an intermediate portion of the sheath 181 contains the graft 104, a large portion of which does not overlap the stent 103. As previously discussed, in the illustrated embodiment, there is no overlap between the graft 104 and the stent 102 when the primary assembly 101 is in the constricted state, although there is overlap between the graft 104 and the stent 103. Accordingly, for that portion of the sheath 181 that does not retain the stent 103 in the constrained state, a transverse cross-section through each point along a longitudinal axis defined by the sheath 181 intersects no more than one of the graft 104 and the stent 102. In FIGS. 3 and 3A, the longitudinal axis of the sheath 181 is not illustrated, but it is generally aligned with or coaxial with the guidewire 182 shown in FIG. 4A.

Figure 4A:
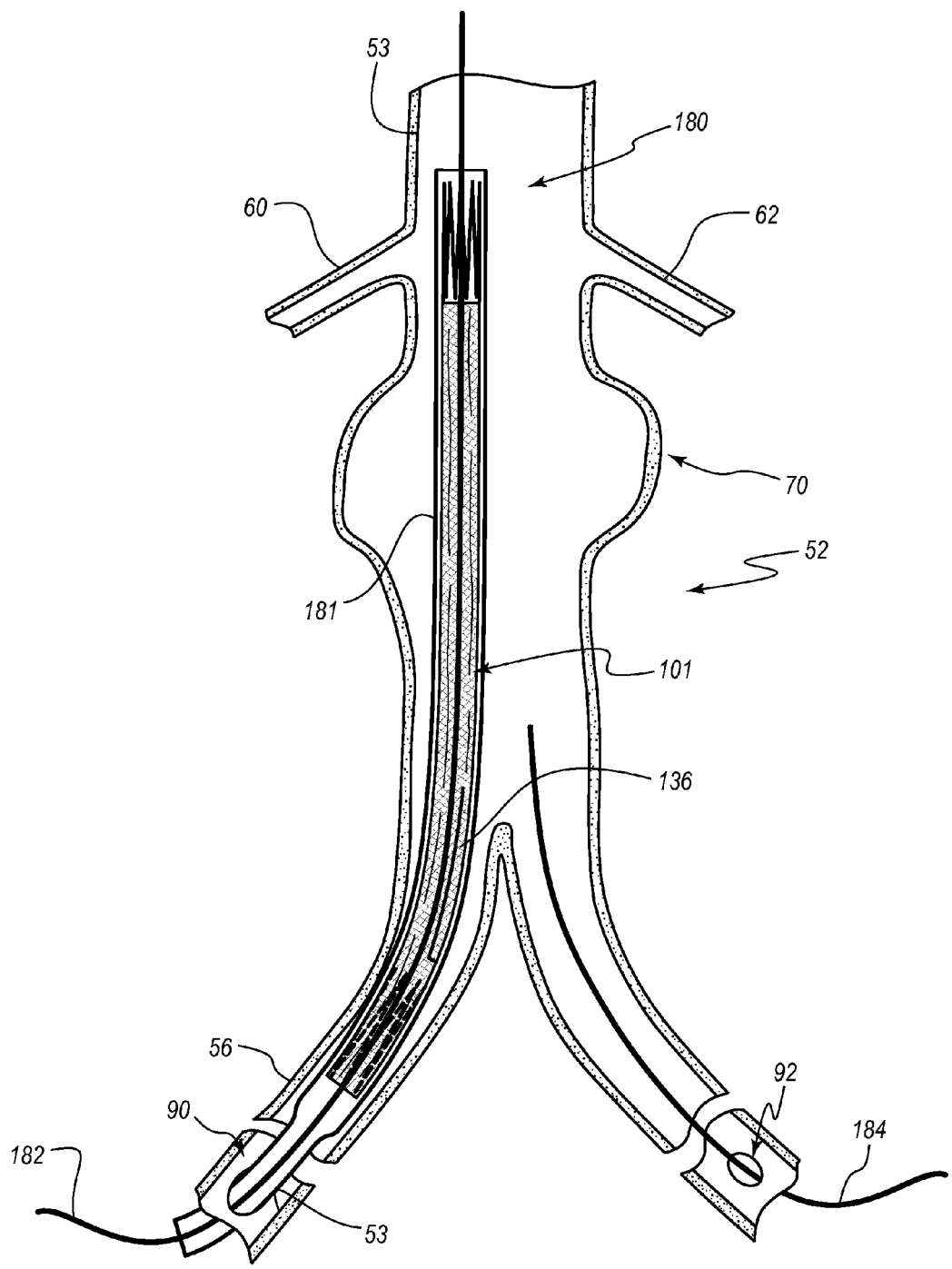
FIGS. 4A-4E are cross-sectional views of various stages for deploying the stent graft assembly of FIG. 2 within the vasculature of the patient.
Figure 4B:
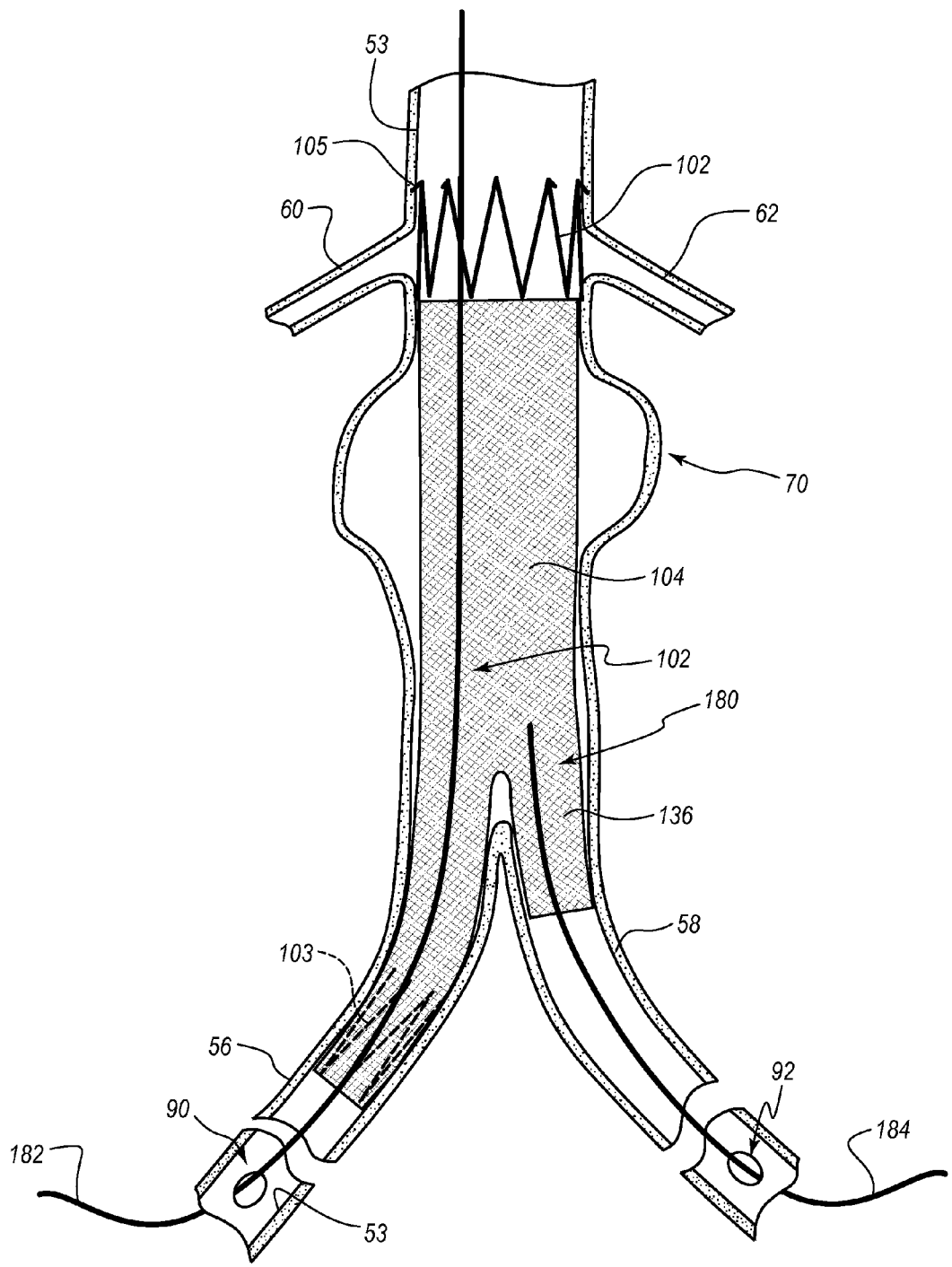
Figure 4C:
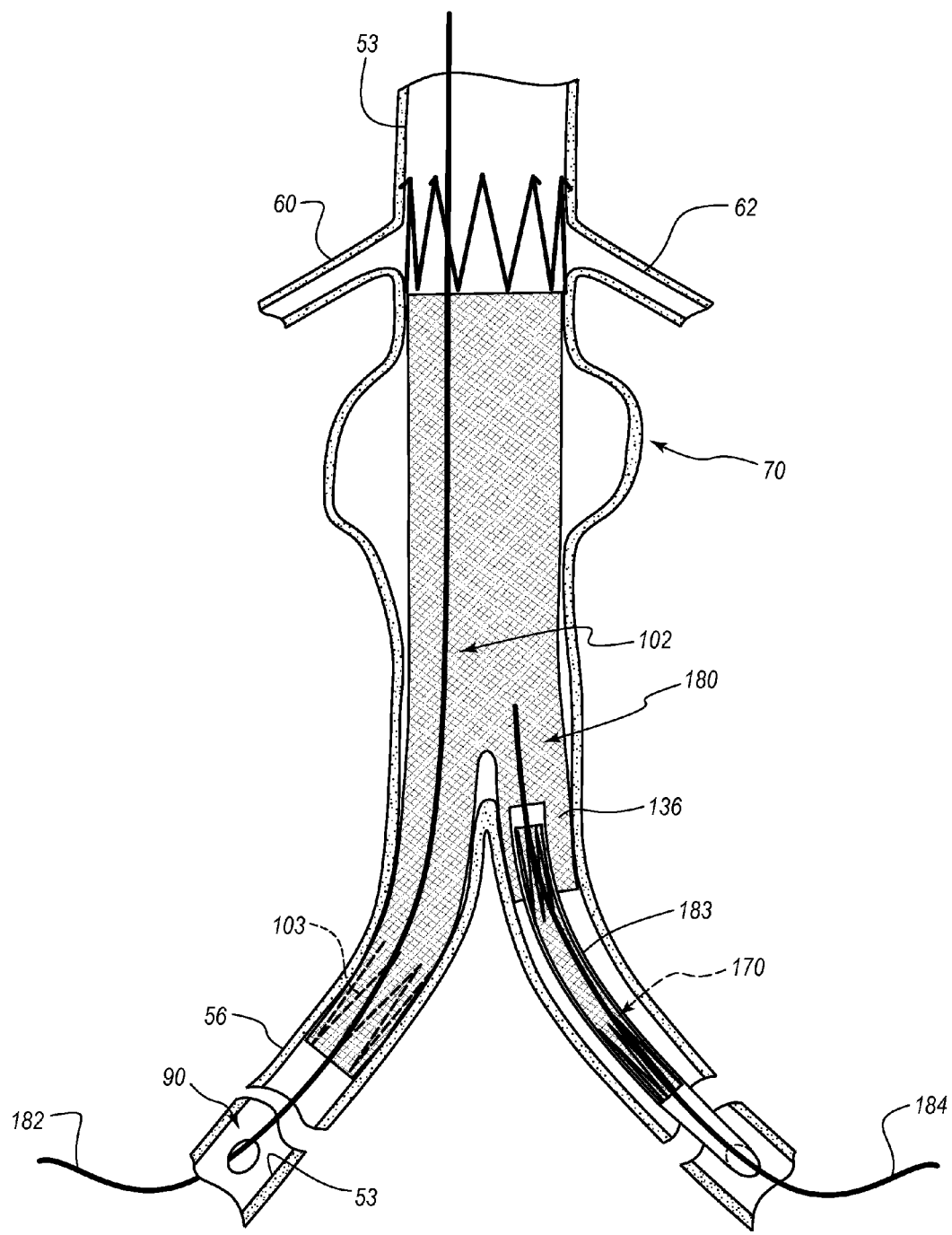

With reference briefly to FIG. 4C, the illustrated placement system 180 further comprises a sheath 183 that is configured to maintain the secondary assembly 170 in the constricted state during insertion of the secondary assembly 170 into the vasculature 52 and during movement of the secondary assembly 170 within the vasculature 52. The sheath 183 can comprise any suitable material and may be of any suitable variety, such as those known in the art or yet to be devised. The placement system 180 may further include one or more guide wires 182, 184. Use of the placement system 180 is discussed below with respect to FIGS. 4A-4E. In the illustrated embodiment, the stents 102, 103, 172, 173 are self-expanding. Accordingly, in some embodiments, an inflation system may not be used in situating the stent graft assembly 100 in the patient. However, in other embodiments, the placement system 180 can include an inflation system (e.g., an expansion balloon and related inflation apparatus) for expansion of one or more of the stents 102, 103, 172, 173 and/or the graft 104.

FIGS. 4A-4E depict various stages of an illustrative method for endovascular implantation of the stent graft assembly 100. With reference in particular to FIG. 4A, an artery in the right leg of the patient 50 may be accessed in any suitable method, such as via a standard cut-down technique. However, as can be appreciated from the foregoing, the primary assembly 101 can define a relatively small outer diameter when it is in the constricted state, and thus may be introduced into the vasculature 52 from a position that is relatively distant from a relatively large-diameter target site at which the primary assembly 101 is implanted. A percutaneous guidewire procedure (e.g., any suitable percutaneous guidewire retraction procedure) thus may be used at the remote vascular access site, rather than a standard cutdown technique that is closer to the target site (and thus may be more invasive). This can reduce trauma to the patient.

An opening 90 can be formed in a wall 53 of the artery and the guidewire 182 can be inserted therethrough. The guidewire 182 can be advanced through the vasculature 52 to a position that is slightly upstream of the position to which an upper end of the sheath 181 is to be advanced. The primary stent graft assembly 101, in its constricted and packaged state, can then be advanced over the guidewire 182, through the opening 90, and into the desired position within the vasculature 52. In some embodiments, at least a portion of the stent 102 and/or at least a portion of the graft 104 may be radiopaque such that the position of the primary assembly 101 within the vasculature 52 may be monitored via standard techniques.

An artery in the left leg may also be accessed in any suitable method, such as via a standard cut-down technique. However, as can be appreciated from the foregoing, the secondary assembly 170 can define a relatively small outer diameter when it is in the constricted state, and thus may be introduced into the vasculature 52 from a position that is relatively distant from the relatively large-diameter target site at which the secondary assembly 170 is implanted. A percutaneous guidewire procedure thus may be used instead at this vascular access site.

An opening 92 can be formed in a wall 53 of the artery and the guidewire 184 can be inserted therethrough. The guidewire 184 can be advanced through the vasculature 52 to a position at which the branch 136 may eventually be accessed. Although placement of the guidewire 184 is depicted as taking place before expansion of the primary assembly 101 in the illustrated procedure, in other implementations, the guidewire 184 may be introduced into the vasculature 52 at a later stage of the procedure.

With reference to FIG. 4B, once the primary assembly 101 is in the desired position, the sheath 181 can be retracted from the assembly 101 and removed through the opening 90. The stents 102, 103 may expand so as to frictionally engage the vessel wall 53. In some embodiments, the barbs 105 of the upper stent 102 can be embedded in the vessel wall 53. The stents 102, 103 can fix, anchor, or secure the graft 104 in place. In some embodiments, the stents 102, 103 are biased toward the expanded configuration, and in other or further embodiments, heating within the patient (e.g., due to blood) may move the stents 102, 103 to a remembered state. The stent 102 can press the upper end of the graft 104 into close proximity and/or contact with the vessel wall 53. In the illustrated embodiment, the stent 102 and the graft 104 remain in a non-overlapping configuration when the primary assembly 101 is in the expanded or deployed state. In other embodiments, at least a lower portion of the stent 102 and an upper end of the graft 104 may overlap (whether the stent 102 is internal or external to the graft 104) when the primary assembly 101 is in the deployed state. For example, in some embodiments, the stent 102 may move relative to the graft 104 during deployment, as discussed below with respect to FIGS. 47-48C.

In some embodiments, the force provided by the stent 102 and/or the pressure provided by blood flowing through the lumen of the graft 104 can be sufficient to maintain the upper, or upstream, end of the graft 104 against the vessel wall 53. In such embodiments, the upper end of the graft 104 can achieve, or substantially achieve, hemostasis about its periphery so as to prevent or inhibit blood from passing at an exterior of the graft 104 into the region between the aneurysm 70 and the outer surface of the graft 104. Blood that flows into the upper end of the graft 104 may expand other portions of the graft 104 (e.g., an intermediate region extending between the stents 102, 103).

As previously discussed, in some embodiments, the graft 104 is configured to expand to a natural state (e.g., that shown in FIG. 2), but not beyond. The graft 104 may have sufficient lateral strength to resist expansion in the radial direction as blood flows through it. Accordingly, the graft 104 may reduce or eliminate pressure against the vessel wall 53 in the region of the aneurysm 70. Stated otherwise, the graft 104 may function independently of any secondary support structure along a length thereof that is in the vicinity of the aneurysm 70.

As shown in FIG. 4B, the shortened branch 136 can be loose or unattached to the vessel wall 53. The branch 136 can be manipulated or otherwise transitioned from an initial position within the right common iliac artery 56 (see FIG. 4A) into the left common iliac artery 58 via any suitable method or technique. For example, in some implementations, a snare (not shown) or other suitable device may be advanced alongside the guidewire 184. The snare may catch or capture the branch 136 and pull it downwardly into the left common iliac artery 58 so that the branch 136 encompasses an end portion of the guidewire 184. In some embodiments, blood flow through the branch 136 may assist in moving the branch 136 into the left common iliac artery 58.

With reference to FIG. 4C, the secondary assembly 170 may be advanced over the guidewire 184 to the desired position. In the illustrated implementation, an upper end of the secondary assembly 170 is positioned at an interior of the shortened branch 136.

Figure 4D:
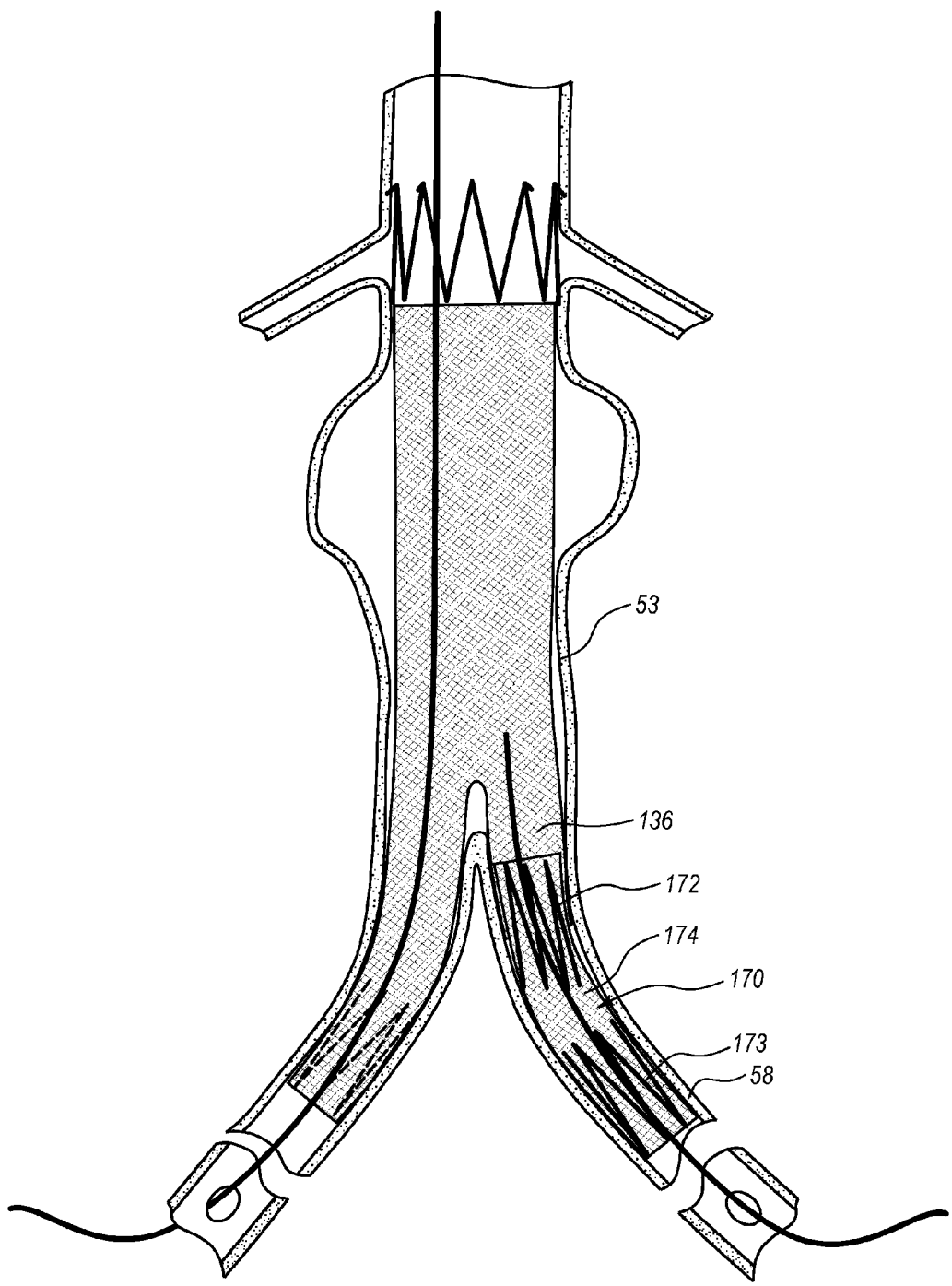

With reference to FIG. 4D, the sheath 183 can be removed so as to permit the secondary assembly 170 to automatically expand into contact and frictional engagement with the branch 136 and the wall 53 of the left common iliac artery 58. For example, the stents 172, 173 may be biased toward an expanded configuration, and/or may be urged to a remembered state due to heating (e.g., due to blood flow). In other embodiments, one or more of the stents 172, 173 can be expanded via balloon inflation or other suitable techniques. The extension graft 174 can frictionally engage an inner surface of the branch 136 at an upper end thereof, and may achieve hemostasis so as to prevent seepage about its outer perimeter.

Figure 4E:
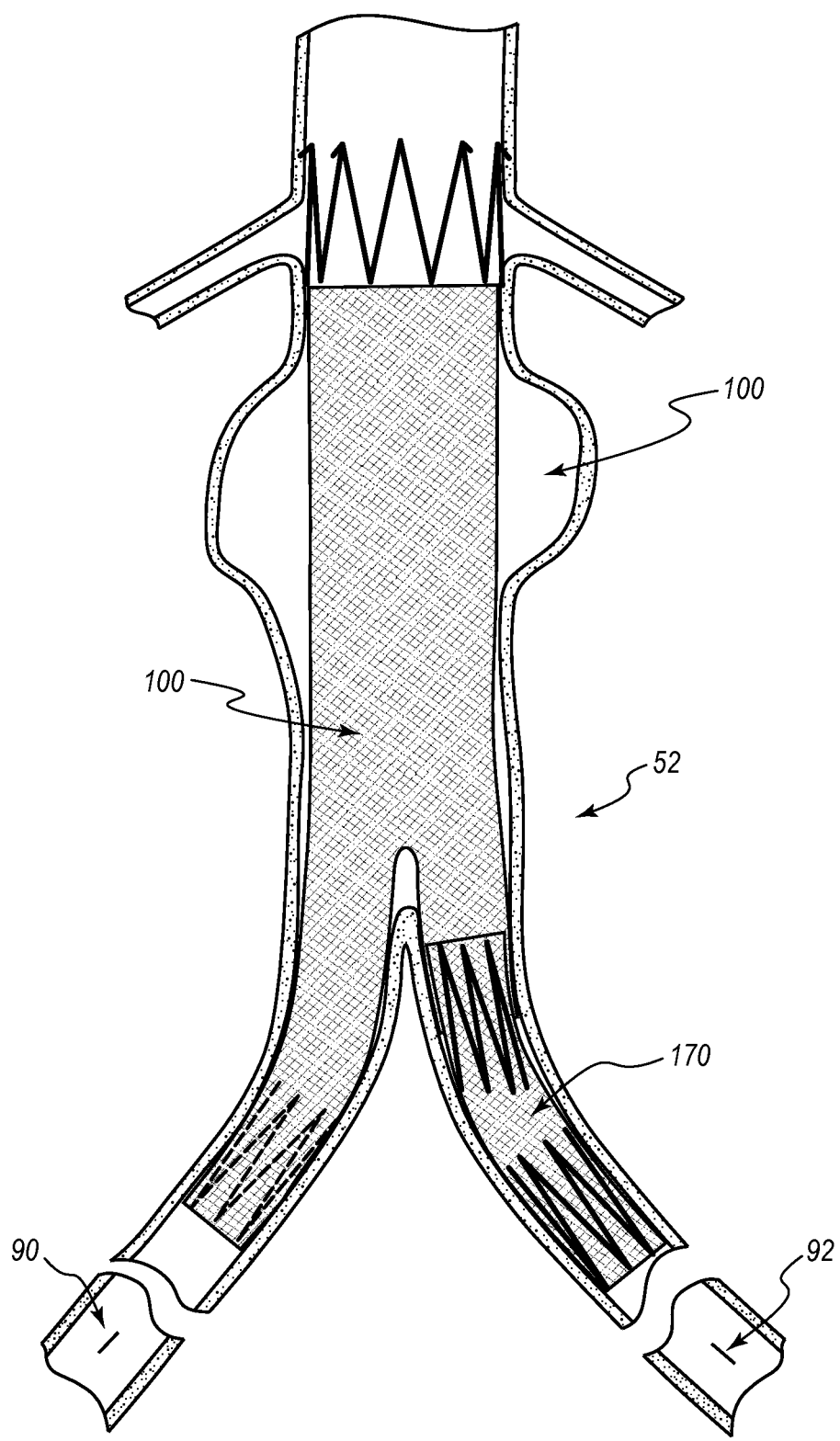

With reference to FIG. 4E, the guidewires 182, 184 can be removed through the openings 90, 92. Thereafter, the openings 90, 92, and any neighboring tissue which may have been cut, punctured, or otherwise manipulated to access the vasculature 52 can be closed and permitted to heal in any suitable manner.

Assembling the separate components of the stent graft assembly 100 in situ, such as by separately introducing the first and second assemblies 101, 170 into the vasculature 52 via separate openings 90, 92, can result in less trauma to a patient. The openings through the tissue used to access the vasculature 52 can be smaller, as compared with other techniques, and the vasculature 52 can be accessed at regions that have smaller diameter vessels than, and are remote from, the implantation site within the patient (e.g., the junction of the aorta and the common iliac arteries). In some implementations, both the primary and secondary assembly portions 101, 170 of the stent graft assembly 100 may be deployed in the vasculature 52 via the opening 90 using any suitable endovascular placement technique (e.g., any suitable technique known to those skilled in the art).

Figure 5A:
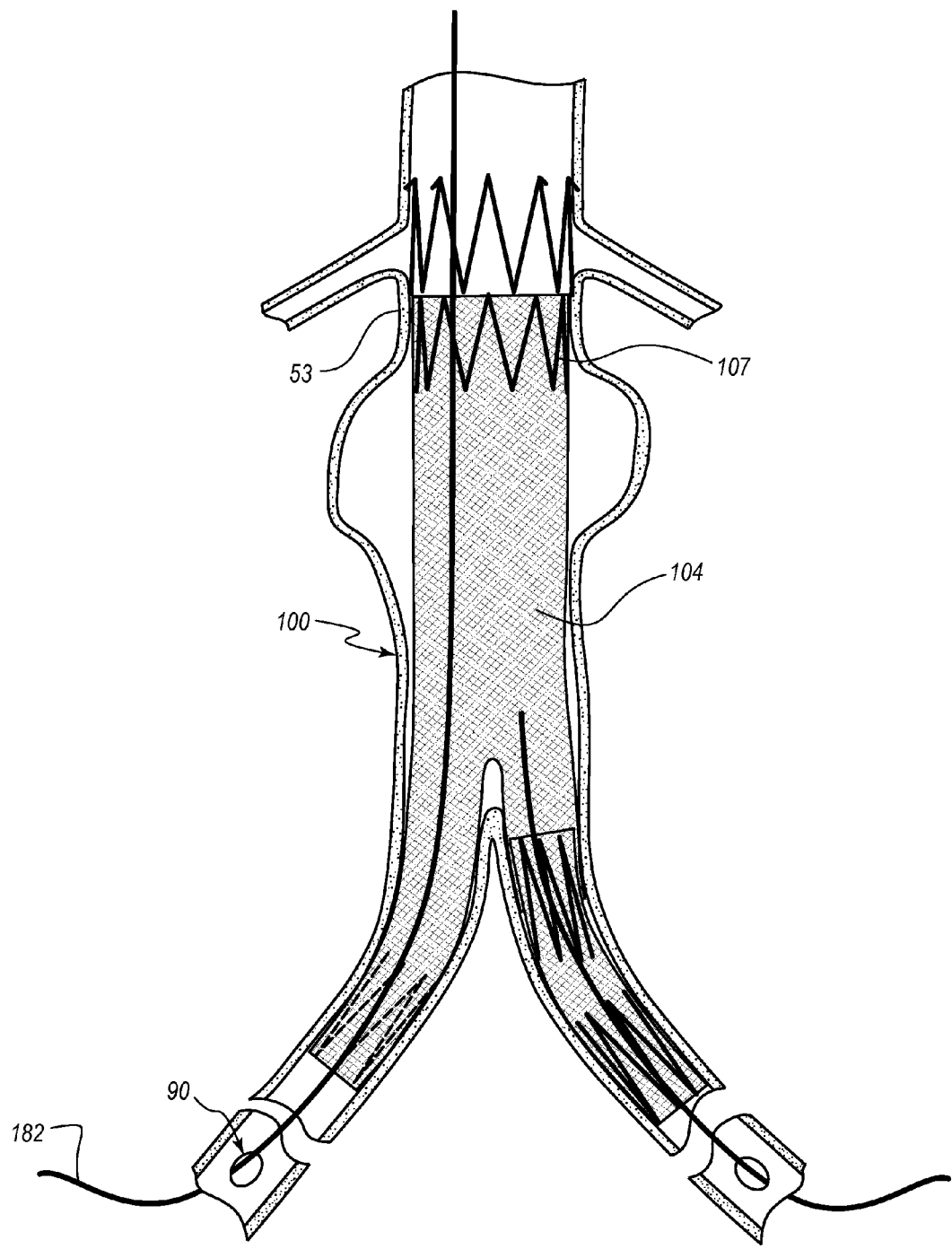
FIG. 5A is a cross-sectional view of another embodiment of a stent graft assembly such as that of FIG. 2, which illustrates an additional stage of deployment within the vasculature of the patient.

FIG. 5A illustrates another embodiment of the stent graft assembly 100 that further includes a stent 107. The stent 107 can resemble any of the stents described above. The stent 107 can be introduced into an interior of the graft 104 at any suitable stage of the procedure depicted in FIGS. 4A-4E. In the illustrated implementation, the stent 107 is introduced into the interior of the graft 104 at a stage that is after that depicted in FIG. 4D and before that depicted in FIG. 4E. The graft 104 may be held in a compressed state via a sheath (not shown) and may be advanced over the guidewire 182 to the desired position. The sleeve may then be removed to permit the stent 107 to expand into contact with an upper end of the graft 104. The stent 107 can press the graft 104 against the vessel wall 53 by a greater amount than that discussed above (e.g., due to the upper stent 102 and blood pressure), and thus may assist in achieving hemostasis and fixation to the vasculature 52 at an upper end of the graft 104. In other embodiments, the stent 107 may be expanded into place via an expansion assembly (e.g., a balloon).

Figure 5B:
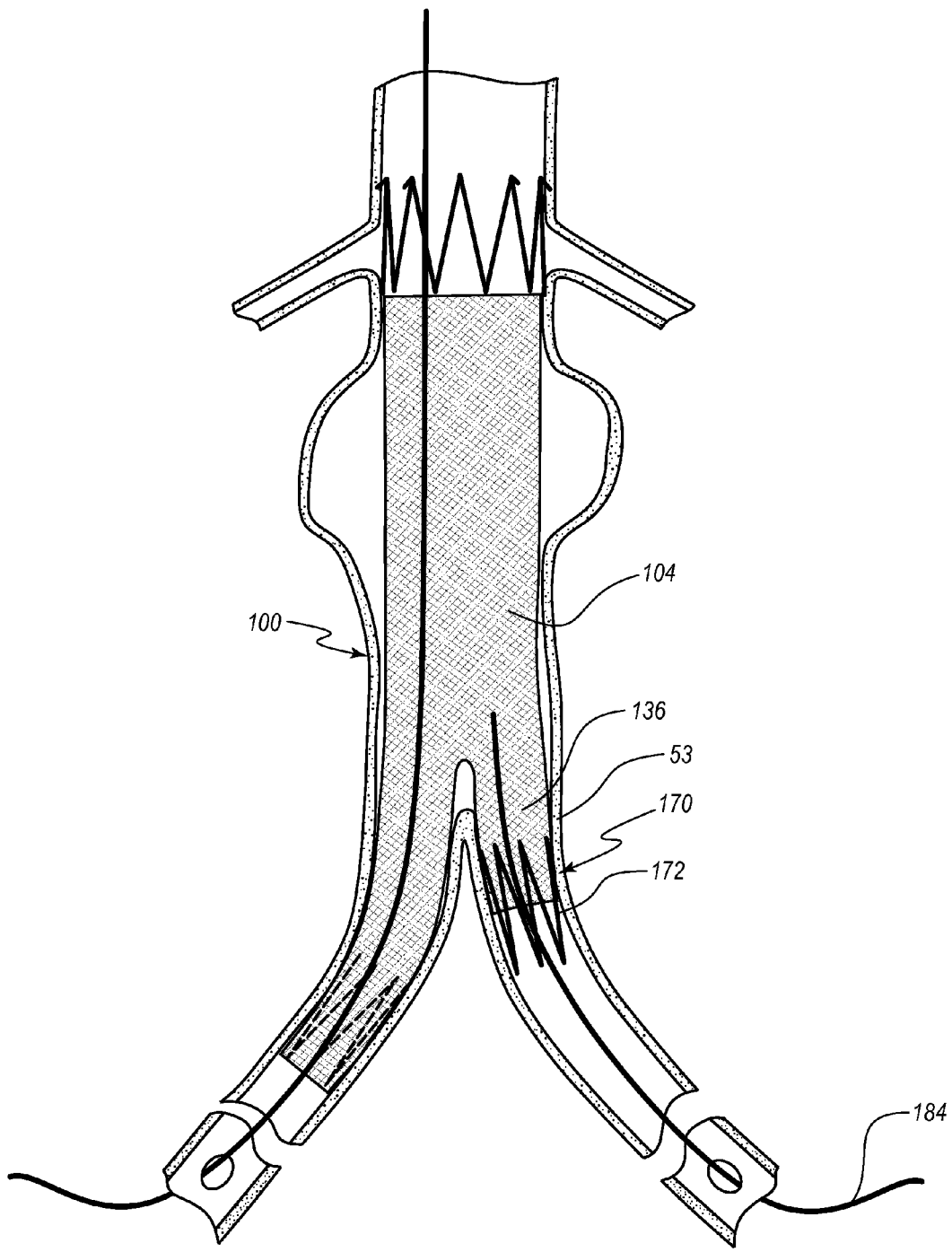
FIG. 5B is a cross-sectional view of yet another embodiment of a stent graft assembly such as that of FIG. 2.

FIG. 5B illustrates another embodiment of the stent graft assembly 100 that includes a different embodiment of the extension 170. In particular, rather than including an extension graft piece and multiple stents, the extension 170 includes a single stent 170 that can be used to secure the branch 136 of the graft 104 to the vessel wall 53. Although not shown in FIG. 5B, in some embodiments, the stent 107 may be used with the stent graft assembly 100.

FIGS. 6-12 depict another embodiment of a stent graft prosthesis or stent graft assembly 200, components thereof, and methods for assembling the stent graft assembly 200 in situ. The stent graft assembly 200, and components thereof, can resemble the stent graft assembly 100, and components thereof, described above in certain respects. Accordingly, like features are designated with like reference numerals, with the leading digits incremented to "2." Relevant disclosure set forth above regarding similarly identified features thus may not be repeated hereafter. Moreover, specific features of the stent graft assembly 200 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the stent graft assembly 200. Any suitable combination of the features and variations of the same described with respect to the stent graft assembly 100 can be employed with the stent graft assembly 200, and vice versa. This pattern of disclosure applies equally to further embodiments depicted in subsequent figures and described hereafter, for which leading digits may likewise be incremented.

The stent graft assembly 200 is configured to be implanted in the vasculature 52 of the patient 50. As further discussed hereafter, the stent graft assembly 200 can define a small cross-sectional area when packaged in a pre-use state, as compared with known stent graft devices, such that the assembly 200 can be readily introduced through an opening 90 in a wall 53 of the vasculature 52 and readily advanced or otherwise moved into place through various portions of the vasculature 52.

Figure 6:
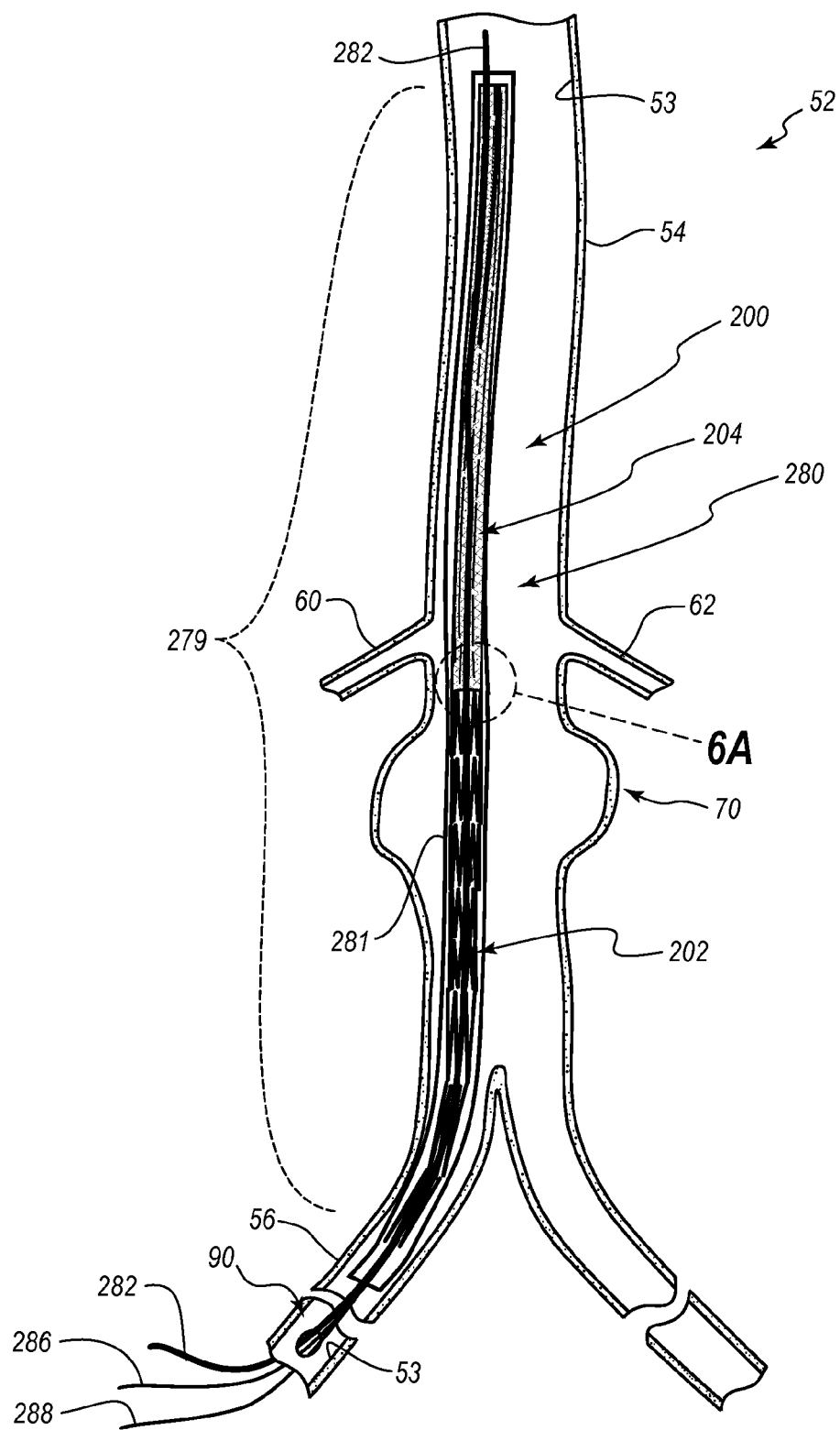
FIG. 6 is a cross-sectional view of a stage of an illustrative procedure for implanting another embodiment of a stent graft assembly within the vasculature of a patient.

With reference to FIG. 6, the stent graft assembly 200 can comprise a stent 202, which may also be referred to as a structural member or endostructure, and can also comprise a graft 204. The stent 202 can comprise any suitable material and can define any suitable shape or pattern, such as, for example, those that are presently known in the art and/or those yet to be devised. The stent 202 can be configured to transition from a compressed, contracted, narrowed, restricted, or constricted state, such as that shown in FIG. 6, to an enlarged or expanded state, such as that shown in FIG. 7, whether by self-expansion or by assisted expansion. In some embodiments, the stent 202 comprises a resilient material and/or a shape-memory material, such as, for example, any suitable metal alloy, such as nickel titanium (e.g., Nitinol). In further embodiments, the stent 202 may define a pattern that is readily compressed into a pre-use or constricted configuration in which the stent 202 may be maintained until it has been situated as desired within the vasculature 52. The stent 202 may naturally transition to an expanded configuration when released from this constricted configuration. In other embodiments, the stent 202 may be plastically deformable from its pre-use orientation, such as by a balloon expansion device. Certain embodiments of balloon expansion stents can comprise, for example, stainless steel. Any other suitable materials for the stent 202 may be used.

Figure 7:
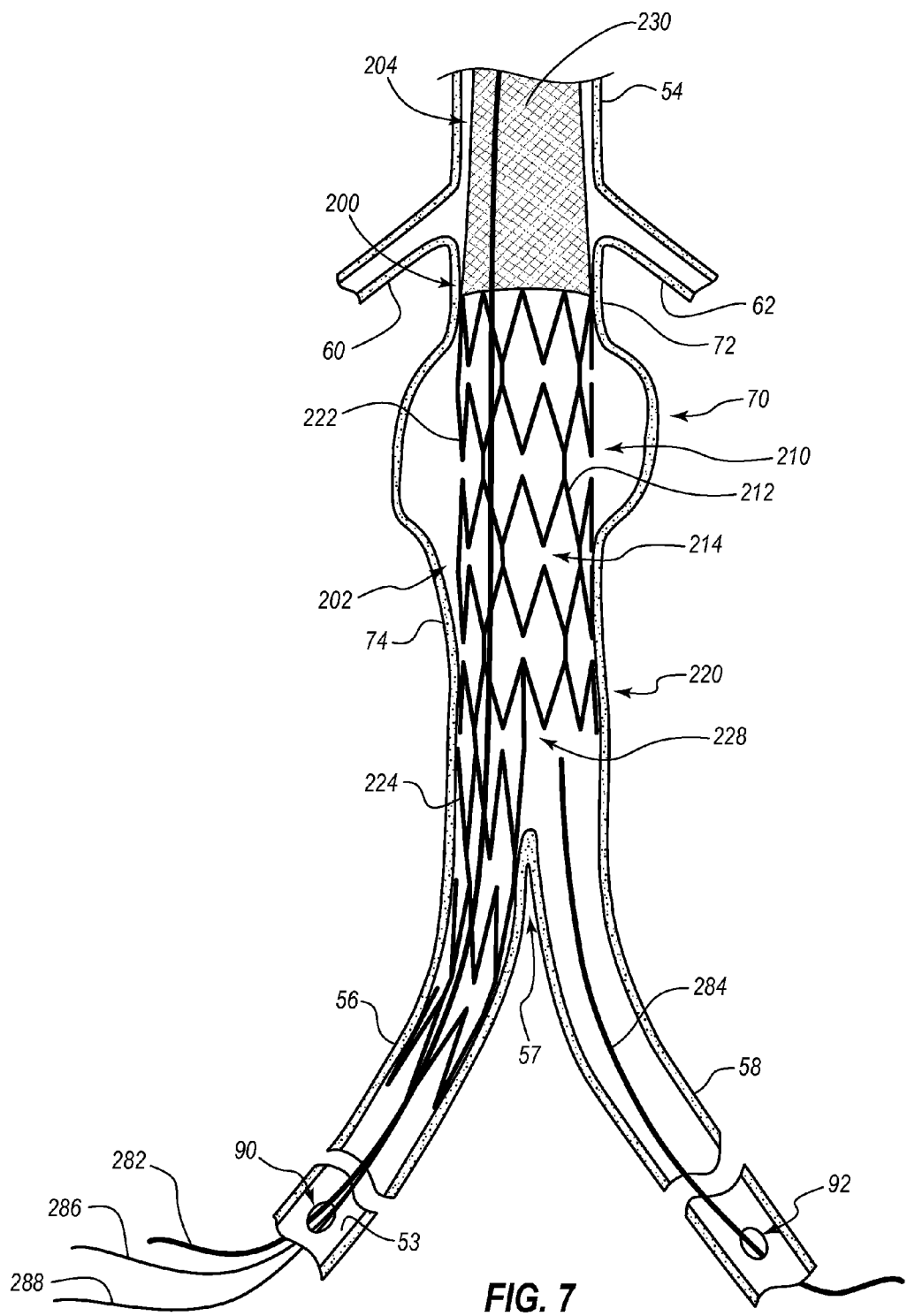
FIGS. 7-11 are cross-sectional views of additional stages of the procedure of FIG. 6.

The stent 202 can define any suitable framework, design, or pattern. As shown in FIG. 7, in the illustrated embodiment, the stent 202 comprises a scaffolding, frame, or mesh 210 of interconnected segments, sections, arms, legs, or links 212, which define apertures, openings, or interstices 214 of various shapes. The mesh 210 can be formed in any suitable manner. For example, in some embodiments, the links 212 may result when material in the shape of the interstices 214 is laser etched or otherwise removed from a tubular structure. Any suitable method for forming the stent 202 may be used, including those known in the art and those yet to be devised.

The stent 202 can provide a supporting structure when expanded. For example, the stent 202 can press outwardly relative to portions of the wall 53 of the vasculature 52, and inwardly directed forces from the wall 53 may keep portions of the stent 202 in tension. In some embodiments, the stent 202 comprises a substantially rigid material. However, the structure of the stent 202 may be such that the stent 202 itself is resiliently flexible. The stent 202 can be configured to resist changing from a predetermined structure when displacing forces are applied thereto and/or configured to return to the predetermined structure when displaced therefrom. As shown in FIGS. 7-12, in the illustrated embodiment, portions of the stent 202 can be in direct contact with the wall 53 once stent 202 has been expanded, and the stent 202 may frictionally engage the wall.

As shown in FIGS. 7-11, the implanted stent 202 may span at least a portion of the abdominal aortic aneurysm 70. The spanning portion of the stent 202 can define a contour of a path through the abdominal aortic aneurysm 70. The path is generally smaller than the abdominal aortic aneurysm 70, in cross-sectional area. In this region, the stent 202 might not press outwardly against the wall 53 of the stent so as to maintain a position of the stent 202 within the vasculature 52. In particular, in much or all of this spanning region, depending on the arrangement of the abdominal aortic aneurysm 70, the stent 202 does not contact or otherwise interact with the wall 53. In this region, the stent 202 may instead provide a self-supporting structure against which the graft 204 can press (or be pressed, such as by blood) when the assembly 200 is in use, as further discussed below. In the illustrated embodiment, the spanning portion of the stent 202 extends between the upper end 72 and the lower end 74 of the abdominal aortic aneurysm 70.

In the illustrated embodiment, the stent 202 comprises two separate pieces that can be approximated to each other and/or attached to each other in situ. In particular, the stent 202 comprises a primary section 220 and a secondary section 221, as shown for example in FIGS. 7 and 8. The upper section 220 comprises a base or trunk 222 and a leg or branch 224. The trunk 222 defines a greater diameter than the branch 224. In the illustrated embodiment, the trunk 222 is configured for placement within the aorta 54, and the branch 224 is configured for placement in the right common iliac artery 56. The lower section 221 comprises a branch 226 that is configured to be approximated to and, in some embodiments, connected with a lower end of the upper section 220, and is configured for placement in the left common iliac artery 58. The upper and lower sections 220, 221 can meet at a bifurcation 228 of the stent 202. In the illustrated embodiment, as seen for example in FIG. 12, the bifurcation 228 of the stent 202 is positioned slightly above the bifurcation 57 of the vasculature 52 at which the aorta 54 splits into the right and left common iliac arteries 56, 58. It is noted that directional terms such as upper, lower, right, and left are used herein relative to the positions shown in FIG. 6 for the sake of convenience, but are not intended to limit the disclosure.

In the illustrated embodiment, the trunk 222 of the stent 202 spans the entirety of the abdominal aortic aneurysm 70, and the right and left branches 224, 226 do not span any portion of the aneurysm 70. However, in other arrangements where at least a portion of the abdominal aortic aneurysm 70 is at one or more of the right and left common iliac arteries 56, 58, one or more of the right and left branches 224, 226, respectively, may span at least a portion of the aneurysm. In still other or further embodiments, such as those that may be used with a thoracic aneurysm 80, the stent 202 may not include a bifurcation (e.g., may have a trunk, but no branches).

The graft 204 can comprise any suitable material and can have any suitable arrangement. For example, in some embodiments, the graft 204 comprises a cloth, fabric, or fabric-like material, which may comprise a woven material in some embodiments or a more uniform sheet of material in others. The graft 204 may have little inherent structural integrity such that its shape or configuration may readily change when forces are applied thereto. For example, the graft 204 may be less rigid than the stent 202. In some embodiments, the graft 204 may also be referred to as a sock. In the illustrated embodiment, the graft 204 includes a flexible or compliant tube that comprises one or more of polytetrafluoroethylene (e.g., Teflon®), polyester (e.g., Dacron®), and urethane. The graft 204 can be configured to transition from a constricted state to an expanded state. In many embodiments, the graft 204 may be folded or bunched when in the constricted state. The graft 204 may be assisted into the expanded state in many embodiments, which may not be formed from shape-memory materials.

In certain embodiments, a wall 230 of the graft 204 is configured to inhibit or prevent blood from passing therethrough. For example, the wall 230 may be hydrophobic and/or sufficiently thick to prevent seepage therethrough. The wall 230 thus may be configured to permit passage of blood through a lumen defined by the graft 204 without permitting the blood to seep through an outer boundary defined by the graft 204.

Figure 9:
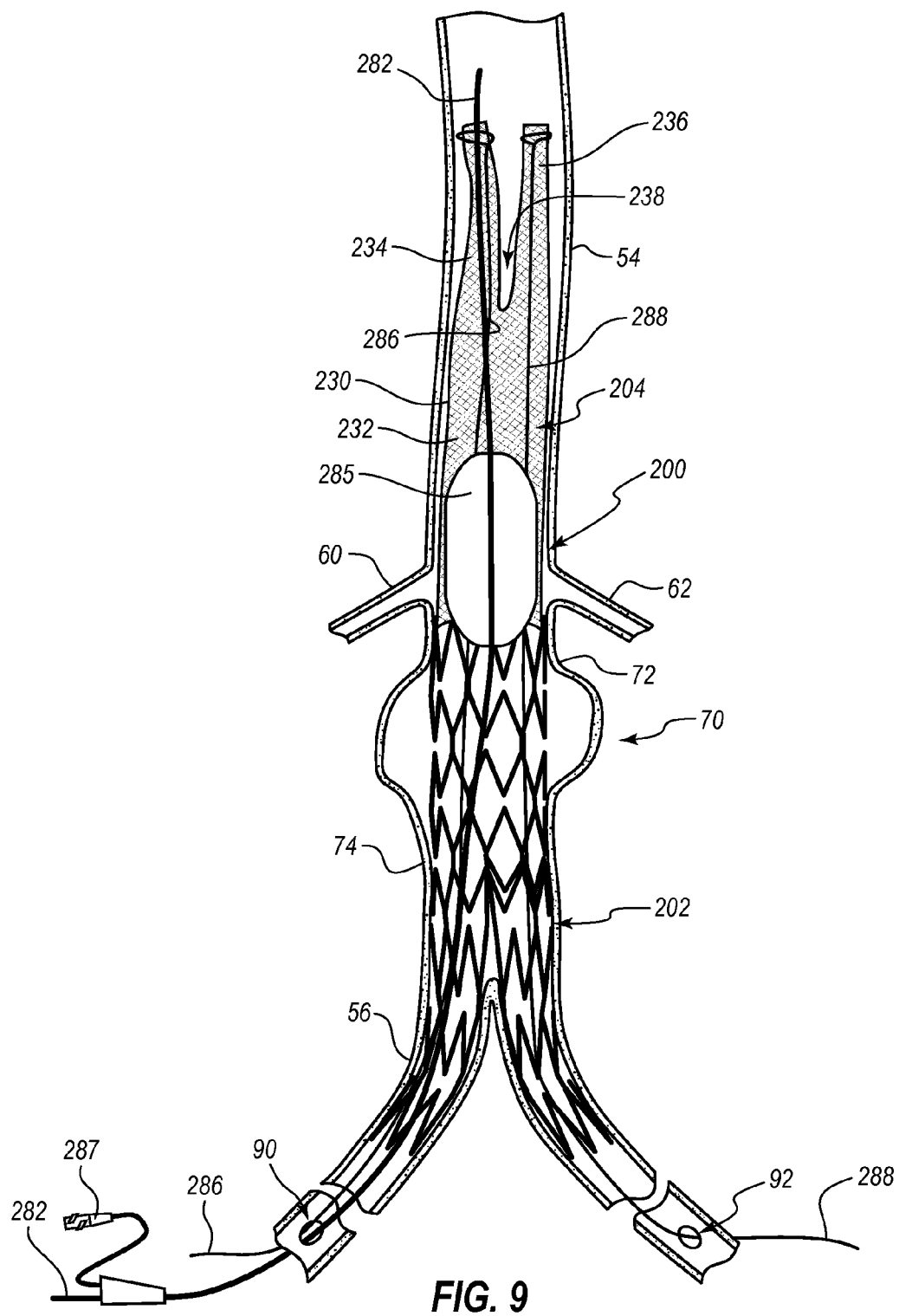

As shown in FIG. 9, the graft 204 can include a primary base, tube, or trunk 232 that splits into two secondary branches, tubes, legs, or sleeves 234, 236 at a bifurcation 238. The trunk 232 and sleeves 234, 236 are discussed further below. In other embodiments, such as those that may be used with a thoracic aneurysm 80, the graft 204 may not include a bifurcation (e.g., may have a trunk, but no branches).

With reference to FIGS. 6, 6A, 12, and 12A, an upper end of the stent 202 can be connected to a lower end of the graft 204. As described further below, the graft 204 may be repositioned relative to the stent 202 in situ. Accordingly the term "lower end" of the graft refers to the arrangement shown in FIG. 6 since, after the repositioning of the graft 204 to arrive at the arrangement shown in FIG. 12, the "lower end" of the graft 204 is in fact at or near the upper end of the implanted assembly 200.

Figure 6A:
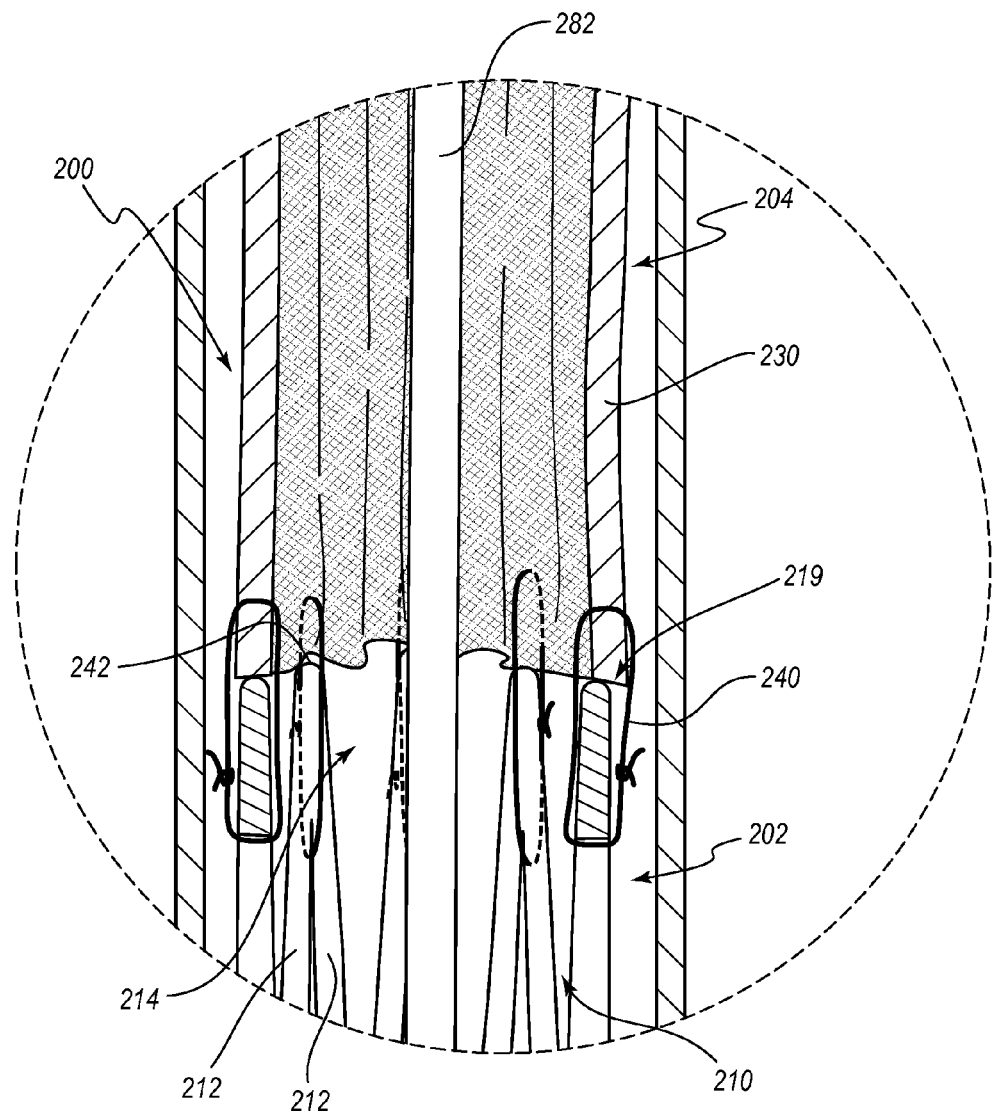
FIG. 6A is an enlarged partial cross-sectional view taken along the view line 6A in FIG. 6.

With further reference to FIG. 6A, any suitable connection between the stent 202 and the graft 204 is possible. In the illustrated embodiment, a plurality of sutures 240 are positioned about a periphery of the assembly 200 and connect the stent 202 to the graft 204. In particular, the mesh 210 of the stent 202 defines a pattern in which neighboring links 212 terminate at an apex 242 at an upper end of the stent 202. A separate suture 240 connects each apex 242 to the lower end of the graft 204. In some embodiments, such an arrangement can permit each portion of the lower end of the graft 204 that extends over an interstice 214 that is between adjacent apexes 242 to be folded (for example, so as to project radially inwardly) when the assembly 200 is in the pre-use or packaged configuration, since the apexes 242 are closer to each other when the stent 202 is in the constricted state, as compared with the expanded state (see FIG. 12A). In other embodiments, the graft 204 is formed of a material that is stretchable and/or compressible, or is configured in some other suitable manner, such that folding or bunching of the graft 204 when the graft 204 is in the constricted state either may not occur or may not significantly contribute to an overall diameter of the constricted graft 204.

In the illustrated embodiment, the lower end of the graft 204 abuts the upper end of the stent 202. Stated otherwise, the lower end of the graft 204 is radially aligned with the upper end of the stent 202 when in each of the constricted and expanded states. Accordingly, when the assembly 200 is in the constricted state shown in FIG. 6A, no portion of the graft 204 overlaps any portion of the stent 202. Stated otherwise, when the assembly 200 is in the pre-use, packaged, or constricted state, no portion of the graft 204 is either within (i.e., at an interior of) or without (i.e., at an exterior of) the stent 202 along a full longitudinal length of the stent 202.

With reference to FIG. 6, the assembly 200 defines a non-overlapping region 279 of the stent 202 and the graft 204 when the assembly is in the constricted state. As no portion of the stent 202 and the graft 204 overlap each other in the illustrated embodiment, the non-overlapping region 279 extends from the upper end of the graft 204 to the lower end of the stent 202. It can be seen that within the non-overlapping region, an entirety of the stent 202 is longitudinally spaced from the graft 204, except for small interface region 219 (see FIG. 6A) at the upper end of the stent 202 that is in contact with the lower end of the graft 204. As further discussed below, the graft 204 can be rearranged relative to the stent 202 in situ so as to reduce or eliminate the non-overlapping region 279.

In some embodiments, the non-overlapping region 279 may have a small break or discontinuity at a position where the stent 202 interfaces with the graft 204, as a portion of the constricted graft 204 may in fact overlap a small portion of the stent 202 thereat. For example, the lower end of the graft 204 may extend downwardly past a plane defined by the upper end of the stent 202 so as to longitudinally overlap the stent 202 at an interior and/or exterior thereof.

Arrangements such as those discussed in the immediately preceding paragraphs can provide for a relatively narrow or small insertion package. Accordingly, the opening 90 in the wall 53 through which the assembly 200 is inserted into the vasculature 52 can be relatively small, and the assembly 200 can define a low profile such that it occupies a small portion (or smaller portion, as compared with prior art devices) of a lateral cross section of each region of the vasculature 52 through which the assembly 200 is advanced.

With reference again to FIG. 6, In various embodiments, a system 280 may be used for endovascular placement of the assembly 200. The system 280 can include a sheath 281 that is configured to maintain the assembly 200 in the constricted state during insertion of the assembly 200 into the vasculature 52 and during movement of the assembly 200 within the vasculature 52. The sheath 281 can comprise any suitable material and may be of any suitable variety, such as those known in the art or yet to be devised. In some embodiments, the sheath 281 extends upwardly beyond the upper end of the graft 204 and/or extends downwardly beyond the lower end of the stent 202 to a greater extent than is shown in FIG. 6.

As can be appreciated from FIG. 6, in the illustrated embodiment, an upper portion of the sheath 281 contains the graft 204 and a lower portion of the sheath 281 contains the stent 202. As previously discussed, in the illustrated embodiment, there is no overlap between the graft 204 and the stent 202 when the assembly 200 is in the constricted state. Accordingly, for that portion of the sheath 281 that contains the assembly 200, a transverse cross-section through each point along a longitudinal axis defined by the sheath 281 intersects no more than one of the graft 204 and the stent 202. In FIGS. 6 and 6A, the longitudinal axis of the sheath 281 is not illustrated, but it is generally aligned with or coaxial with the guidewire 282, particularly in the small region shown in FIG. 6A.

As previously mentioned, however, other embodiments may include a region in which there is an overlap between the graft 204 and the stent 202. In particular, the overlap may be at an interface of the graft 204 and the stent 202. Such an overlap may represent only a very small portion of the longitudinal length of the assembly 200 when the assembly is in the constricted orientation. Stated otherwise, that portion of the sheath 281 that contains the stent 202 and the graft 204 (i.e., the occupied portion of the sheath 281) is primarily single-layered, at least with respect to the stent 202 and the graft 204. In various embodiments, a transverse cross-section through a longitudinal axis defined by the sheath intersects no more than one of the graft 204 and the stent 202 at each point along at least a majority of, or no less than 50, 60, 70, 80, 90, or 95 percent of, the portion of the longitudinal axis that extends between the upper and lower ends of the occupied portion of the sheath 281.

As previously mentioned, the assembly 200 can be relatively small, which can result from its generally non-overlapping arrangement. For example, in various embodiments, a maximum diameter of the sheath in which the assembly 200 is packaged can be no greater than about 6, 7, 8, 9, 10, 11, 12, 13, 14, 15, or 16 French.

The placement system 280 that is used to implant the assembly 200 can include additional features, such as guidewires 282, 284, an expansion balloon 285, and/or positioning lines 286, 288. The guidewires 282, 284 and the expansion balloon 285 can be of any suitable variety, such as those that are known in the art. The positioning lines 286, 288 also can take a variety of forms and, as discussed further below, can be configured to reposition, rearrange, reconfigure, and/or adjust the graft 204 relative to the stent 202 in situ.

Figure 10:
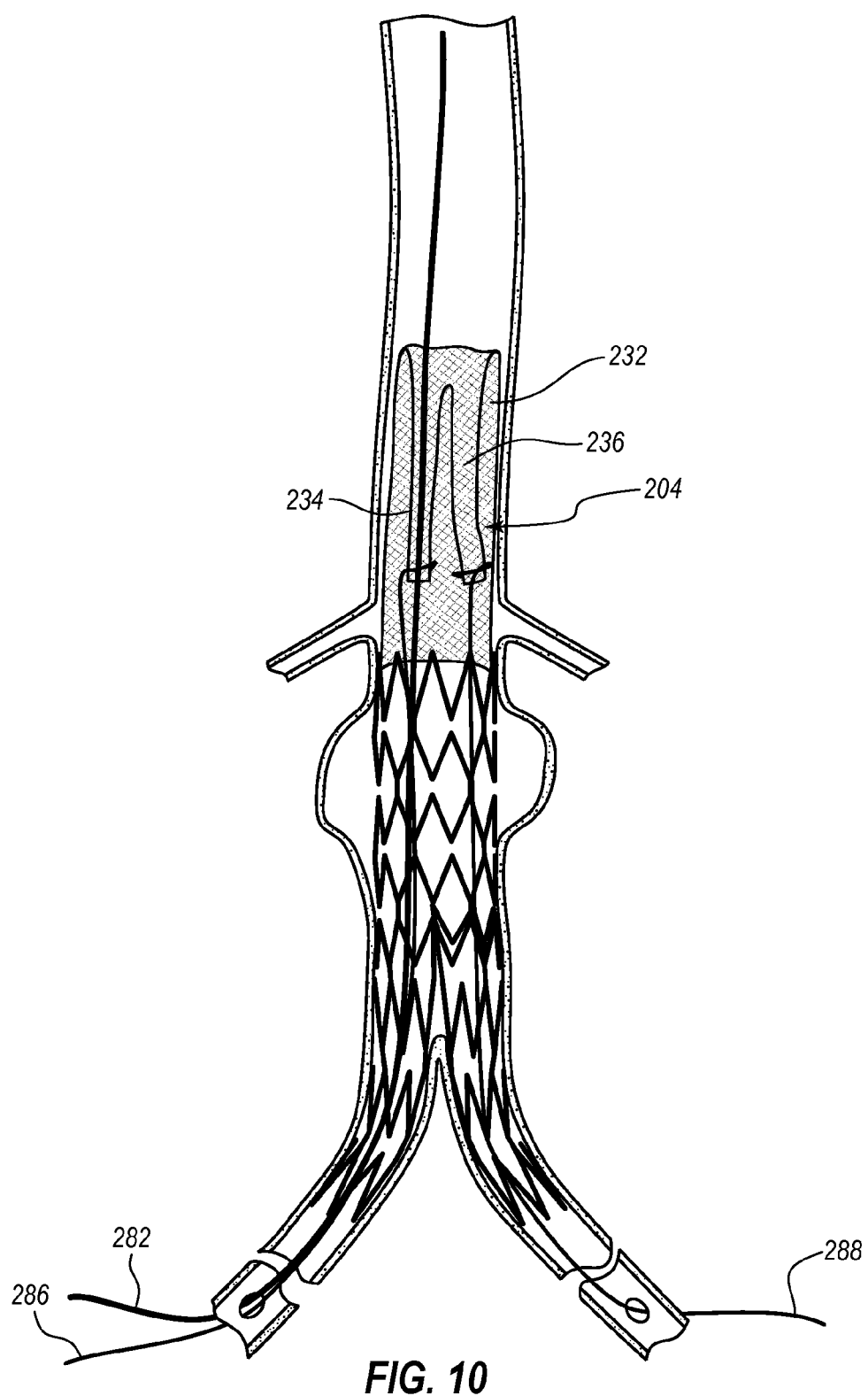

In the illustrated embodiment, the positioning lines 286, 288 comprise threads. As can be seen in FIGS. 9-10, the positioning line 286 can be attached to the right sleeve 234 of the graft 204 and the positioning line 288 can be attached to the left sleeve 236. In some embodiments, one or more of the positioning lines 286, 288 may comprise a radiopaque material (e.g., the radiopaque material may be woven into the lines or coated thereon), which can facilitate distinguishing of the lines 286, 288 from each other and/or manipulation of the lines 286, 288 in situ. As can be seen in FIG. 6, the positioning lines 286, 288 and the sleeves 234, 236 of the graft 204, respectively, can be coupled with each other prior to packaging of the assembly 200 in the sheath 281.

As discussed further below, in other embodiments, the positioning lines 286, 288 may not be prepackaged with the assembly 200, but may instead be coupled with the sleeves 234, 236 in situ. In still other embodiments, the placement system 280 may be devoid of positioning lines 286, 288, and other features may be used to reposition the graft 204 relative to the stent 202.

FIGS. 6-11 depict various stages of an illustrative method for endovascular implantation of the stent graft assembly 200. With reference in particular to FIG. 6, an artery in the right leg of the patient 50 may be accessed in any suitable method, such as via a standard cut-down technique. An opening 90 can be formed in a wall 53 of the artery and the guidewire 282 can be inserted therethrough. The guidewire 282 can be advanced through the vasculature 52 to a position that is slightly upstream of the position to which an upper end of the sheath 281 is to be advanced. The stent graft assembly 200, in its constricted and packaged state, can then be advanced over the guidewire 282, through the opening 90, and into the desired position within the vasculature 52. In some embodiments, at least a portion of the stent 202 and/or at least a portion of the graft 204 may be radiopaque such that the position of assembly 200 within the vasculature 52 may be monitored via standard techniques. The positioning lines 286, 288 may be sufficiently long such that when the assembly 200 has been advanced to the desired position, a portion of each line 286, 288 remains at an exterior of the vasculature 52 (i.e., is outside of the opening 90).

With reference to FIG. 7, once the stent graft assembly 200 is in the desired position, the sheath 281 can be retracted from the assembly 200 and removed through the opening 90. The graft 204 can comprise a fabric-like material, and may only slightly expand upon removal of the sheath 281. As previously discussed, in some embodiments, the stent 202 may not expand automatically, but may instead be expanded by a balloon using common techniques.

As can be appreciated from the foregoing, the assembly 200 can define a relatively small outer diameter when it is in the constricted state, and thus may be introduced into the vasculature 52 from a position that is relatively distant from the target site at which the assembly 200 is expanded. A standard percutaneous guidewire retraction procedure from such a position, rather than use of a standard cutdown technique that is closer to the target site (and thus may be more invasive) can reduce trauma to the patient.

However, in the illustrated embodiment, the stent 202 is self-expanding such that removal of the sheath 281 results in expansion of the stent 202. In the illustrated embodiment, an upper end of the trunk 222 of the stent 202 expands into contact and frictional engagement with the wall 53 of the aorta 54 at a position that is downstream from the right and left renal arteries 60, 62 and that is upstream from the abdominal aortic aneurysm 70. Automatic expansion of the upper end of the stent 202 can likewise expand the lower end of the graft 204.

Expansion of lower portions of the stent 202 can bring the bottom end of the trunk 222 into contact and frictional engagement with the wall 53 of the aorta 54 at a position that is downstream of the abdominal aortic aneurysm 70. The branch 224 of the stent 202 can contact and frictionally engage the right common iliac artery 58.

With continued reference to FIG. 7, an artery in the left leg may be accessed in any suitable method, such as via a standard cut-down technique or via a percutaneous guidewire retraction procedure. An opening 92 can be formed in a wall 53 of the artery and the guidewire 284 can be inserted therethrough. The guidewire 284 can be advanced through the vasculature 52 to a position at which an upper end of the branch 226 of the stent 202 is to be advanced. The branch 226 may be packaged within a second sheath (not shown) in a constricted state for insertion through the opening 92 and advancement through the vasculature 52.

Figure 8:
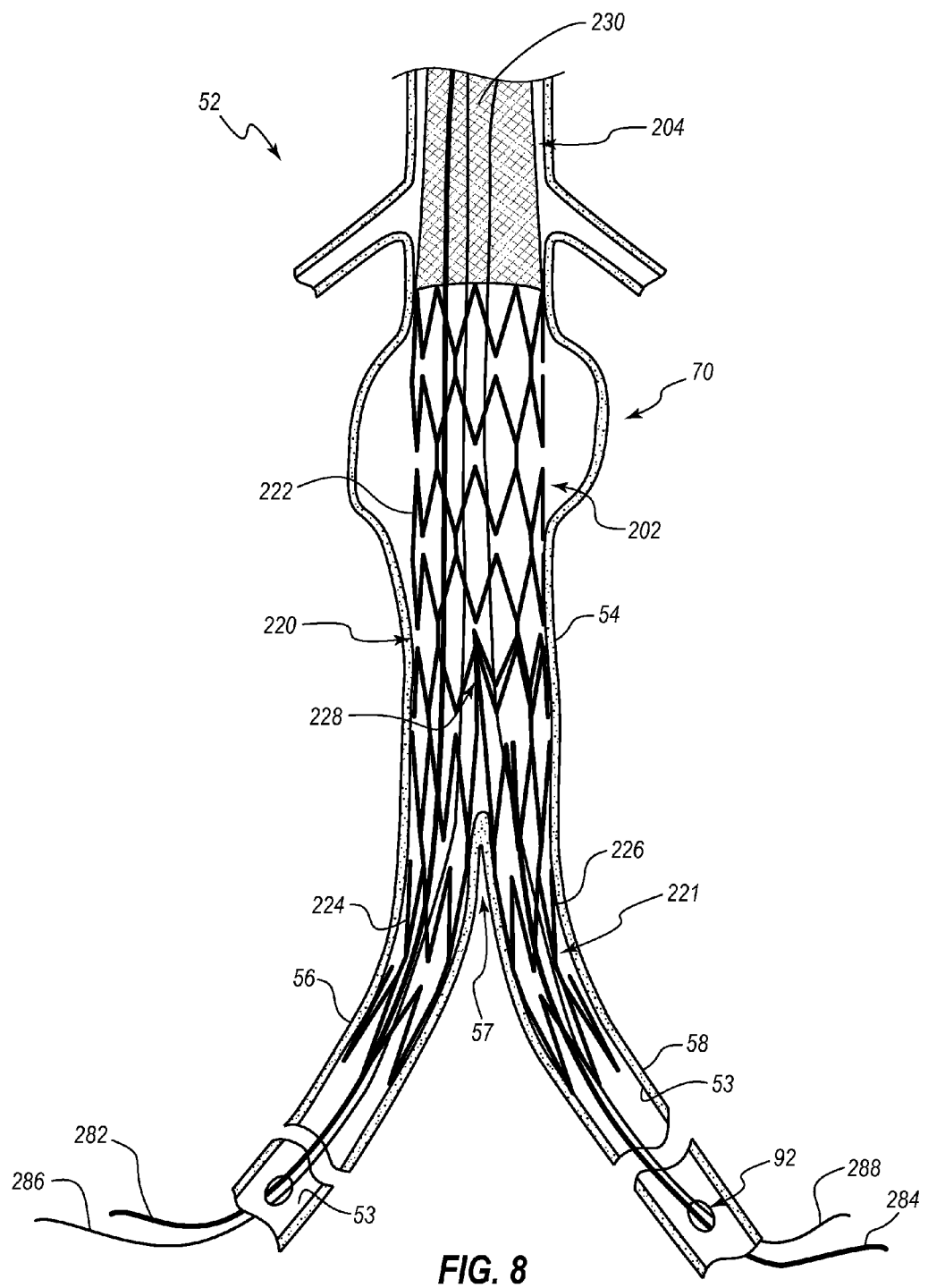

With reference to FIG. 8, the branch 226 may be advanced over the guidewire 284 to the desired position. The sheath (not shown) can be removed so as to permit the branch 226 to automatically expand into contact and frictional engagement with the wall 53 of the left common iliac artery 56.

Assembling separate branches 224, 226 of the assembly 200 in situ, and/or introducing the branches 224, 226 into the vasculature 52 via separate openings 90, 92, can result in less trauma to a patient. For example, the branch 226 of the stent 202, when in a packaged and constricted state, can define a relatively small outer diameter, and thus may be introduced into the vasculature 52 from a position that is relatively distant from the target site at which the assembly 200 is expanded. A standard percutaneous guidewire retraction procedure from such a position, rather than use of a standard cutdown technique that is closer to the target site (and thus may be more invasive) can reduce trauma to the patient.

Once the branch 226 is in place, any suitable technique may be used to capture the positioning line 288 so as to pull or otherwise move it through the opening 92 in the left artery. Care may be taken to ensure that the positioning line 288 (rather than the positioning line 286) is retrieved and to avoid tangling of the positioning lines 286, 288.

As previously mentioned, the graft 204 may not automatically expand. Accordingly, in some embodiments, the expansion balloon 285 may be used to separate portions of the wall 230 of the graft 204 from each other, particularly in the trunk 232 portion of the graft 204. The expansion balloon 285 can be advanced over the guidewire 282 and can be inflated using standard techniques known in the art. For example, the expansion balloon 285 may be configured to fluidly communicate with an inflation port 287 at an exterior of the patient 50.

With reference to FIG. 10, once the trunk 232 of the graft 204 has been opened, the positioning lines 286, 288 can be pulled so as to draw the sleeves 234, 236 downwardly through the trunk 232 and into the stent 202. This can invert the graft 204, or cause it to turn inside-out, relative to its original orientation. In some embodiments, the guidewire 282 may be left in place for this stage of the positioning procedure, and the sleeve 234 can be drawn downwardly over the guidewire 282.

Figure 11:
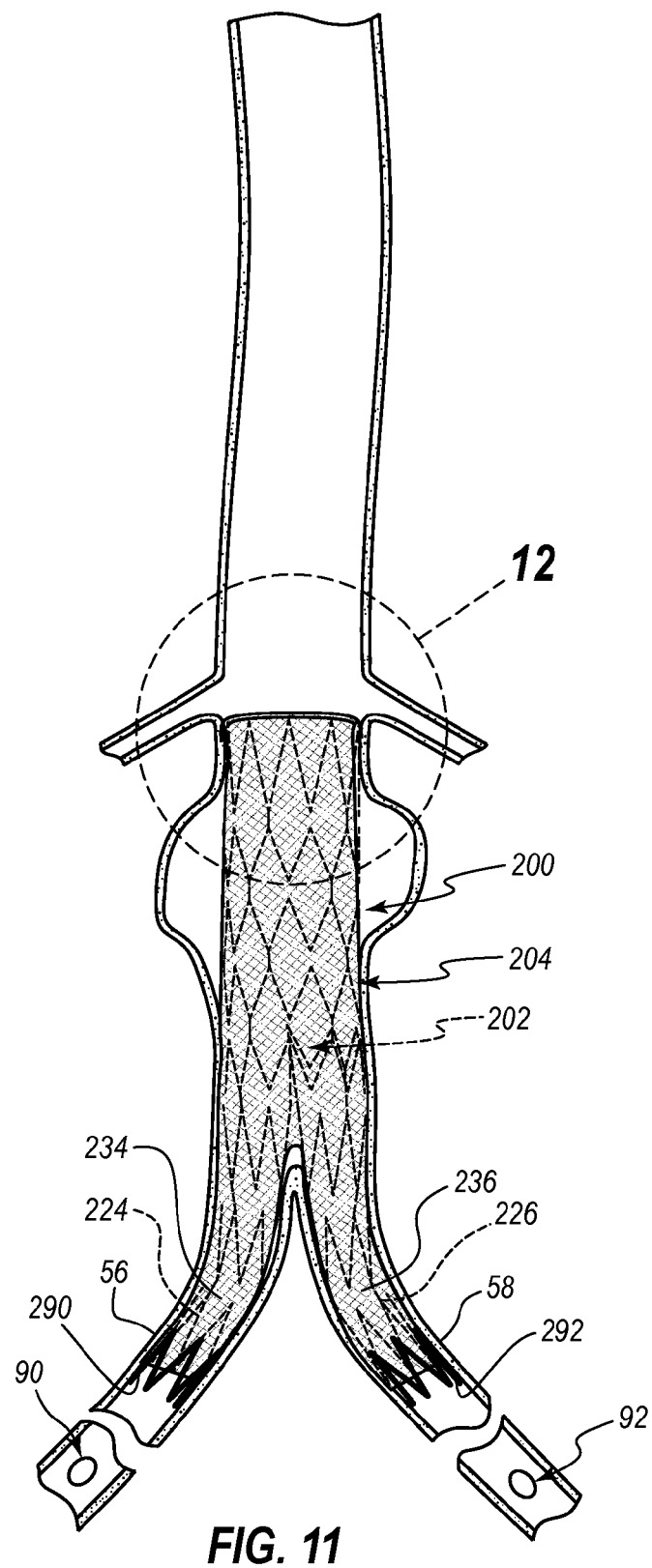
Figure 12:
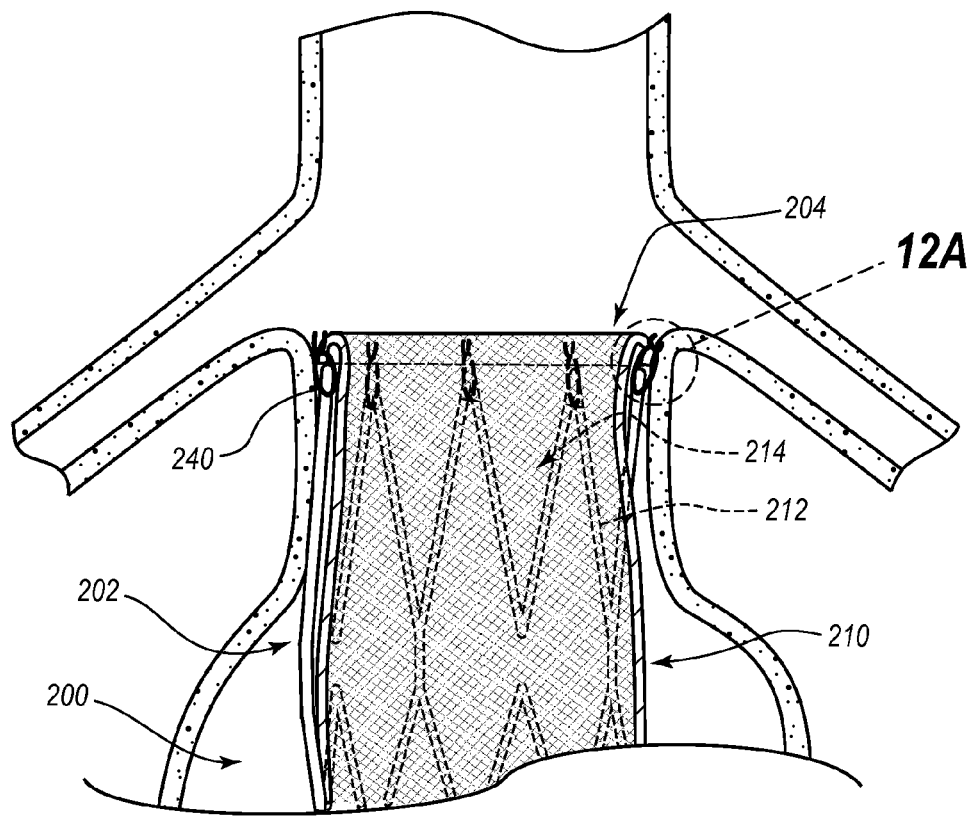
FIG. 12 is an enlarged partial cross-sectional view taken along the view line 12 in FIG. 11.
Figure 12A:
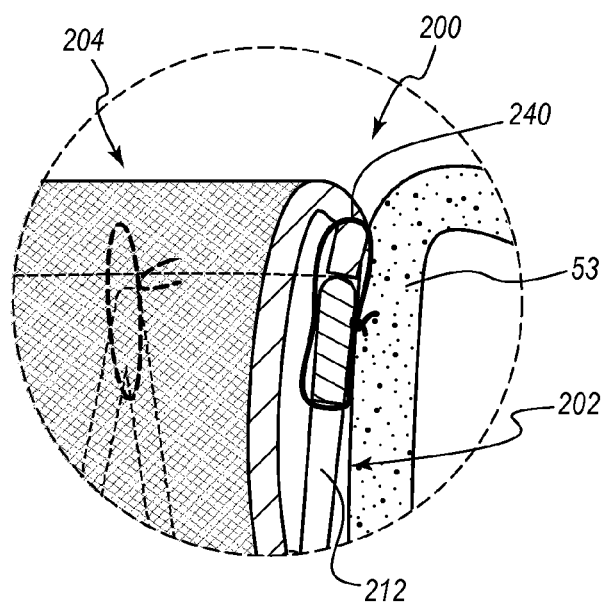
FIG. 12A is an enlarged partial cross-sectional view taken along the view line 12A in FIG. 12.

Repositioning of the trunk 232 in this manner can initially reduce the length of the non-overlapping region 279 (see FIG. 6). As seen in FIG. 11, in the illustrated embodiment, the non-overlapping region 279 is substantially eliminated once the graft 204 has been fully drawn into the stent 202, since the graft 204 and the stent 202 become coextensive substantially along a longitudinal length of the stent 202.

Expanding the trunk 232 via the expansion balloon 285, as shown in FIG. 9, can facilitate the drawing of sleeves 234, 236 into the stent 220, as shown in FIG. 10. However, in some instances, the expansion balloon 285 may not be used. For example, in some embodiments, the upper end of the self-expanding stent 202 may separate the bottom end of the graft 204, through which the sleeves 234, 236 may be pulled without first separately expanding the trunk 232.

Additionally, as previously mentioned, in some embodiments, the positioning lines 286, 288 may not be attached to the sleeves 234, 236 prior to insertion of the assembly 200, but may instead be attached in situ. For example, once the trunk 232 has been expanded and the expansion balloon 285 removed from the vasculature 52, the positioning line 286 may be advanced through the opening 90, through the stent 202, through the graft 204, and attached to the sleeve 234, such as by suturing or any other suitable method. Similarly, the positioning line 288 may be advanced through the opening 92, through the stent 202, through the graft 204, and attached to the sleeve 236. In other embodiments, the placement system 280 may be devoid of positioning lines 286, 288, and other features may be used to reposition the graft 204 relative to the stent 202. For example, separate wires (not shown) having catching or grasping features, such as hooked ends, may be advanced through the openings 90, 92 and through the graft 204, and may be used to engage the upper ends of the sleeves 234, 236.

With reference to FIG. 11, once the sleeves 234, 236 have been pulled into the branches 224, 226 of the stent 202, in some embodiments, the sleeves 234, 236 may be anchored in place at a lower end of the assembly 200. In the illustrated embodiment, a separate anchor 290, 292 is placed at the interior of each sleeve 234, 236. The anchors 290, 292 can comprise any suitable arrangement. For example, the anchors 290, 292 can comprise smaller stents, which may be self-expanding or balloon expandable. Any suitable method may be used to position the anchors 290, 292. For example, in the illustrated embodiment, the anchor 290 is self-expanding and can be originally restrained in a sheath (not shown), advanced over the guidewire 282 (FIG. 10) to the desired position, and released from the sheath once in place. Once the implantation procedure is complete, the surgical site can be closed in any suitable manner.

The implanted assembly 200 can provide a fluid path through the abdominal aortic aneurysm 70. As previously mentioned, a portion of the stent 202 that spans the abdominal aortic aneurysm 70 can be self-supporting, and blood flowing through the graft 204 can press the graft 204 outwardly against the stent 202. The stent 202 thus can restrain the graft 204 from expanding significantly beyond or past the framework of the stent 202. An exterior surface of the graft 204 thus can generally conform to the shape defined by an interior surface of the stent 202. In some embodiments, the links 212 and the interstices 214 of the stent 202 are sized and shaped so as to prevent undue strain on the graft 204 under such conditions, as the pressure tends to urge portions of the graft 204 through the interstices. A thickness of the graft 204 can also be adjusted in view of the same considerations. Various geometries of the links 212 and the interstices 214 and/or various constructions of the graft 204 can allow for thin-walled stents 202 and thin-walled grafts 204, which can reduce the overall profile of the packaged form of the assembly 200.

FIGS. 13-20 illustrate another embodiment of a stent graft assembly 300 that includes a stent 302 and a graft 304 that are configured to be separately inserted into the vasculature 52 of the patient 50 and coupled with each other in situ. When the assembly 300 is in a pre-use or packaged state prior to implantation, the stent 302 and the graft 304 can be contained in separate sheaths. In particular, when it is in the constricted state, the stent 302 can be contained within a sheath 381. Similarly, when it is in the constricted state, the graft 304 can be contained in a separate sheath (not shown). Such an arrangement can permit relatively small packaging for the sheaths, as neither sheath includes any portion in which the bulk of the stent 302 and the bulk of the graft 304 are additive. Stated otherwise, the stent 302 and the graft 304 do not overlap each other prior to their insertion into the vasculature 52. Accordingly, a composite non-overlapping region can be defined as both the region that extends between the longitudinal ends of the stent 302 when in the stent 302 is in the constricted state, as well as the region that extends between the longitudinal ends of the graft 302 when the graft 304 is in the constricted state.

Figure 14:
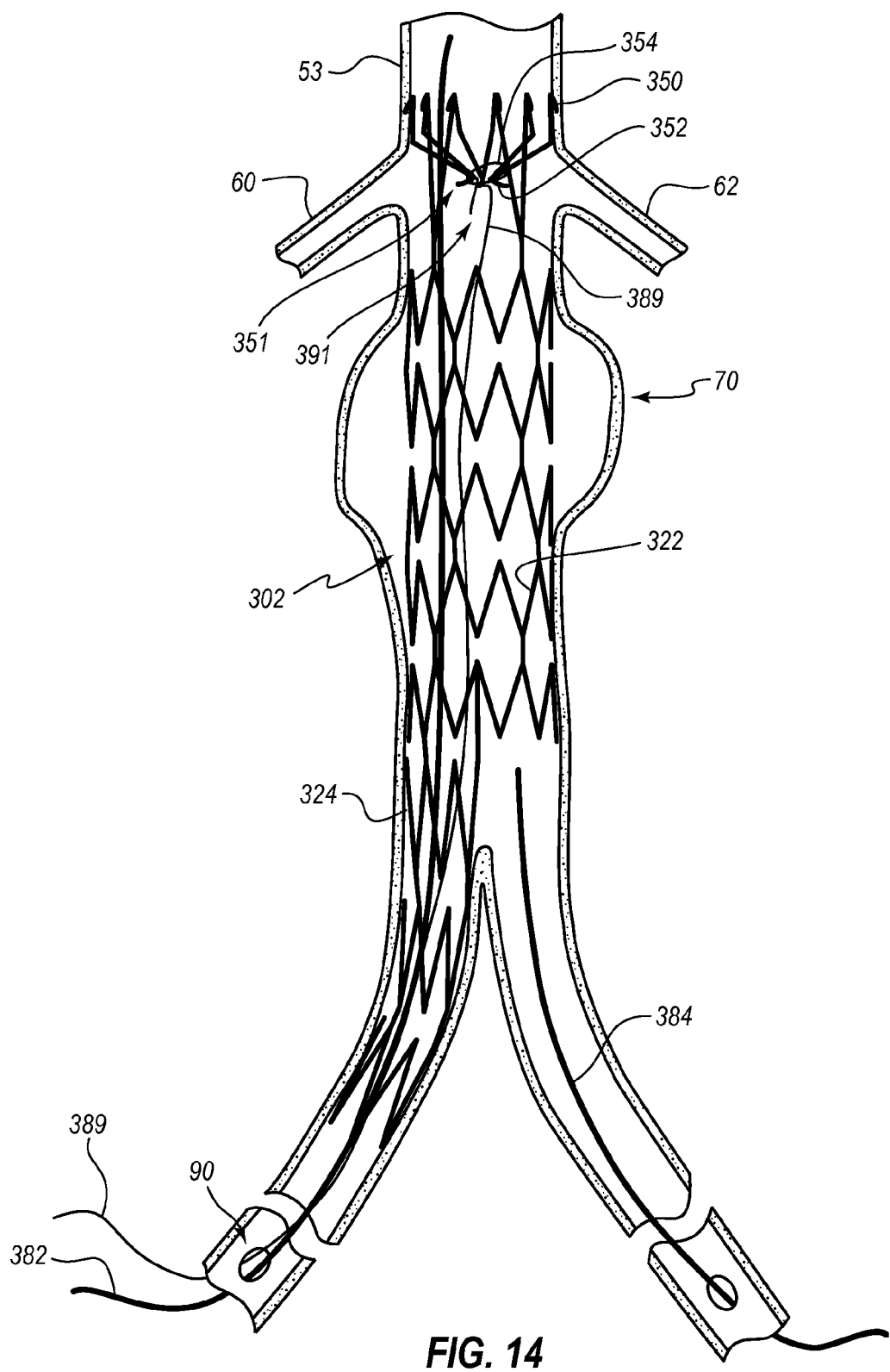
Figure 20:
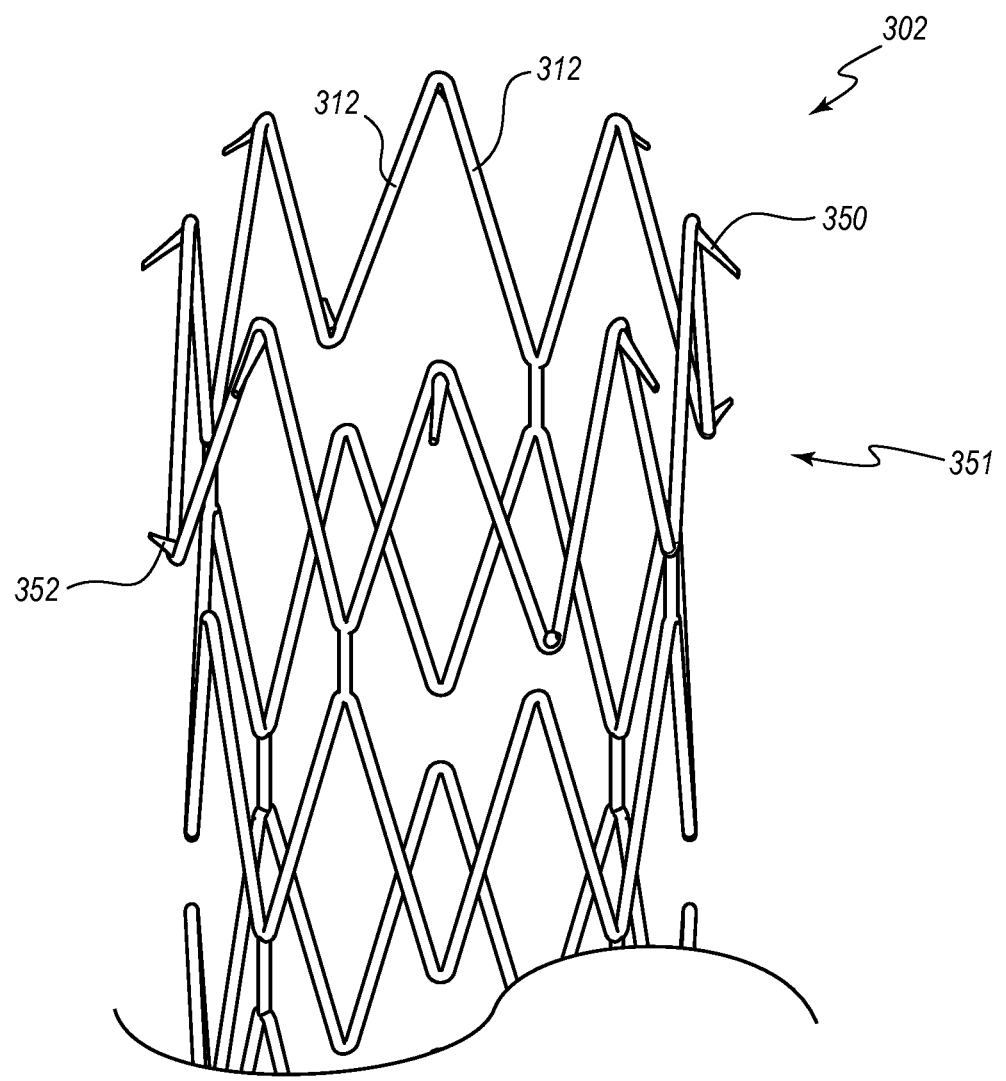
FIG. 20 is a partial perspective view of an upper end of an embodiment of a stent that is compatible with the stent graft assembly in FIGS. 13-19.

With reference to FIGS. 14 and 20, the stent 302 can include a plurality of outwardly directed upper projections, barbs, snares, spikes, or hooks 350 that are configured to be inserted into the vessel wall 53 so as to securely fasten the stent 302 thereto. The stent 302 can further include a connection interface 351 that is configured to connect the stent 302 to the graft 304 in situ. The connection interface 351 includes a plurality of outwardly directed lower projections, snares, spikes, or hooks 352 that are configured to engage the graft 304, as further discussed below. The upper hooks 350 are positioned at upper ends of adjacent links 312 at the upper end of the stent 302, whereas the lower hooks 352 are positioned at lower ends of an alternate combination of the adjacent links 312 that are at the upper end of the stent 302. In particular, each hook 352 is positioned at a lower end of a set of links 312 that are configured to operate substantially as a hinge.

When the stent 302 is packaged in a pre-use state, a retainer, restraint, or constraint 354, such as a ring of wire or thread, is looped about the lower ends of the hinged links 312 at a position that is above the hooks 352. Accordingly, when the stent 302 self-expands once it is released from the sheath 381, as shown in FIG. 14, the lower hooks 352 are held in close proximity to each other via the constraint 354, as discussed further below.

Figure 13:
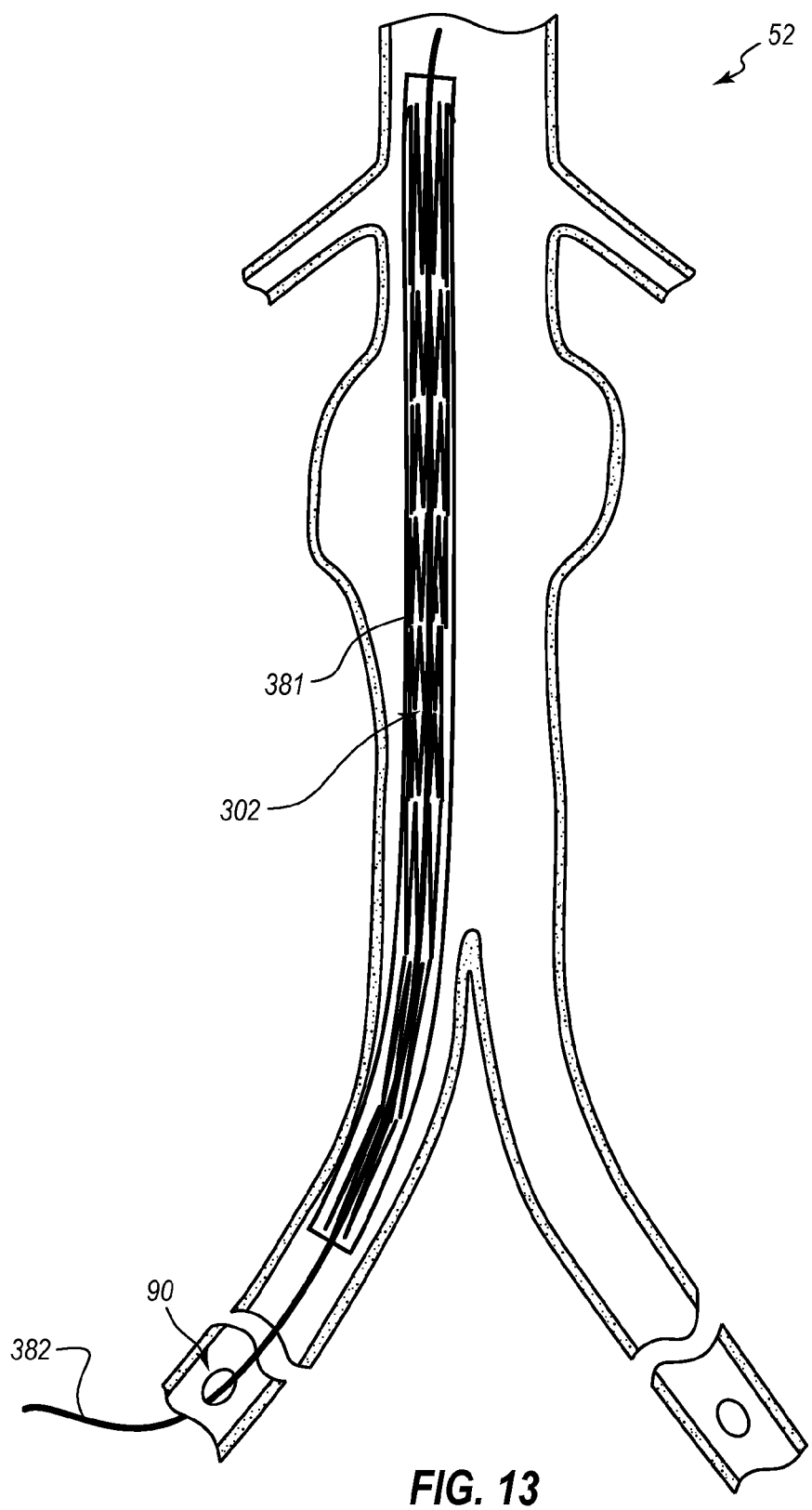
FIGS. 13-19 are cross-sectional views of various stages of another illustrative procedure for implanting another embodiment of a stent graft assembly in the vasculature of a patient.

FIGS. 13-19 depict various stages of an illustrative method for endovascular implantation of the stent graft assembly 300. As shown in FIG. 13, the stent 302, which is packaged in the sheath 381, can be advanced through the opening 90 into the vasculature 52 over a guidewire 382.

With reference to FIG. 14, once the stent 302 is in the desired position, the sheath 381 can be removed and retracted through the opening 90, which can allow the stent 302 to self-expand into contact with vessel wall 53. Much of the stent 302 can frictionally engage portions of the vessel wall 53 to secure the stent 302 in place. Moreover, the upper hooks 350 can embed within the vessel wall 53 to provide an additional level of secure attachment thereto. In the illustrated embodiment, the hooks 350 are embedded in the wall 53 at a position above the renal arteries 60, 62, although other arrangements are possible. For example, in some instances, the upper hooks 350, as well as the remainder of the upper end of the stent 302, can instead be placed below the renal arteries 60, 62.

Upon expansion of the stent 302, the lower hooks 352 may remain in close proximity to each other due to the constraint 354. At the illustrated stage of the procedure, a constraint removal device 389, such as a wire having a hooked end 391, has been advanced into engagement with the constraint 354 for use at a later stage of the procedure. Any suitable device may be used in the eventual disengagement and/or removal of the constraint 354.

Figure 15:
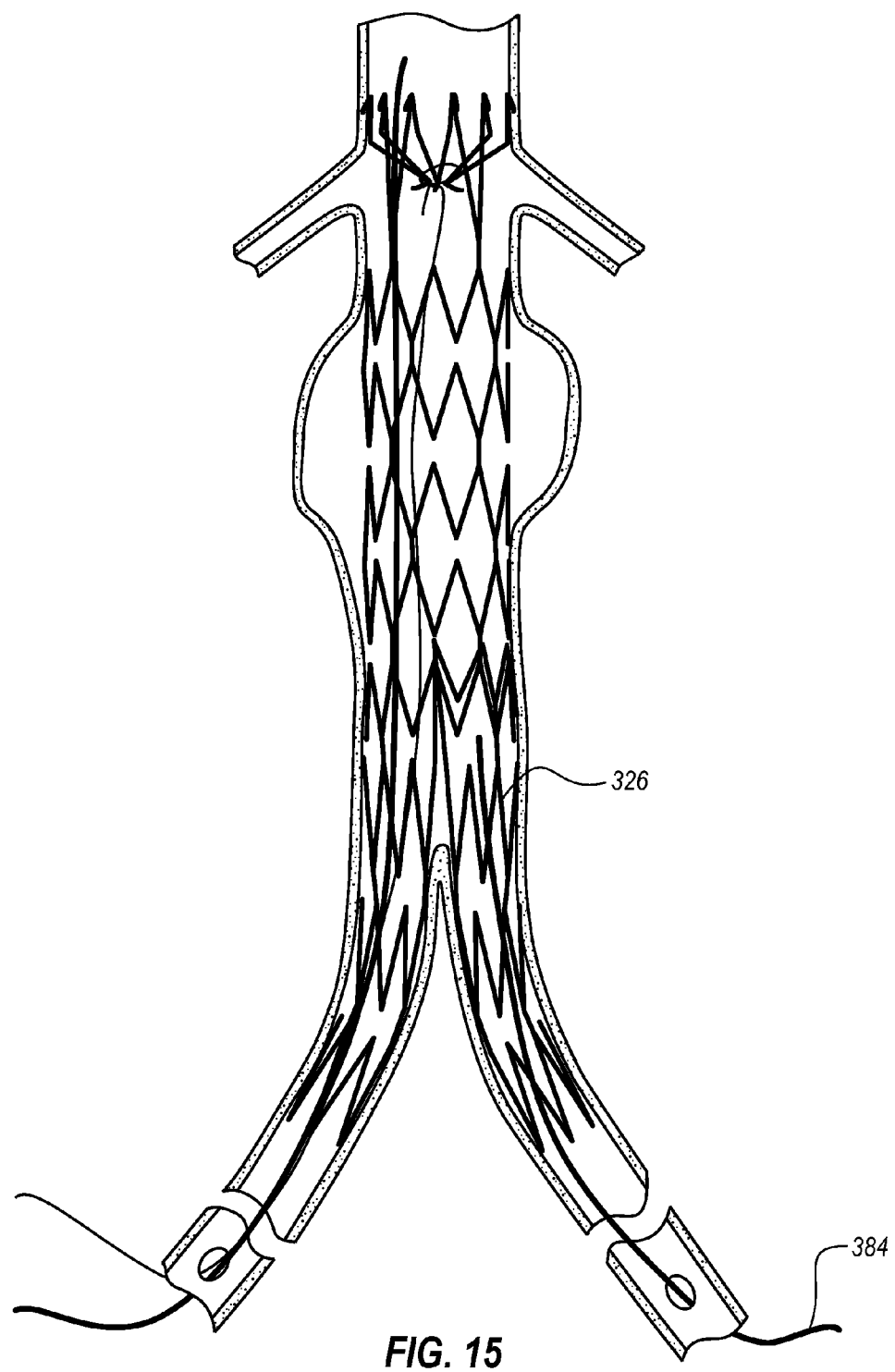

As shown in FIGS. 14 and 15, the stent 302 can include a trunk 322 and two legs 324, 326. A guidewire 384 may be inserted into a different branch of the vascular system for placement of the separate leg 326 in a manner such as described above.

Figure 16:
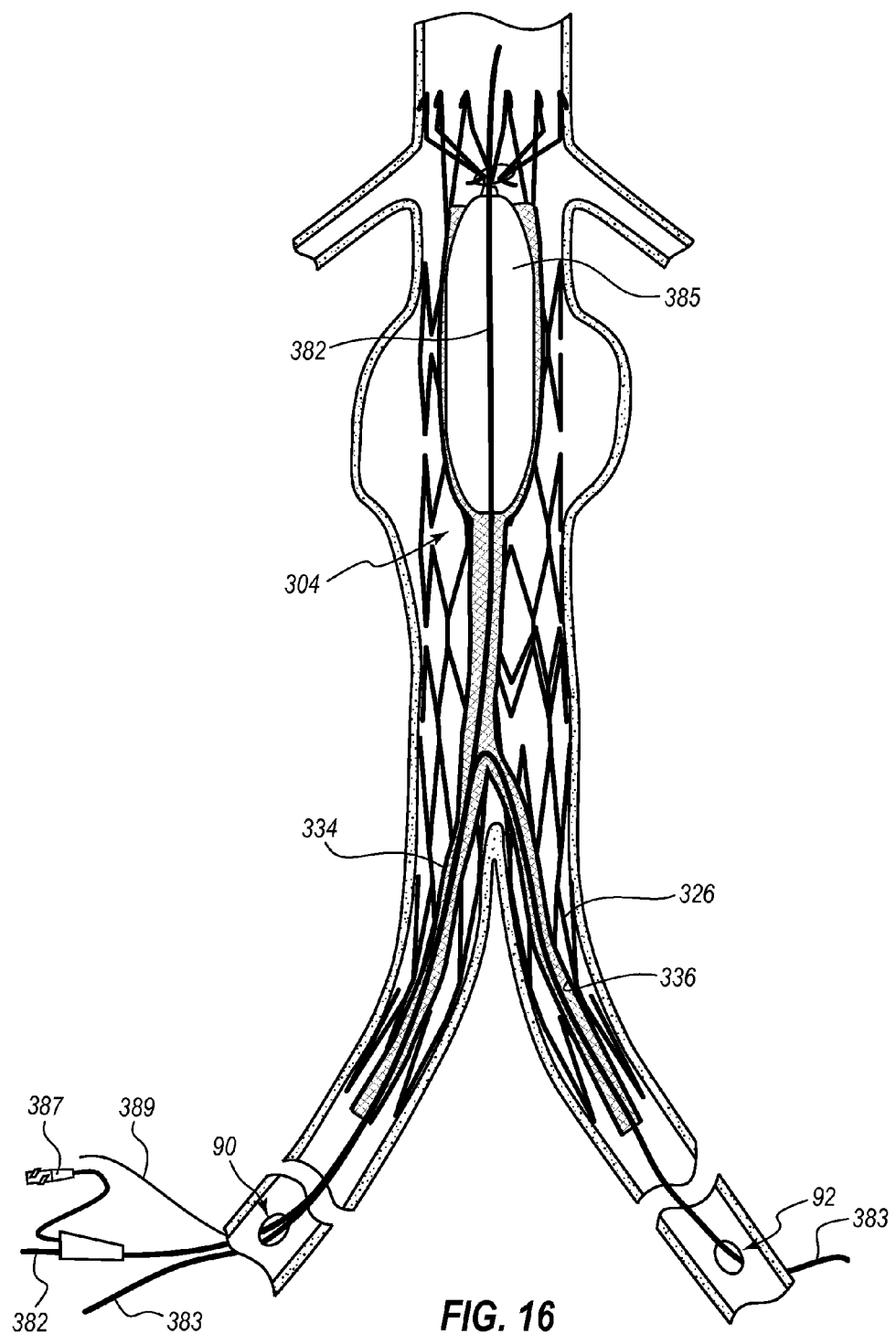

With reference to FIG. 16, the graft 304 may be housed in a sheath (not shown) for insertion through the opening 90 into the vasculature 52. The sheath can be advanced over the guidewire 382 into an interior of the stent 302 to a desired longitudinal position, and the sheath can then be removed. An upper end of the graft 304 can desirably be positioned below the renal arteries 60, 62. In some embodiments, a separate line or wire 383 may either be packaged with the graft 304 or inserted into the graft 304 after it has been positioned as desired. The wire 383 may extend through both branches 334, 336 of the graft 304, and can be used to move one of the branches 336 into the leg 326 of the stent 302.

For example, in some embodiments, the wire 383 is prepackaged with the graft 304 such that a portion thereof is within the branch 336 when the graft 304 is within a sheath. Another portion of the graft 304 remains outside of the patient once the graft 304 has been positioned, as shown. A separate device, such as a hook or other retrieval mechanism, can be inserted through the opening 92 in a separate artery so as to retrieve the end of the wire 383, which may be pulled through the opening 92.

Figure 17:
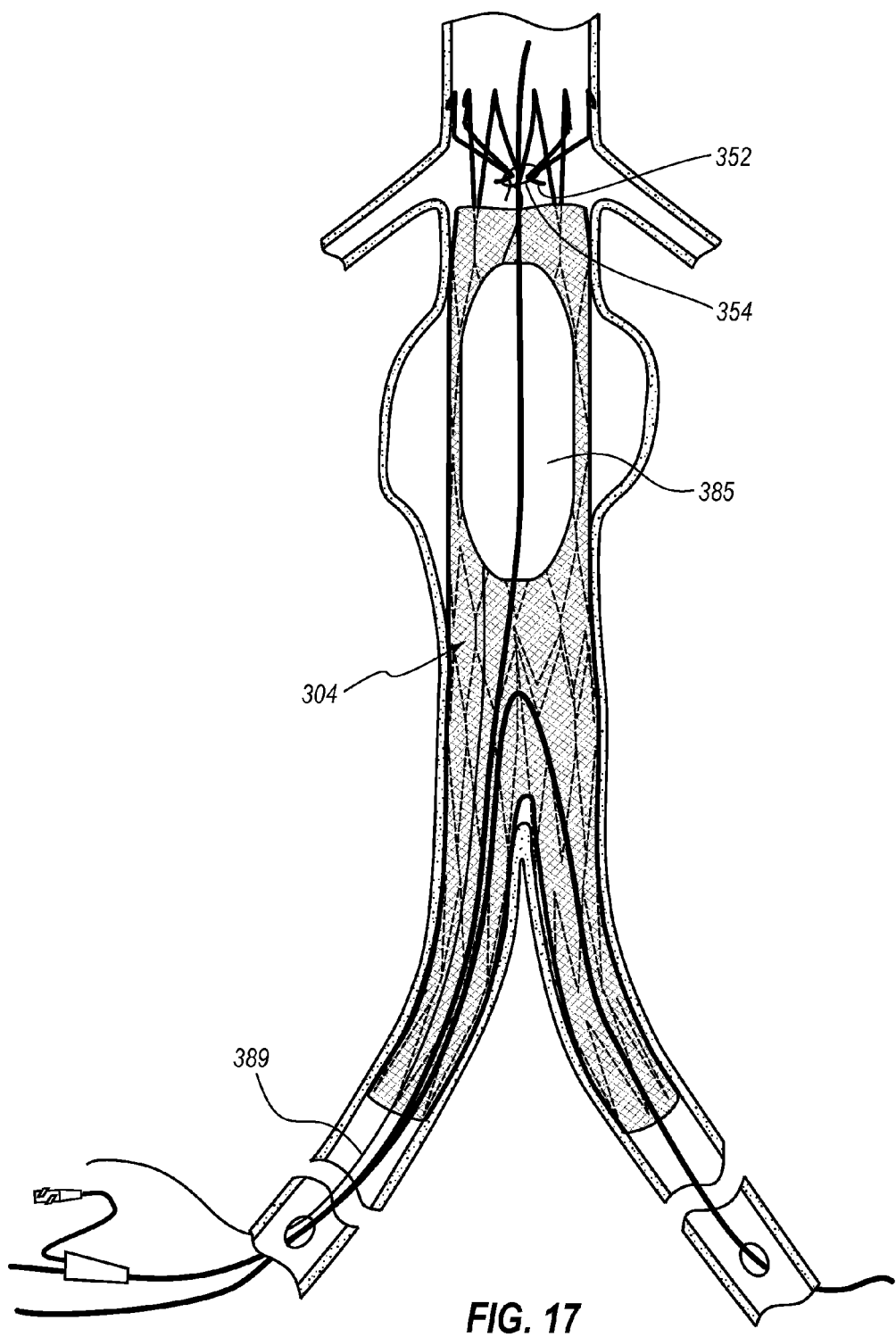

As shown in FIGS. 16 and 17, an expansion balloon 385 can be advanced over the guidewire 382 and inflated via a port 387 so as to move the graft 304 to an expanded state. In some embodiments, a balloon can also be advanced over the guidewire 383 so as to expand the branch 336 of the graft 304. In the illustrated method, once the graft 304 has been inflated as desired, the balloon 385 can be moved downwardly so as to provide clearance for the lower hooks 352 when the constraint 354 is removed from the stent 302 by the removal device 389. The hinged portions of the stent 302 can be biased outwardly such that when the constraint 354 is removed, the lower hooks 352 expand outwardly toward the vessel wall 53.

Figure 18:
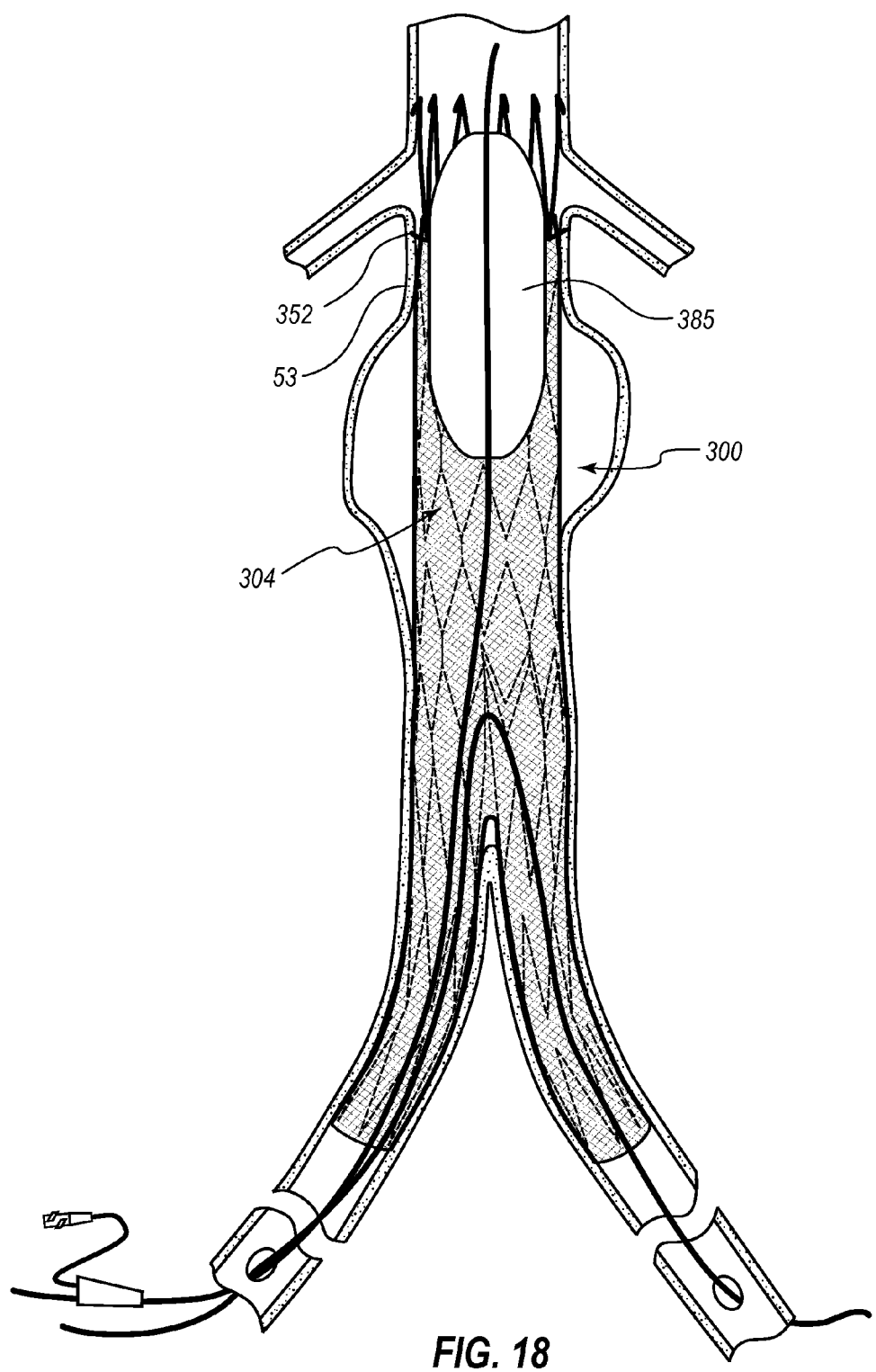

FIG. 18 illustrates that the balloon 385 can be used to assist in pressing the lower hooks 352 through the graft 304 and into the wall 53. The lower hooks 352 thus can directly connect the graft 304 and the stent 302 portions of the assembly 300 to each other. After connection has been achieved, the balloon 385 can be removed.

Figure 19:
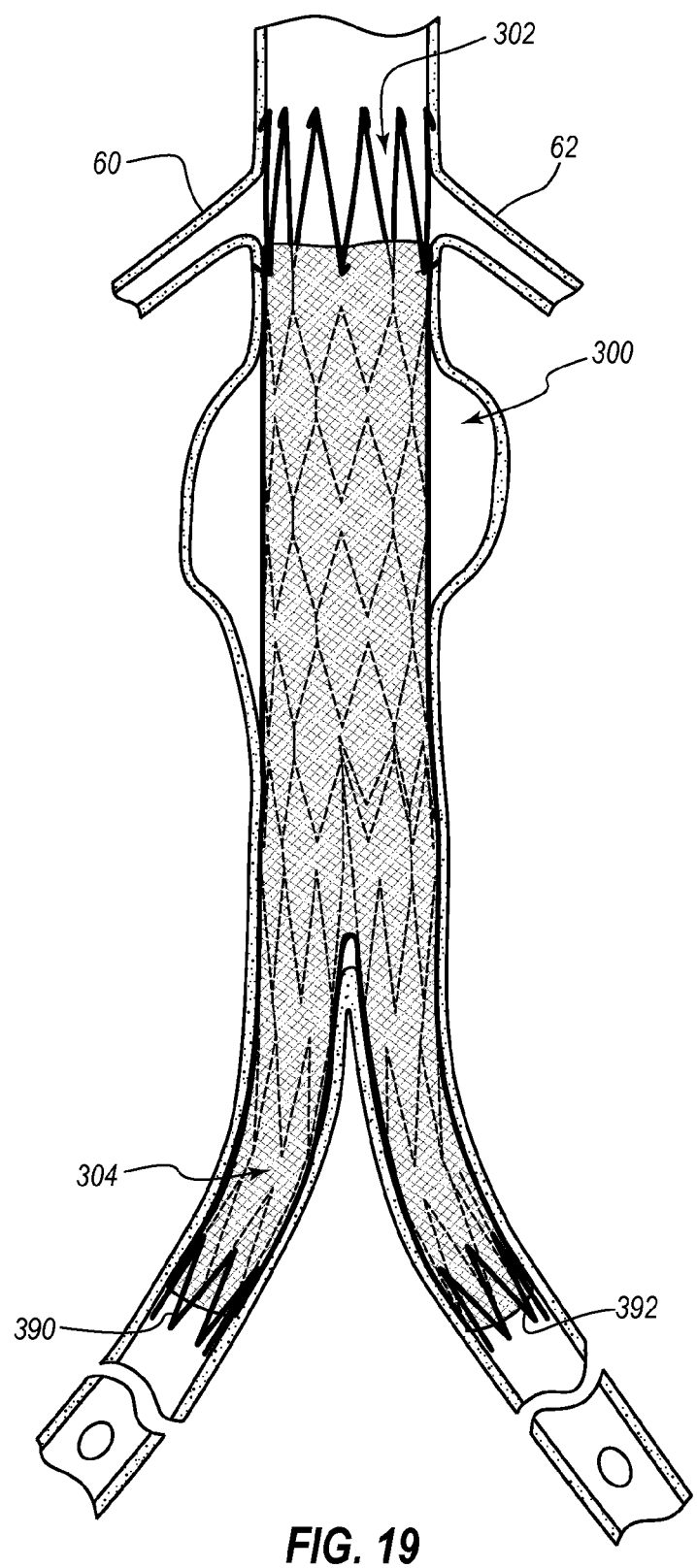

As shown in FIG. 19, in some embodiments, the lower ends of the graft 304 also can be held in place by secondary stents or anchors 390, 392 in any suitable manner, such as those described above with respect to the anchors 290, 292. As can also be seen in FIG. 19, in some embodiments, a bare or exposed portion of the upper end of the stent 302 can span the renal arteries 60, 62 for an implanted assembly 300.

Figure 21:
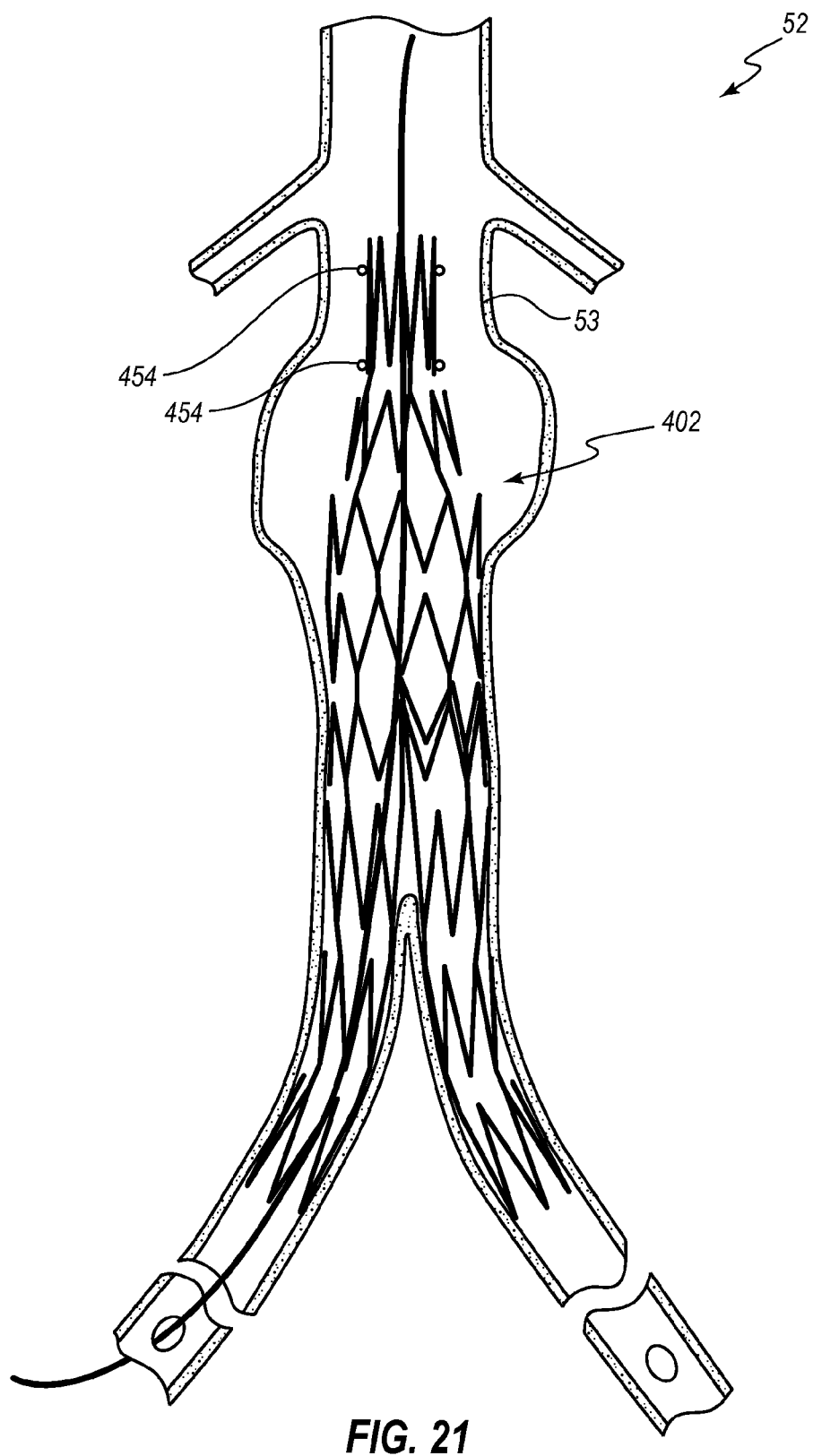
FIG. 21 is a cross-sectional view of a stage of an illustrative procedure for implanting another embodiment of a stent graft assembly.

FIGS. 21-27 depict various stages of another illustrative method for endovascular placement of another embodiment of a stent graft assembly 400. As shown in FIG. 21, an upper end of a stent 402 portion of the assembly 400 can include one or more constraints 454. The constraints 454 may be similar to the constraint 354 discussed above. For example, the constraints 454 may comprise rings of any suitable material. The constraints 454 may be slack when the stent 402 is in a packaged configuration. As the stent 402 is allowed to self-expand, the constraints 454 may become taut and prevent further expansion of the stent 402. Accordingly, the constraints 454 can allow the upper end of the stent 402 to expand somewhat relative to its initial constrained orientation so as to enlarge a passageway through the upper end of the stent 402, but can prevent the upper end of the stent 402 from fully expanding into contact with the vessel wall 53.

Figure 22:
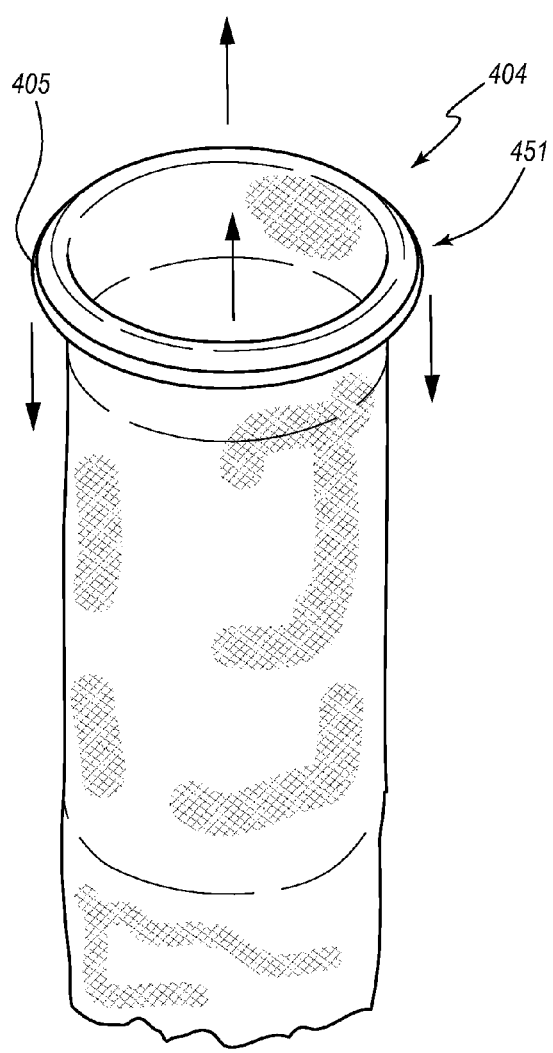
FIG. 22 is a partial perspective view of an embodiment of a graft that is compatible with the stent graft assembly of FIG. 21, wherein the graft is shown in a an unfolded or uncompressed state.
Figure 23:
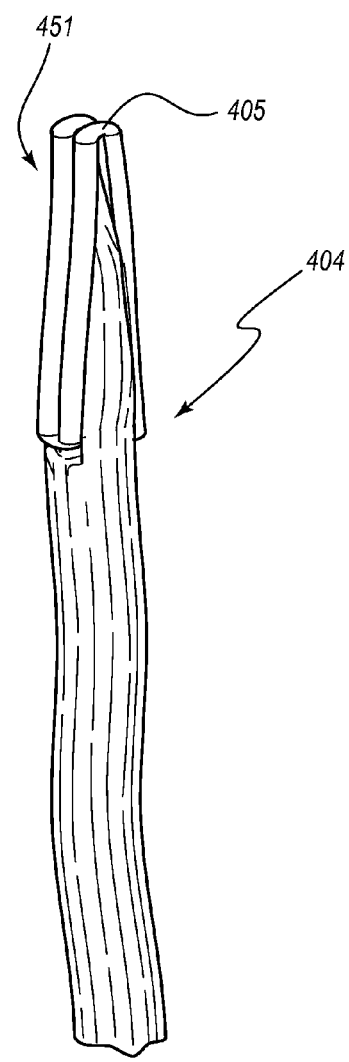
FIG. 23 is a partial perspective view of the graft of FIG. 22 that is shown in a folded or compressed state.
Figure 24:
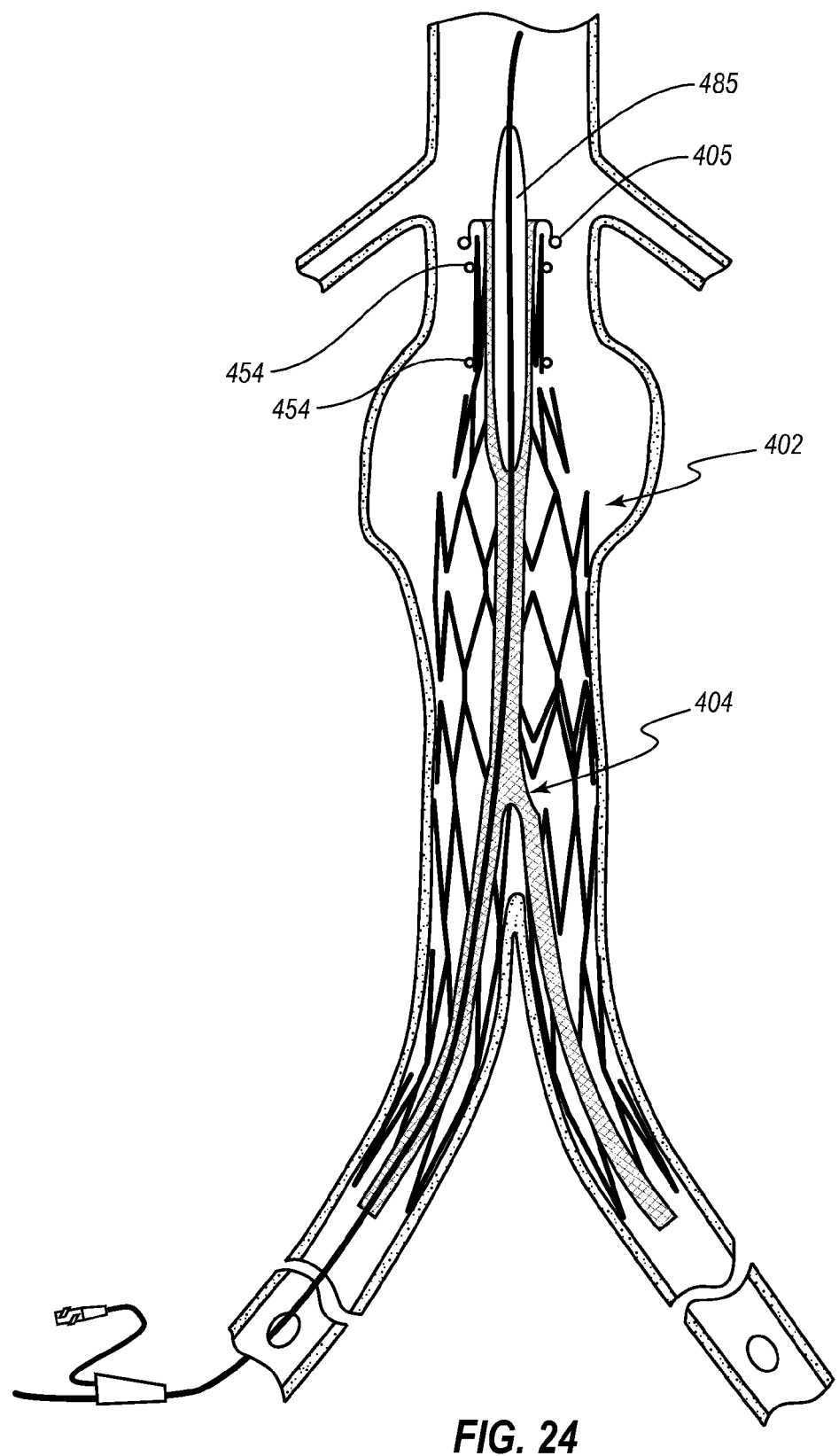
FIGS. 24-26 are cross-sectional views of additional stages of the procedure of FIG. 21.

With reference to FIGS. 22-24, a graft 404 can be configured for insertion into the stent 402 after the stent 402 has been positioned as desired within the vasculature 52. As shown in FIG. 22, the graft 404 can include a connection interface 451 at an upper end thereof by which the graft 404 can be connected to the stent 402 in situ. The connection interface 451 comprises a rim or ring 405 that extends radially outwardly relative to a remainder of the graft 404 when the graft 404 is in a natural or relaxed position. In some embodiments, the ring 405 comprises a resilient material such that the ring 405 is biased toward the natural or relaxed position. Accordingly, the ring 405 may be configured to return to the relaxed position shown in FIG. 22 after having been deformed relative thereto (e.g., urged into a configuration such as that shown in FIG. 23).

As indicated by the arrows in FIG. 22, the ring 451 can be folded into the constricted configuration of FIG. 23 for insertion into the vasculature 52. As shown in FIG. 24, when in the constricted configuration, the ring 451 can be advanced through the constricted upper end of the stent 402 such that when a sheath (not shown) is removed from the graft 404, the ring 451 is permitted to return to its natural orientation and expand outwardly and radially beyond the constricted upper end of the stent 402. The graft 404 may then be retracted downwardly somewhat so as to bring the ring 405 below an upper end of the stent 402, as shown in FIG. 24. Thereafter, both the upper end of the stent 402 and the upper end of the graft 404 can be expanded by an expansion balloon 485. Such expansion can burst the constraints 454 from the upper end of the stent 402 (or the constraints 454 may be removed in any other suitable fashion), thereby allowing the upper end of the stent 402 to expand outwardly toward the vessel wall 53.

Figure 25:
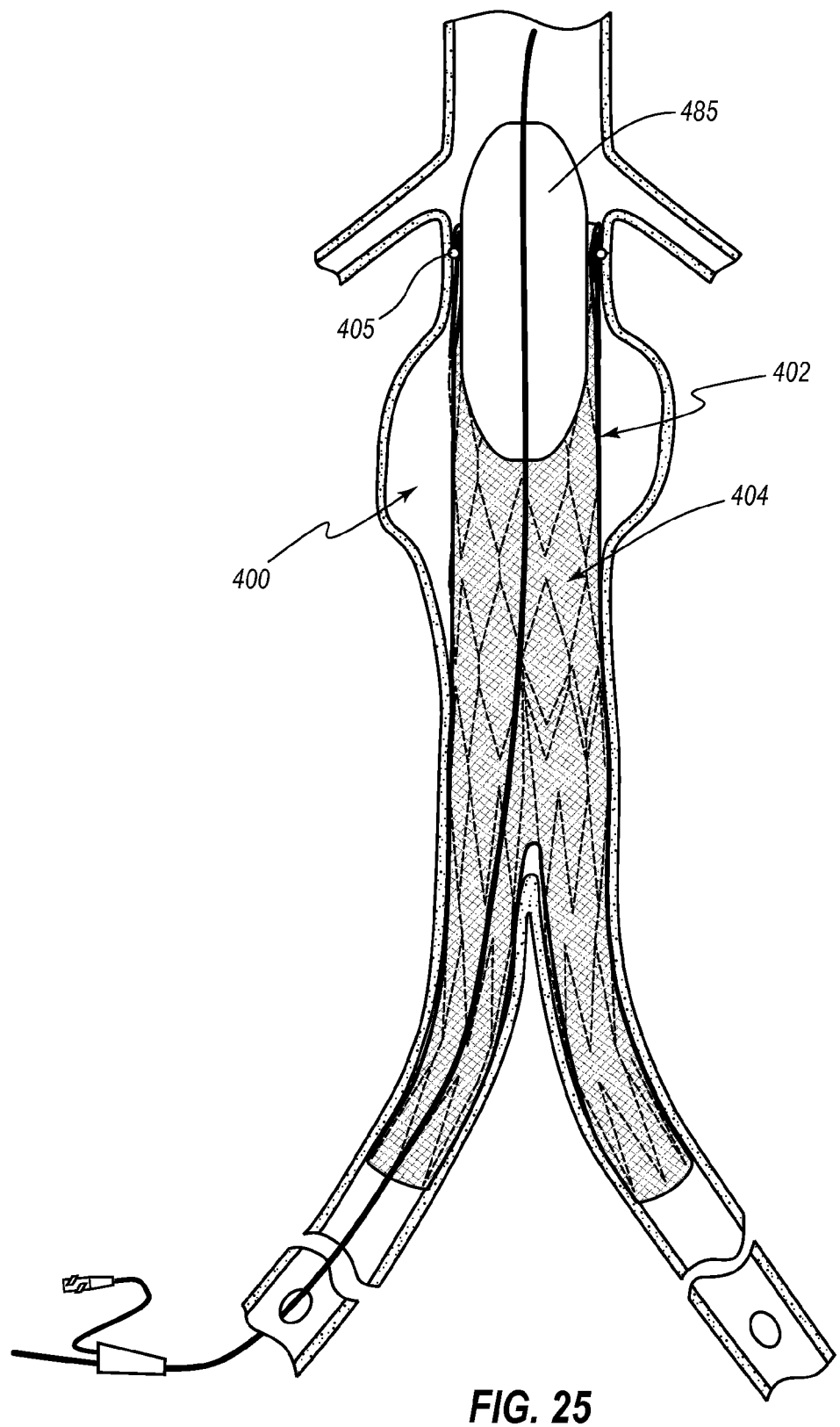
Figure 26:
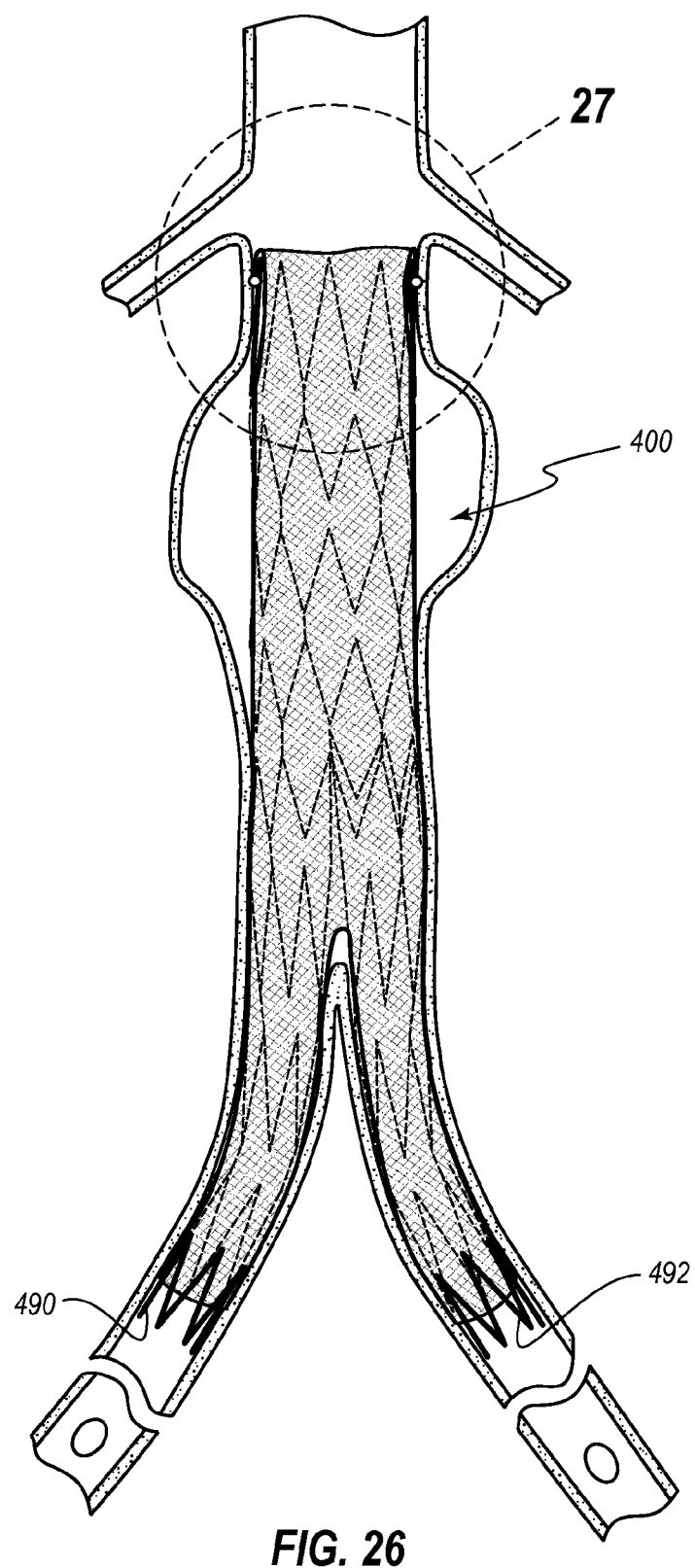
Figure 27:
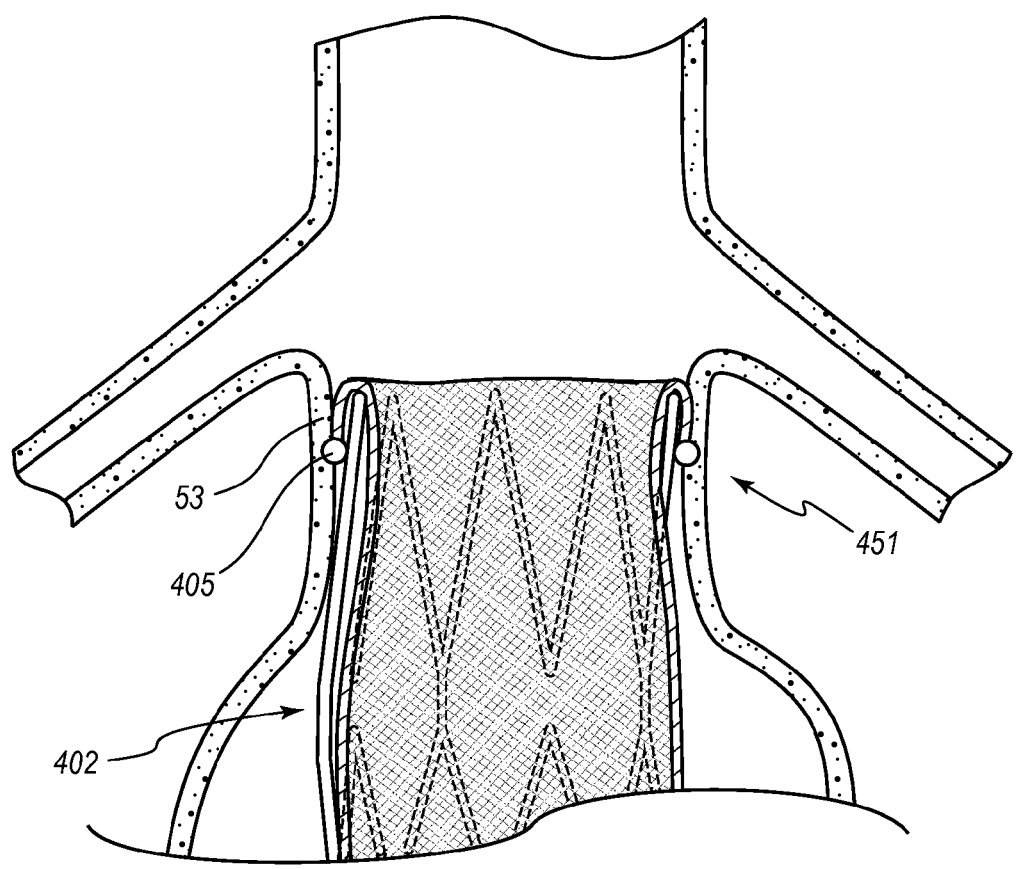
FIG. 27 is an enlarged partial cross-sectional view taken along the view line 27 in FIG. 26.

As shown in FIGS. 25-27, the ring 405 can be forced outwardly into contact with the vessel wall 53, and may form a fluid-tight, or substantially fluid-tight seal therewith. An upper end of the graft 404 can extend over an upper end of the stent 402. Where a wall of the graft 404 is also fluid tight, such an arrangement can provide for a fluid-tight connection between the vessel wall 53 and the graft 404 that substantially prevents contact between blood flowing into a lumen of the graft 404 and the upper end of the stent 402.

In other embodiments, which are not specifically shown in the drawings, an upper end of the stent 402 may have outwardly projecting hooks, such as the hooks 352 described above. The hooks may be configured to cooperate with the ring 405, and may also be considered as part of the connection interface 451 of the assembly 400. The ring 405 may be positioned below the hooks at the procedural stage shown in FIG. 20. As the upper end of the graft 404 and the stent 402 are expanded, the ring 405 can settle beneath the outwardly projecting hooks, which can aid in ensuring that the ring 405 remains disposed at an exterior of the stent 402 as the assembly 400 is expanded into contact with the vessel wall 53 (e.g., in the manner shown in FIGS. 24 and 25). Moreover, as the assembly 400 is expanded, the hooks 352 can pierce through the graft 404 at a position above the ring 405 and can embed within the vessel wall 53. Such an arrangement can provide additional connection mechanisms between the stent 402 and the graft 404.

As shown in FIG. 26, it may be desirable to position supplemental stents 490, 492 within the bottom branches of the graft 404. This can ensure that the graft 404 remains open throughout an entirety thereof. In some instances, however, blood flow through the graft 404 may be sufficient to permit the graft 404 to remain open and pressed against the stent 402 without such supplemental stenting.

Figure 28:
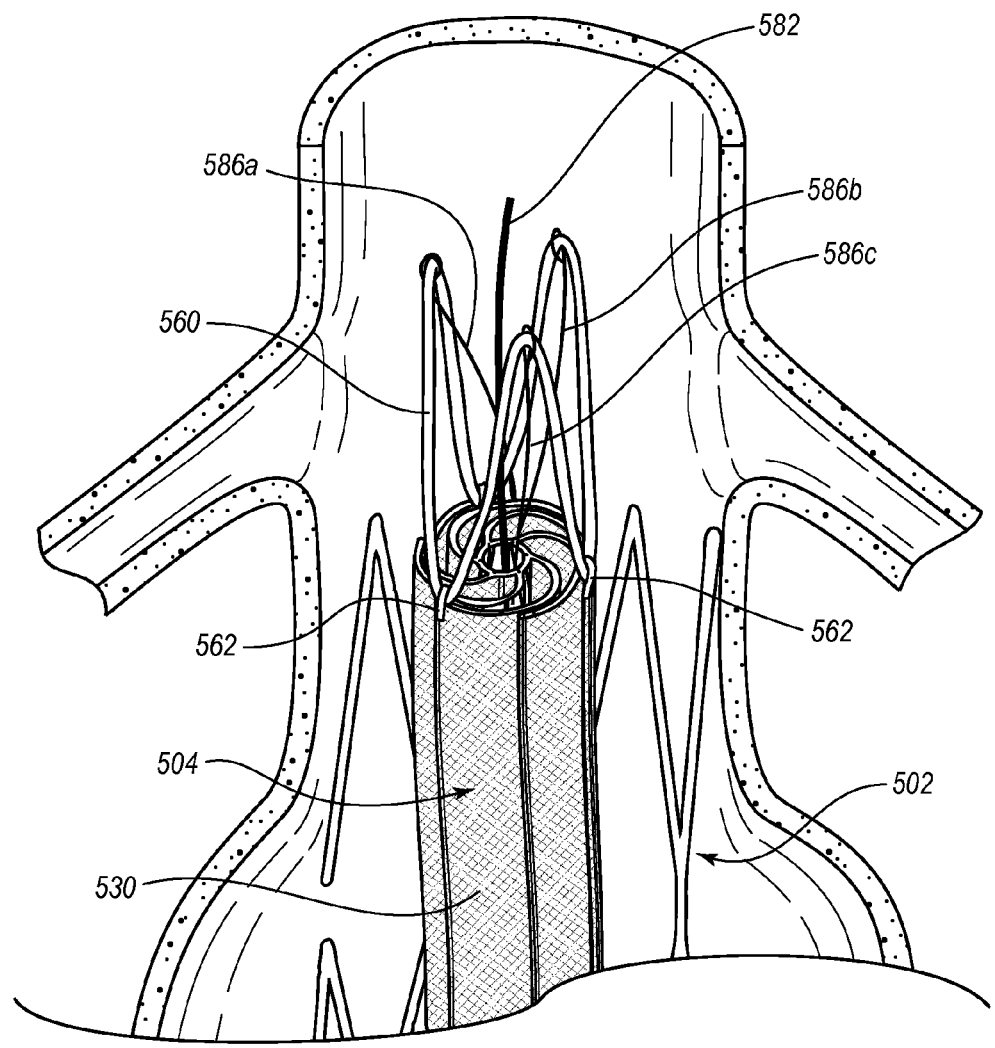
FIGS. 28-30 are partial cutaway perspective views of various stages of a procedure for implanting another embodiment of a stent graft assembly.
Figure 29:
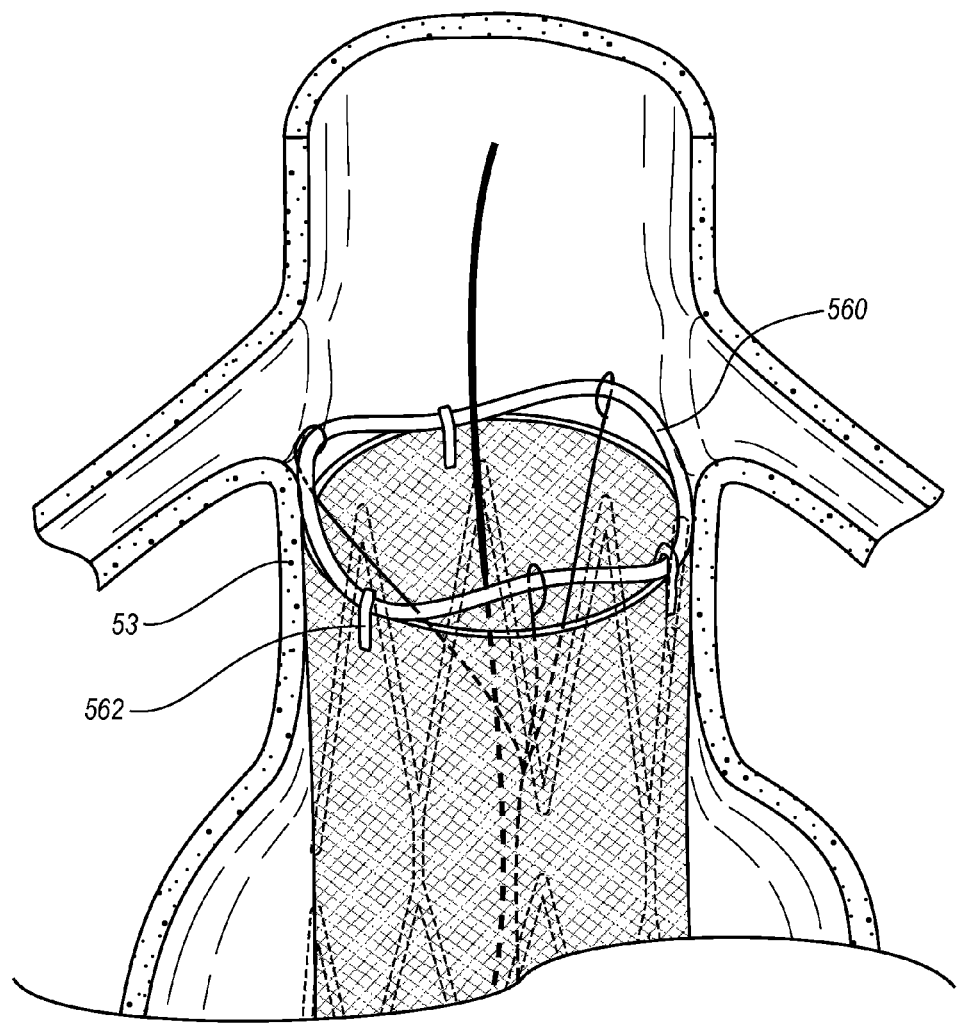
Figure 30:
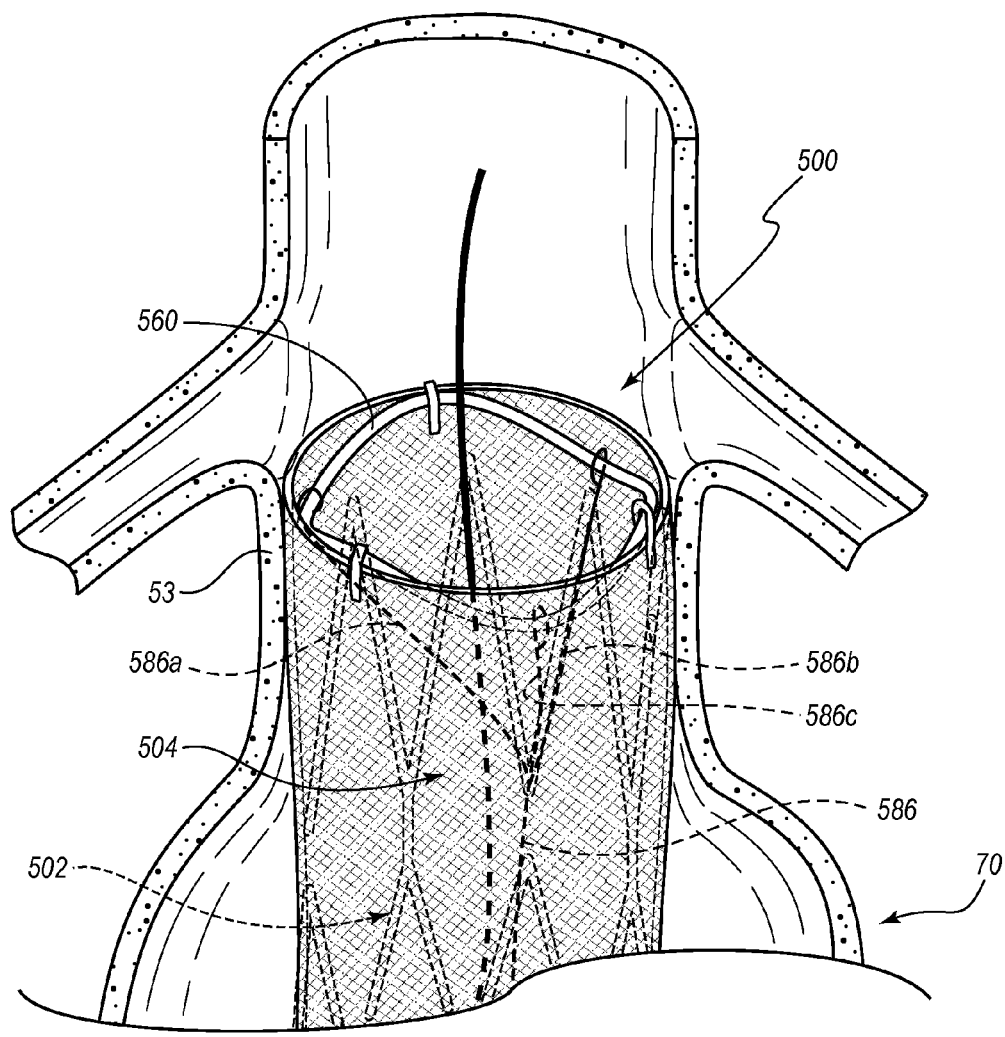

FIGS. 28-30 depict various stages of another illustrative method for endovascular placement of another embodiment of a stent graft assembly 500, which includes a stent 502 and a graft 504. At the stage shown in FIG. 28, each of the stent 502 and the graft 504 has separately been advanced over a guidewire 582 to the desired position with the vasculature 52, and the stent 502 has already been expanded into place (whether automatically, by balloon inflation, or otherwise). As can be appreciated from FIG. 28, the stent 502 may resemble the stents 202, 302, 402 described above. Moreover, at the stage shown in FIG. 28, the graft 504 is in a packaged or constricted state, but a sheath that surrounds the graft 504 so as to keep it in the packaged state is not shown for purposes of clarity.

The graft 504 comprises an anchor 560, which may also be referred to as a structural member, support elements, endo-structure, or stent, that is secured to an upper end of a graft wall 530 via a plurality of connectors 562, which may comprise any suitable material. For example, in some embodiments, the connectors 562 comprise a biocompatible metal, whereas in other embodiments, the connectors 562 may comprise sutures. In some embodiments, the anchor 560 may be rotatable within the connectors 562. When in the packaged state, the anchor 560 does not overlap the graft 504. Accordingly, the non-overlapping region of the packaged graft 504 and anchor 560 can resemble the non-overlapping region of the packaged graft 104 and stent 102 discussed above with respect to FIG. 3.

In FIG. 28, the anchor 560 is shown in a constricted state in which it has been deformed to a low-profile orientation. The anchor 560 can be self-expanding. For example, in some embodiments, the anchor 560 comprises a shape-memory material which, in further embodiments, may be configured to transition to a remembered orientation when heated within the patient. A positioning line 586 can be coupled to the anchor 560. In the illustrated embodiment, the positioning line 586 includes multiple segments 586a, 586b, 586c that are connected to different areas of the anchor 560. The multiple segments 586a, 586b, 586c can aid in distributing the force from the positioning line 586 so as to prevent skewing of the anchor 560 as it is transitioned from its original expanded state (FIG. 29) to an inverted state (FIG. 30).

The anchor 560 can transition naturally from the constricted orientation shown in FIG. 28 to the expanded orientation shown in FIG. 29. Portions of the expanded anchor 560 can contact the vessel wall 53 in this expanded state. The positioning line 586 can be used to draw the anchor 560 into an interior of the graft 504 to the position shown in FIG. 30. The anchor 560 may be said to be inverted, rotated, or reoriented into the graft 504. The anchor 560 can press outwardly on the graft 560 and may assist in forming a fluid-tight seal between the graft 504 and the vessel wall 53. The anchor 560 can be said to overlap an upper end of the graft 504.

In certain embodiments, the graft 504 can be expanded without use of a balloon, and may be considered as self-expanding. For example, in the illustrated embodiment, once the upper end of the graft 504 has been opened via the expanded anchor 560, blood flowing into the open end of the graft 504 may cause remaining portions thereof to expand.

As can be seen in FIG. 30, when the stent graft assembly 500 is in its final orientation, the stent 502 and the graft 504 are not directly connected to each other in the illustrated embodiment. In particular, the graft 504 engages the vessel wall 53 at a position that is above the upper end of the stent 502, and the stent 502 engages a separate portion of the vessel wall 53. Moreover, no portion of the stent 502 pierces through the graft 504, nor is the stent 502 connected to the graft 504 via any other form of connector. However, the stent 502 and the graft 504 are nevertheless coupled with each other. For example, the graft 504 presses outwardly against the stent 502 and is thereby restrained from further expansion, particularly in the region of the abdominal aortic aneurysm 70. The stent 502 thus provides supporting structure to the graft 504.

In other embodiments, the stent 502 and the graft 504 can be directly connected to each other in situ in any suitable manner, such as any of the connection mechanisms described herein. Other or further suitable fastening mechanisms that may be used include, for example, hooks, barbs, adhesives, hook and loop fasteners, locking interfaces, magnets, etc.

In some embodiments, the stent graft assembly 500 may not include the stent 502. For example, in some embodiments, the graft assembly 500 can include the graft 504 and the anchor 560 at an upper end thereof. The graft 504 can resemble the graft 104 described above, in that it is not encompassed by a stent in the region of the aneurysm 70. The graft 504 can be configured to channel blood through a lumen thereof substantially without expanding radially outwardly beyond a natural or predetermined size, and thus may reduce pressure on the vessel wall 53 in the region of the aneurysm 70. The anchor 560, which can also be referred to as a stent, can function similarly to the stent 102 described above in certain respects. For example, like the stent 102, the anchor 560 can be automatically deployed so as to bring the upper end of the graft 504 into contact and/or close proximity to the vessel wall 53. Inverting or otherwise drawing the anchor 560 into the graft 504 can further secure the graft 504 to the vessel wall 53.

Figure 32:
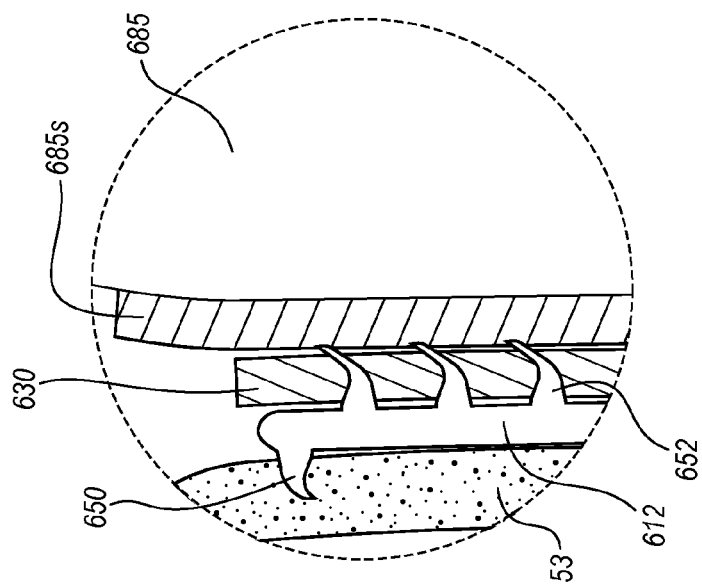
FIG. 32 is an enlarged partial cross-sectional view taken along the view line 32 in FIG. 31.
Figure 31:
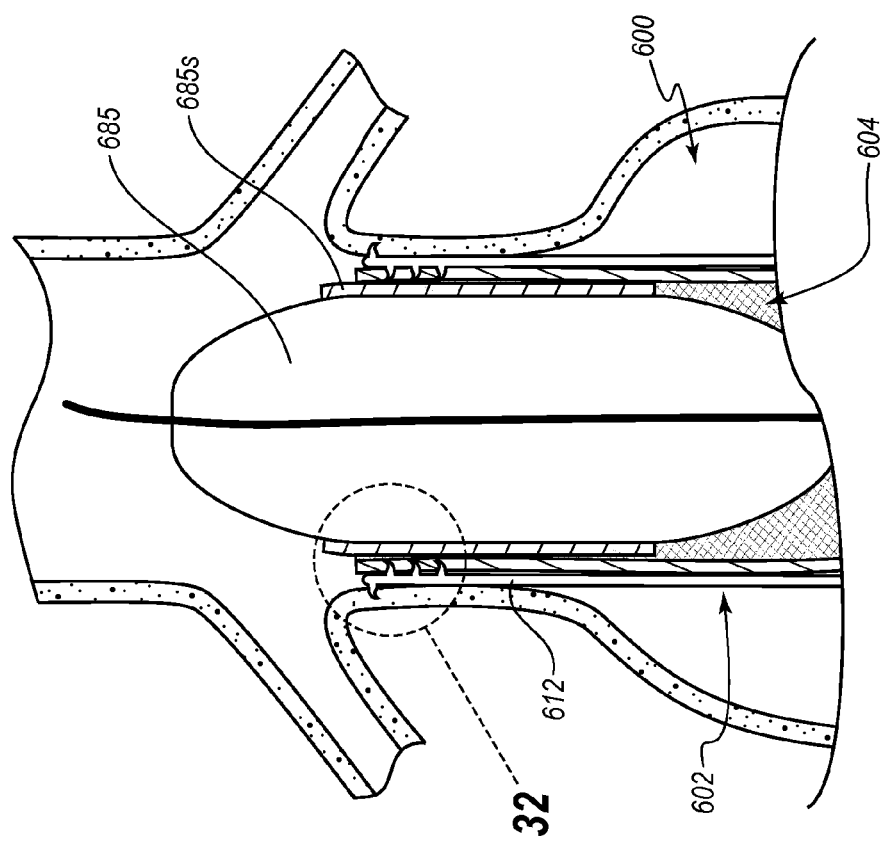
FIG. 31 is a partial cross-sectional view of a stage of an illustrative procedure for implanting another embodiment of a stent graft assembly.
Figure 33:
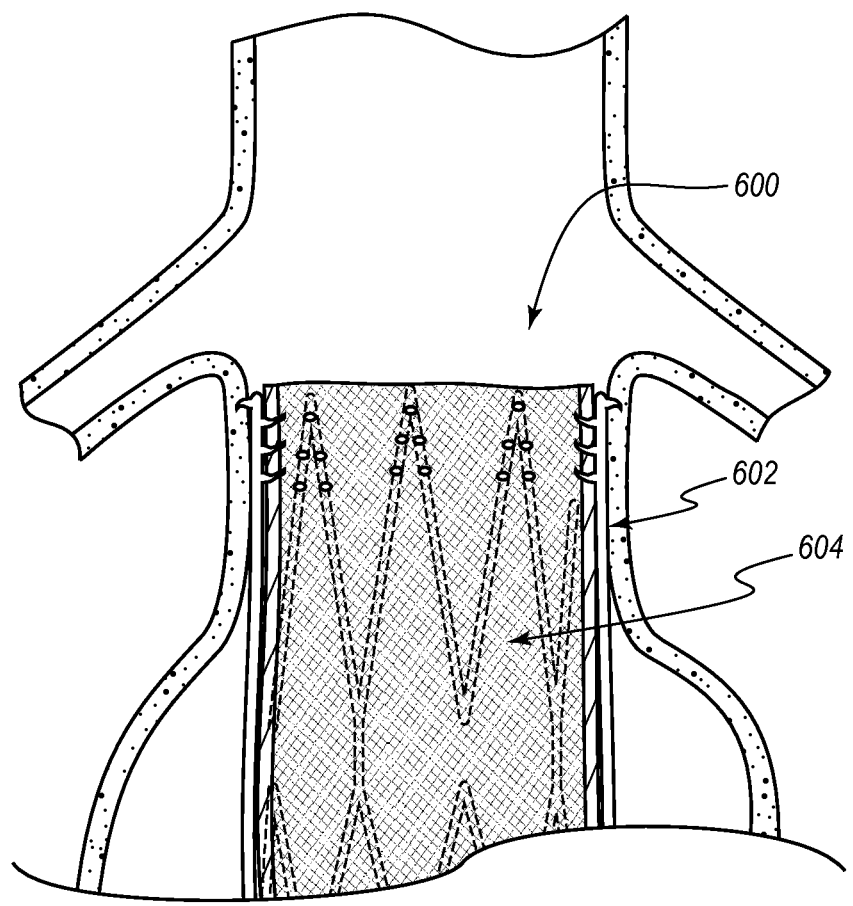
FIG. 33 is a partial cross-sectional view of another stage of the procedure of FIG. 31.

FIGS. 31-33 depict various stages of another illustrative method for endovascular placement of another embodiment of a stent graft assembly 600, which includes a stent 602 and a graft 604. The stent 602 includes links 612 that have outwardly projecting hooks 650 and inwardly projecting hooks 652. The outwardly projecting hooks 650 can be embedded within the vessel wall 53 in a manner similar to the hooks 350 discussed above, although an expansion balloon 685 may be used to assist with the embedding process. Moreover, the inwardly projecting hooks 652 can be forced through a wall 630 of the graft 604 by the expansion balloon 685. In the illustrated embodiment, the expansion balloon 685 includes a shielding layer 685s, such as a sheath, that protects the balloon 685 from punctures, tears, or ruptures from the inwardly projecting hooks 652. In other embodiments, the balloon 685 may be formed of a material that is itself resistant to such punctures, tears, or ruptures. As shown in FIG. 33, connections between the stent 602 and the graft 604 can extend about a periphery of an upper end of the assembly 600.

FIGS. 34-37 depict various stages of another illustrative method for endovascular placement of another embodiment of a stent graft assembly 700, which includes a stent 702 and a graft 704. The assembly 700 and placement method are particularly similar to the assembly 600 and the illustrative method just discussed. In particular, the stent 702 includes links 712 that have outwardly projecting hooks 750 and inwardly projecting hooks 752. The outwardly projecting hooks 750 can be embedded within the vessel wall 53, and the inwardly projecting hooks 752 can be forced through a wall 730 of the graft 704 by an expansion balloon 785 that includes a shielding layer 785s.

The stent 702 further includes one or more constraints 754, which are similar to the constraints 454 discussed above. In particular, the constraints 754 permit an upper end of the stent 702 to expand somewhat from its original constricted orientation, but prevent the upper end of the stent 702 from fully expanding into contact with the vessel wall 53.

Figure 34:
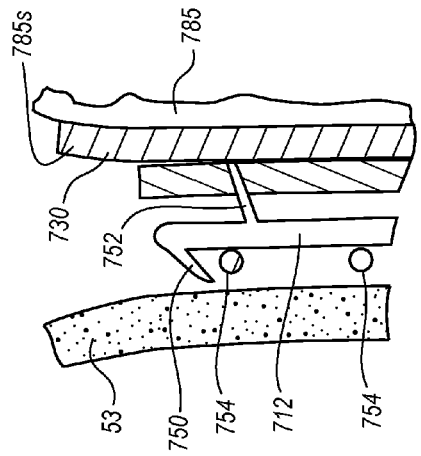
FIGS. 34-37 are partial cross-sectional views of various stages of an illustrative procedure for implanting another embodiment of a stent graft assembly.

FIG. 34 illustrates a stage of the procedure prior to expansion of the wall 730 of the graft 704. As can be seen, the hook 752 is substantially straight at this stage.

Figure 35:
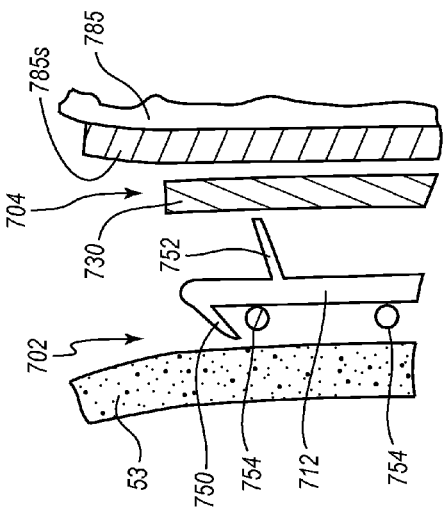

FIG. 35 illustrates a stage of the procedure in which the balloon 785 has forced the wall 730 of the graft 704 outwardly such that a portion of the hook 752 has pierced through the wall 730 and has come into contact with the shielding layer 785s. In order to arrive at this stage, the constraints 754 oppose the outward force provided by the balloon 785 to facilitate puncturing of the wall 730 by the hook 752.

Figure 36:
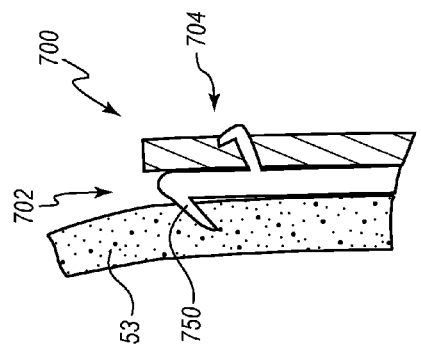

FIG. 36 illustrates that as the balloon 785 continues to expand outwardly, the constraints 754 can continue to oppose the outward force provided by the balloon 785. The opposing forces of the balloon 785 and the constraints 754 can cause the hook 752 to bend so as to more securely grip the wall 730 of the graft 704. The constraints 754 can prevent damage to the vessel wall 53 that might otherwise result if the wall 53 were to provide the opposing forces.

Figure 37:
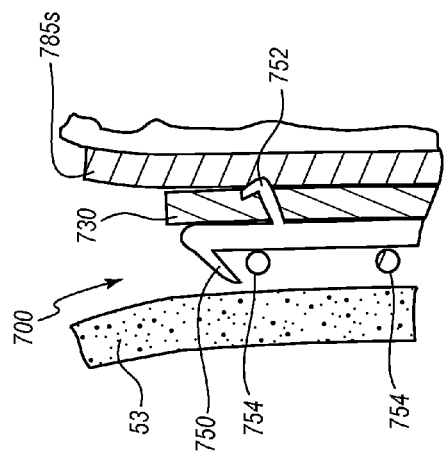

As shown in FIG. 37, after a secure connection has been formed between the stent 702 and the graft 704, the constraints 754 can be removed and the balloon 785 can expand further to embed the outwardly directed hook 750 into the vessel wall 53. In some embodiments, forces supplies by the balloon 785 are sufficient to remove the constraints 754, whereas in other embodiments, the constraints 754 can be removed by a separate device.

Figure 38:
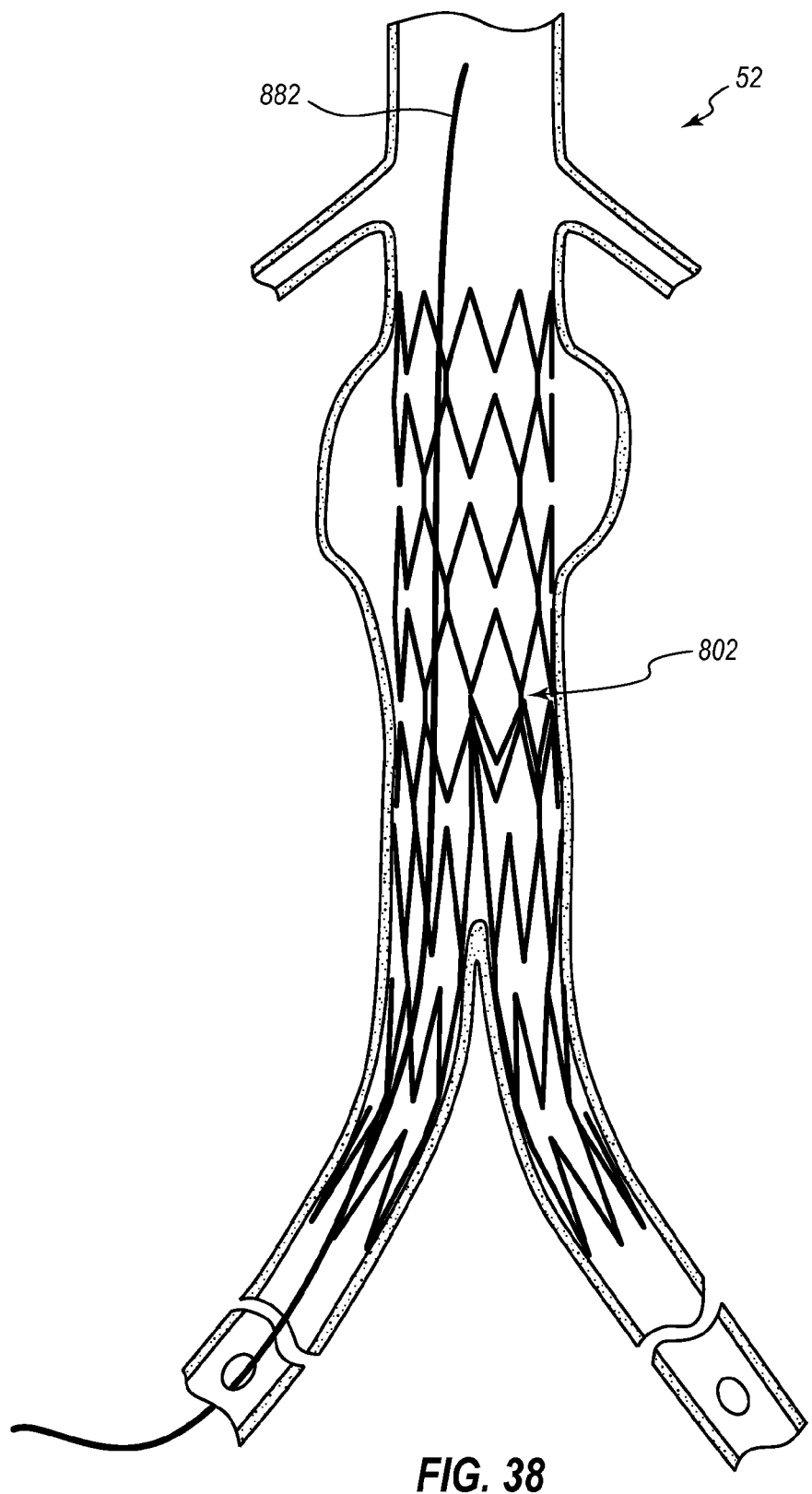
FIGS. 38-41 are cross-sectional views of various stages of an illustrative procedure for implanting another embodiment of a stent graft assembly.

FIGS. 38-41 depict various stages of another illustrative method for endovascular placement of another embodiment of a stent graft assembly 800, which includes a stent 802 and a graft 804. As shown in FIG. 38, the stent 802 can be positioned as desired within the vasculature 52 of the patient 50 and can be expanded. A guidewire 882 may be used in placing the stent 802. Any suitable techniques may be used in placing the stent 802, such as those described above with respect to the stents 202, 302.

Figure 39:
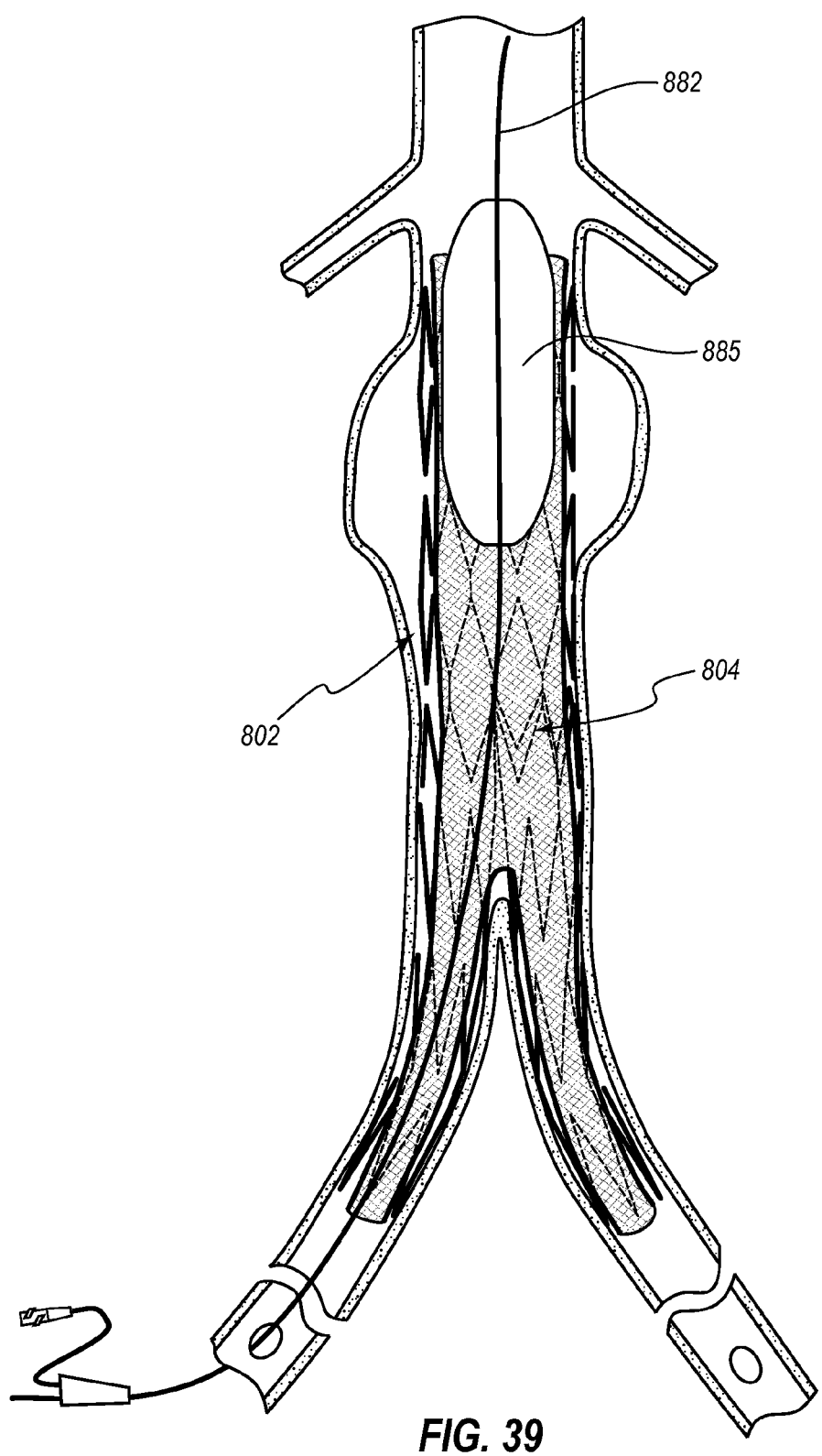

As shown in FIG. 39, the graft 804 can be separately placed within the vasculature 52 and advanced into the graft 804. The graft 804 may be expanded by a balloon 885. The graft 804 may be positioned within the stent 802 and expanded using techniques such as those discussed above with respect to the graft 304.

Figure 40:
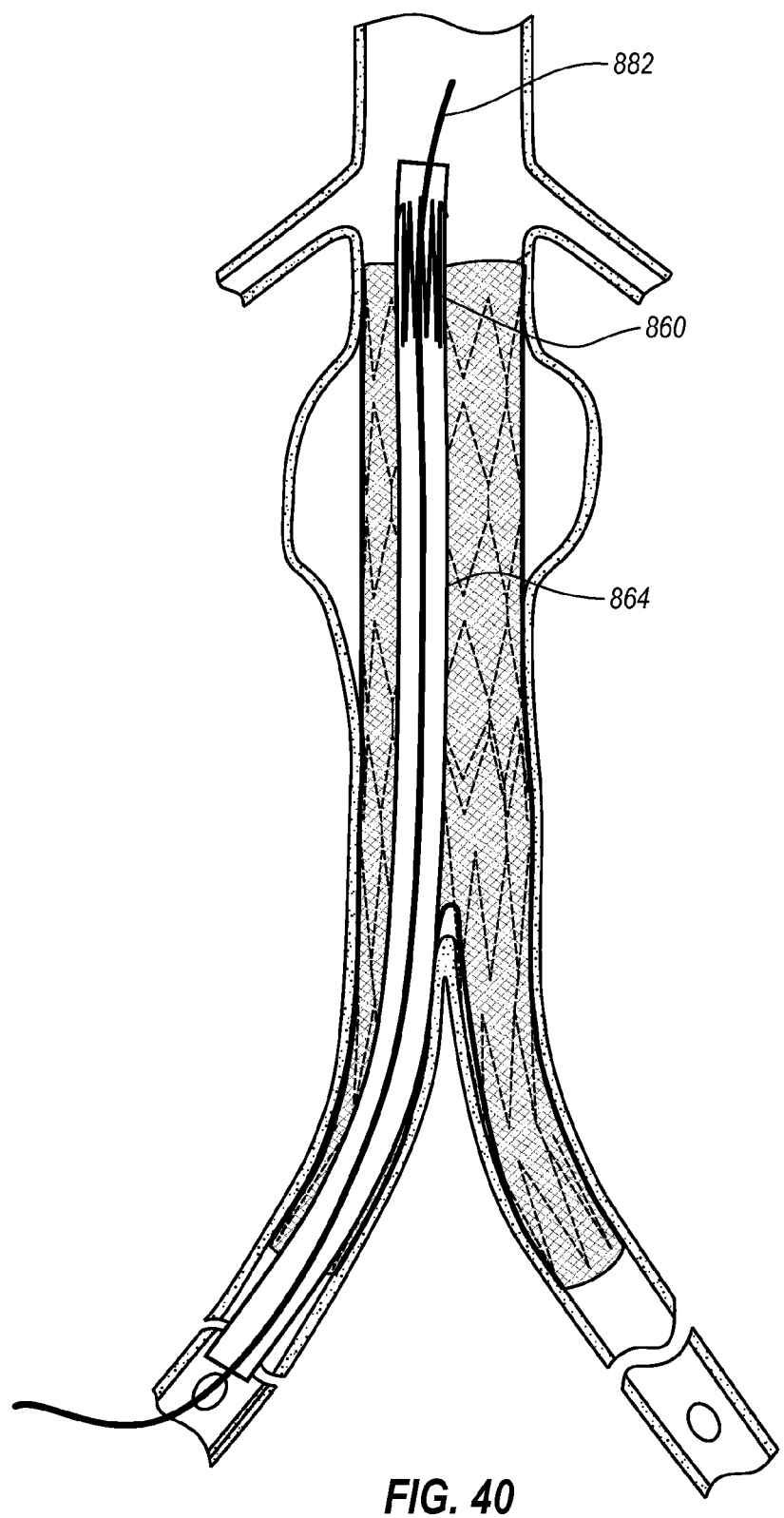

As shown in FIG. 40, after placement of the graft 804 and expansion thereof, an anchor 860, which may also be referred to as a stent, can be advanced into an interior of the graft 804. In the illustrated embodiment, the anchor 860 is originally retained in a constricted orientation via a sheath 864 and is advanced into place over the guidewire 882. The sheath 860 can be removed so as to permit the anchor 860 to expand.

Figure 41:
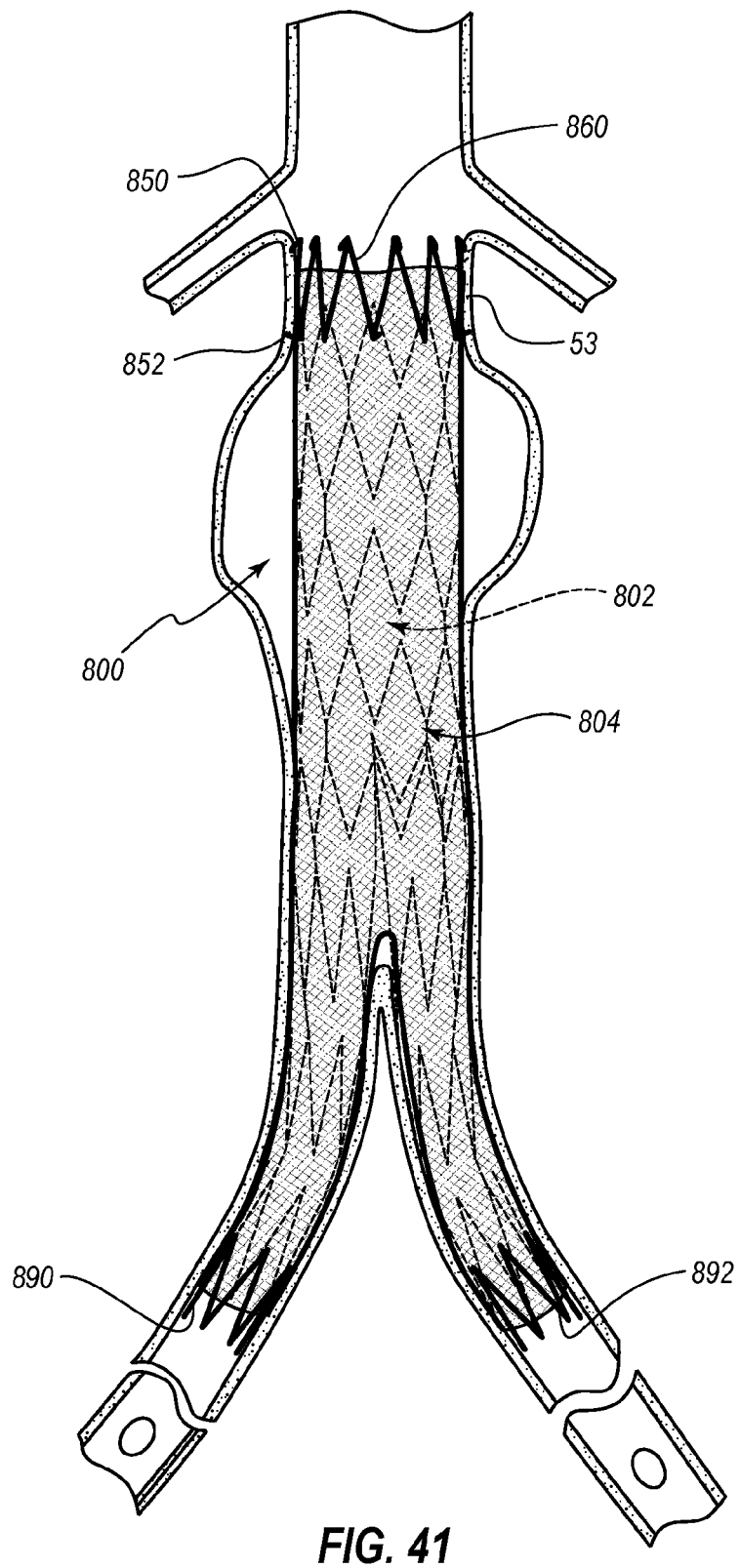

FIG. 41 illustrates the final configuration of the assembly 800, with the self-expanding anchor 860 in place. In some embodiments, the anchor 860 includes outwardly projecting hooks 850 that embed within the vessel wall 53 and outwardly projecting hooks 852 that extend through the graft 804 and embed within the vessel wall 53. Additional anchors 890, 892 are also provided at the bottom ends of the graft 804.

FIGS. 42A, 42B and 43 depict various stages of another illustrative method for endovascular placement of another embodiment of a stent graft assembly 900, which includes a stent 902 and a graft 904. The original states of the stent 902 and the graft 904 can resemble those of the stent 802 and the graft 804 shown in FIGS. 38 and 39. However, rather than using an anchor 860 to secure the graft 904 to the vessel wall 53 and/or to the stent 902, a series of sutures are used.

FIGS. 42A and 42B provide two different views of the same stage of the method, and illustrate a suturing device 908 that includes a curved needle 909. The needle 909 can be configured to pass through a wall 930 of the graft 904, through a portion of the vessel wall 53, around a link 912 of the stent 902, and back through the wall 930 of the graft 904. Any other suitable variety of suturing device may be used.

FIG. 43 illustrates a finished suture 955. The suture 955 extends through the wall 930 of the graft 904, through a portion of the vessel wall 53, around the link 912 of the stent 902, and back through the wall 930 of the graft 904. As with other connection mechanism discussed herein, the suturing the graft 904 to the stent 902 and or the vessel wall 902 can assist in achieving a substantially fluid-tight seal between the assembly 900 and the vessel wall 53.

Figure 44C:
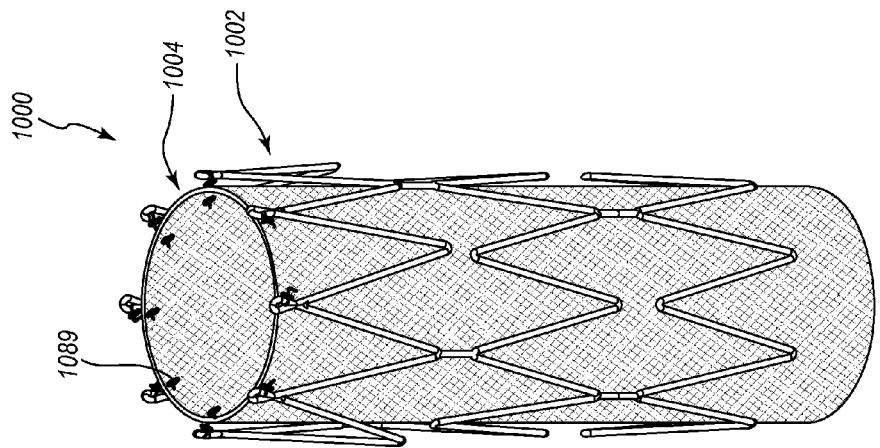
FIGS. 44A-44C are perspective views of various stages of an illustrative procedure for implanting another embodiment of a stent graft assembly.
Figure 44B:
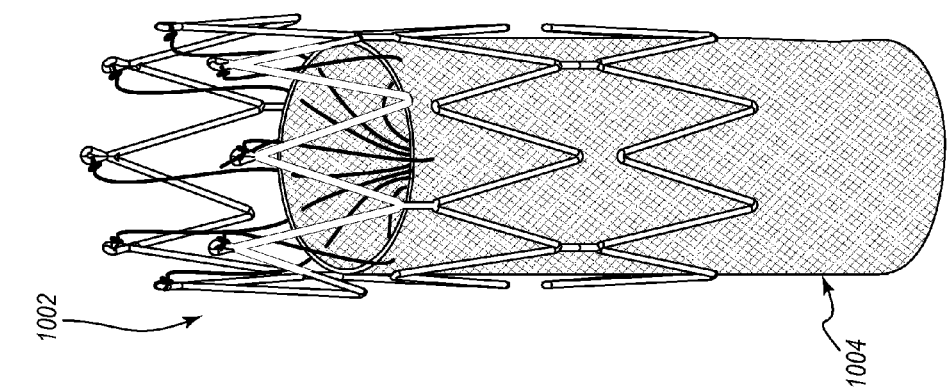
Figure 44A:
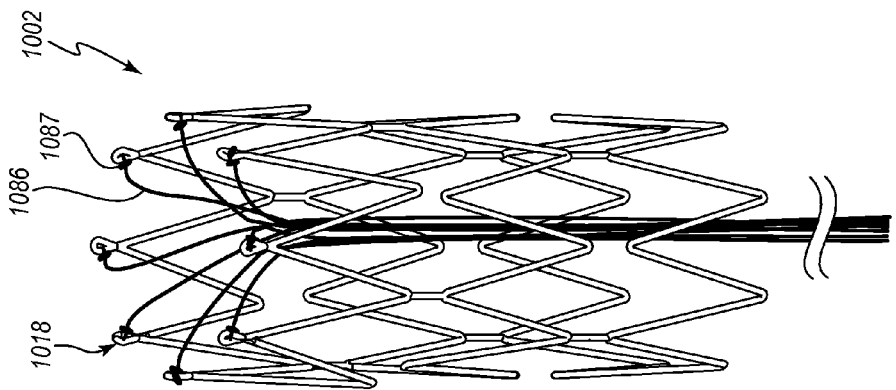

FIGS. 44A-44C depict various stages of another illustrative method for endovascular placement of another embodiment of a stent graft assembly 1000, which includes a stent 1002 and a graft 1004. When the stent 1002 is in the packaged state, it is attached to one or more positioning lines 1086. In particular, upper ends of the stent 1002 define apertures 1018 through which upper ends of the positioning lines 1086 pass, in the illustrated embodiment. The upper ends of the positioning lines 1086 are tied to the stent 1002 so as to define plurality of secure connections 1087. One example of a device that may be used to form or secure the connections 1089 is a surgical knot pusher such as that disclosed in U.S. Patent Application Publication No. 2005/0033325, the relevant disclosure of which is hereby incorporated by reference herein.

When the graft 1004 is in the packaged state, it is coupled with the positioning lines 1086. Specifically, the positioning lines 1086 pass through openings in the graft 1004. The stent 1002 and the graft 1004 may be packaged together (e.g., in the same sheath), or they may be packaged separately (e.g., in separate sheaths) such that the positioning lines 1086 extend between the stent and graft packages. In some embodiments, the stent 1002 and the graft 1004 are non-overlapping when in the packaged state.

As shown in FIG. 44A, the stent 1002 may be expanded into contact with the vessel wall 53 (which is not shown in FIG. 44A for purposes of clarity) in any suitable manner. As shown in FIG. 44B, the graft 1004 can be advanced over the positioning lines 1086 toward the upper end of the stent 1002. For example, the positioning lines 1086 may be held at a position that is external position and maintained in a taut arrangement, and the graft 1004 can be urged toward the upper end of the stent 1002. As shown in FIG. 44C, the graft 1004 can be secured in position via an additional set of connections 1089, which can comprise any suitable knot or other attachment feature. For example, a practitioner may tie off the positioning lines 1086 using suturing techniques, and may cut away the excess portions of the positioning lines 1086.

FIGS. 45A and 45B depict various stages of another illustrative method for endovascular placement of another embodiment of a stent graft assembly 1100, which includes a stent 1102 and a graft 1104, and which particularly resembles the graft assembly 1000. When the stent 1102 and the graft 1104 are in a packaged state, one or more positioning lines 1186 are attached to the graft 1104 via one or more connections 1187. The connections 1187 may comprise knots or other suitable connection features. The positioning lines 1186 pass through apertures 1118 at an upper end of the stent 1102 and pass back through an interior of the graft 1104. The stent 1102 and the graft 1104 may be in a non-overlapping packaged state. Once the stent 1102 has been expanded into position, the unattached ends of the positioning lines 1186 can be pulled so as to advance the graft 1104 through the stent 1102 toward the apertures 1118. Once the graft 1104 is in the desired position, the positioning lines 1186 can be secured to the stent 1102 via a plurality of additional connections 1189. For example, a practitioner may tie off the positioning lines 1186 using suturing techniques, and may cut away the excess portions of the positioning lines 1186.

FIGS. 46A-46B depict various stages of another illustrative method for endovascular placement of another embodiment of a stent graft assembly 1200, which includes a stent 1202 and a graft 1204, and which particularly resembles the graft assemblies 1000, 1100. When the stent 1202 and the graft 1204 are in a packaged state, one or more positioning lines 1286 are attached to the graft 1204 via one or more connections 1287. The positioning lines 1286 pass through apertures 1218 at an upper end of the stent 1202, pass through openings in the graft 1204, and pass downward through an interior of the graft 1204. The stent 1202 and the graft 1204 may be in a non-overlapping packaged state. Once the stent 1202 has been expanded into position, the unattached ends of the positioning lines 1286 can be pulled so as to advance the graft 1204 through the stent 1202 toward the apertures 1218. Once in the desired position, the positioning lines 1286 can be secured to the graft 1204 via a plurality of additional connections 1189. In some instances, the assembly 1200 can be particularly well-suited for avoiding tangles of the positioning lines 1286, particularly during advancement of the graft 1204 toward an upper end of the stent 1202.

In various embodiments, one or more of the stents 1002, 1102, 1202 can be relatively short, and may only overlap an upper portion of the grafts 1004, 1104, 1204 when the grafts have been moved to their final, implanted orientation. For example, in some embodiments, the stents 1002, 1102, 1202 may not provide an external support structure along a full longitudinal length of the grafts 1004, 1104, 1204, or a significant portion thereof, as do certain embodiments of the stents 202, 302, 402 relative to the grafts 204, 304, 404. Stated otherwise, in some embodiments, a downstream end of the implanted stents 1002, 1102, 1202 may be positioned upstream of the aneurysm 70. The grafts 1004, 1104, 1204 thus may function in a manner similar to the graft 104 described above. In other embodiments, the stents 1002, 1102, 1202 may have greater longitudinal length, and may function similarly to the stents 202, 302, 402 (e.g., providing a structural barrier that is positioned between the grafts 1004, 1104, 1204 and the vessel wall 53 in the region of the aneurysm 70).

Figure 47:
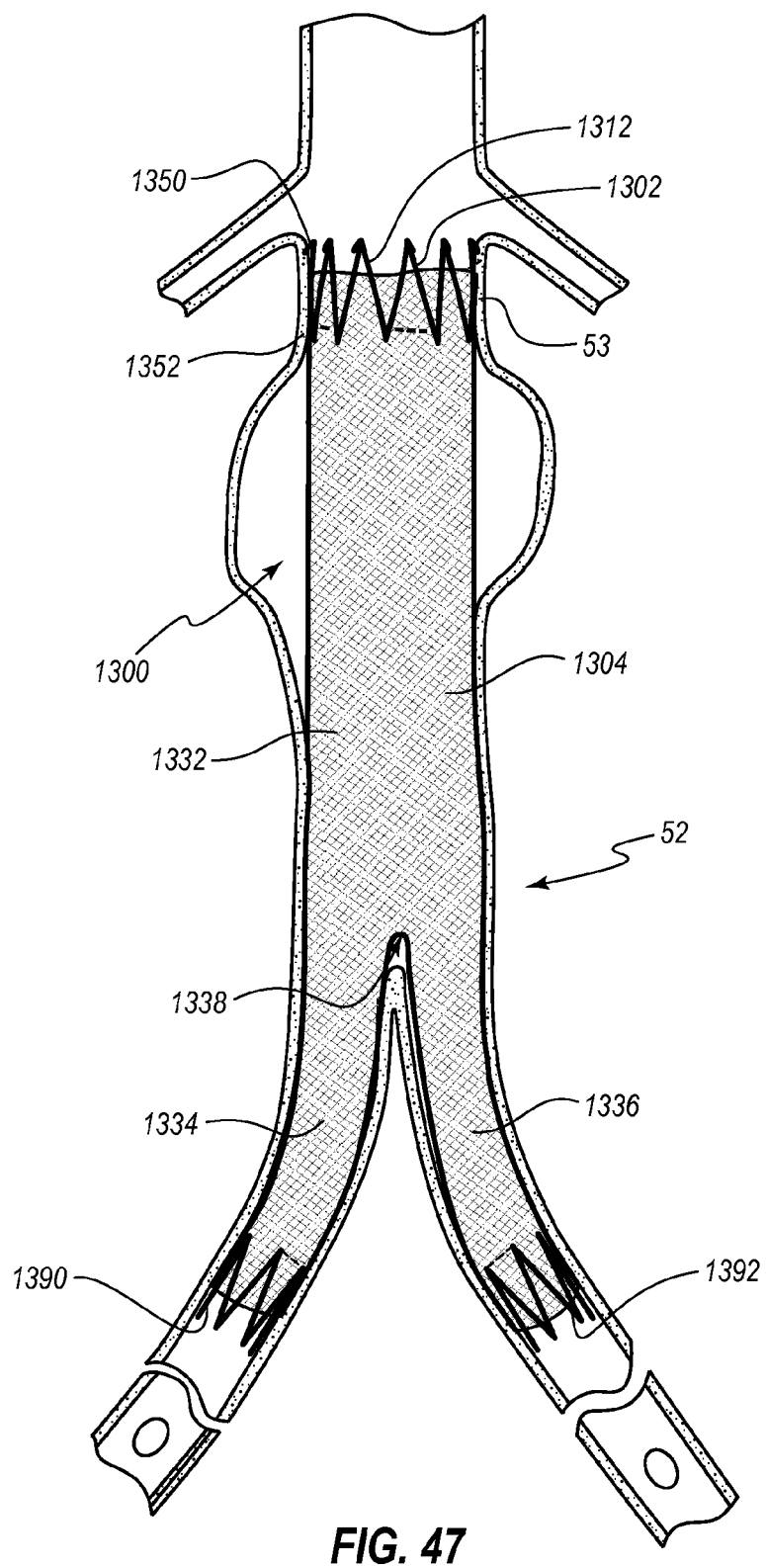
FIG. 47 is a cross-sectional view of another embodiment of a stent graft assembly that has been implanted within the vasculature of a patient.

FIG. 47 illustrates another embodiment of a stent graft assembly 1300, which includes a stent 1302 and a graft 1304, that has been implanted in the vasculature 52 of a patient. Any suitable processes for implanting the stent graft assembly 1300 are contemplated, including, for example, those discussed above with respect to at least a portion of any of the stent graft assemblies 100, 300, 400, 800. For example, in certain embodiments, the stent 1302 and the graft 1304 are attached to each other when in a packaged state, and can be retained in the packaged state via a sheath, such as the sheath 181 described above with respect to FIG. 3. The packaged stent 1302 and graft 1304 can be advanced over a guidewire into the desired position, and the sheath can then be withdrawn so as to permit the stent 1302 to automatically deploy, such as by returning to an uncompressed state and/or transitioning to a remembered state. In the illustrated embodiment, a lower portion of the stent 1302 is at an interior of the upper end of the graft 1304 when the stent graft assembly 1300 is in the deployed state. The stent 1302 presses outwardly on the graft 1304 and urges it against the vessel wall 53. As further discussed below, the stent 1302 and the graft 1304 can automatically move relative to each other during deployment to achieve this overlapping configuration. In some embodiments, the stent 1302 includes barbs 1350, which may resemble the barbs 105 discussed above.

In the illustrated embodiment, the graft 1304 includes a trunk region 1332 that splits into two branches 1334, 1336 at a bifurcation 1338. The branches 1334, 1336 can be deployed into neighboring arteries using any suitable endovascular placement technique, such as those discussed above. In the illustrated embodiment, anchors 1390, 1392 are separately placed at the bottom ends of the branches 1334, 1336. The anchors 1390, 1392, and the placement thereof, can resemble the anchors 290, 292. In other embodiments, the branch 1336 may be shortened, and a modular secondary assembly (such as the secondary assembly 170 discussed above) may instead be used with the graft 1304. In certain of such embodiments, the anchor 1390 may initially be attached to the branch 1334, such that the anchor 1390 overlaps a portion of the branch 1334 when the assembly 1300 is in the packaged state. In certain of such embodiments, the anchor 1390 may resemble the lower stent 103 discussed above.

FIGS. 48A-48C illustrate various stages of the deployment of the upper end of the stent graft assembly 1300. FIG. 48A depicts the stent graft assembly 1300 in the packaged state, although a sheath, which can be used to maintain the assembly in the packaged state, is not shown for purposes of clarity. The stent 1302 is in a compressed or compacted configuration in which adjacent branches 1312 thereof are closely approximated to each other. Adjacent pairs of the branches 1312 can be joined at nadirs 1341, which are positioned at the lower end of the stent 1302. Each nadir 1341 may define a loop, eyelet, or opening through which a portion of a suture 1340 or other suitable threading element may pass. In the illustrated embodiment, opposite ends of a suture 1340 are threaded through and tied to adjacent nadirs 1341. Other suitable arrangements are possible for attaching the sutures 1340 to the stent 1302. Each suture 1340 can extend through an upper portion of the graft 1304. The sutures 1340 can be pulled upwardly so as to cinch an upper end of the graft 1304 into the constricted or packaged configuration. As can be seen in FIG. 48A, as a result, the stent 1302 can be spaced from the graft 1304, such that the stent 1302 and the graft 1304 are non-overlapping in the packaged configuration.

As shown in FIG. 48B, as the stent 1302 expands, the stent 1302 can move longitudinally relative to the graft 1304. In the illustrated embodiment, a lower portion of the stent 1302 is drawn into an interior of the graft 1304 (or, it may be said that the graft 1304 is drawn upward about an exterior of the stent 1302). This automatic movement of the stent 1302 into an overlapping relationship relative to the graft 1304 can result from the extension of the sutures 1340 in a lateral direction. The sutures 1340 were elongated in a longitudinal direction in the packaged configuration, and only a small portion thereof extended laterally. However, due to expansion of the branches 1312 and movement of the nadirs 1340 away from each other, a greater portion of the sutures 1340 extends in the lateral direction, which reduces the portion of the sutures 1340 that extends longitudinally. Stated otherwise, as the graft 1304 moves from the cinched orientation to a more spread out orientation, the longitudinally extending portion of the sutures 1340 decreases, thereby moving the stent 1302 and the graft 1304 into an overlapping arrangement.

As shown in FIG. 48C, when the stent 1302 is fully expanded, a maximum overlapping distance $D_0$ is achieved. In certain embodiments, the sutures 1340 may extend substantially laterally in such arrangements, and may not extend in the longitudinal direction.

In the illustrated embodiment, the sutures 1340 are positioned at an exterior of the graft 1304, and the stent 1302 is drawn into an interior of the graft 1304. In other embodiments, the sutures 1340 may be positioned at the interior and/or the exterior of the graft 1304, and/or the stent 1302 may be drawn into a position at the exterior of the graft 1304.

As can be appreciated from the foregoing, the stent 1302 and the graft 1304 are in a non-overlapping configuration when the stent graft assembly 1300 is in the packaged state. The stent 1302 and the graft 1304 automatically transition to an overlapping state as the stent graft assembly 1300 is deployed. The terms overlapping and non-overlapping, as used herein, include interior/exterior relationships along a common longitudinal length. For example, a stent and graft can overlap one another where at least a portion of the stent is at the same longitudinal position as at least a portion of the graft, and where the stent is either at an interior or exterior of the graft at that longitudinal position.

As previously mentioned, while the drawings and written description have focused on illustrative devices, systems, and methods related to the repair of aortic aneurysms, it is to be understood that embodiments may be used in any other suitable context, such as contexts where stent grafts are commonly used. Moreover, it will be understood by those having skill in the art that changes may be made to the details of the above-described embodiments without departing from the underlying principles presented herein. For example, any suitable combination of various embodiments, or the features thereof, is contemplated.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the terms "about" or "approximately." For each such reference, it is to be understood that, in some embodiments, the value, feature, or characteristic may be specified without approximation. For example, where qualifiers such as "about," "substantially," and "generally" are used, these terms include within their scope the qualified words in the absence of their qualifiers. For example, where the term "substantially planar" is recited with respect to a feature, it is understood that in further embodiments, the feature can have a precisely planar orientation.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the preceding claims up to and including claim [x]," where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claim 1, 2, or 3, with these separate dependencies yielding three distinct embodiments; claim 5 can depend from any one of claim 1, 2, 3, or 4, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed in accordance with 35 U.S.C. §112 ¶ 6. Embodiments of the invention in which an exclusive property or privilege is claimed are defined as follows.

The invention claimed is:

1. A prosthetic assembly comprising:
   a graft defining a first opening, a second opening, and a third opening;
   a first stent attached to the graft at the first opening such that the first stent does not overlap the graft; and
   a second stent attached to the graft at the second opening;
      wherein the graft comprises a trunk and first and second branches that extend from the trunk at a bifurcation, wherein the first opening is at an end of the trunk, the second opening is at an end of the first branch, and the third opening is at an end of the second branch;
      wherein the second branch is shorter than the first branch such that the first branch comprises a first portion extending from the bifurcation to a location aligned with the end of the second branch and a second portion extending longitudinally beyond the end of the second branch and wherein there are no supporting structures along the first portion of the first branch and along the second branch, thus providing a non-supported first portion of the first branch and a non-supported second branch; and
      wherein the prosthetic assembly is configured such that, prior to, and during insertion into a patient, the non-supported second branch is fully extended, and the non-supported second branch does not overlap the attached second stent.

2. The prosthetic assembly of claim 1, further comprising a third stent that is configured to be coupled with the graft at the third opening.

3. The prosthetic assembly of claim 2, further comprising an auxiliary branch, wherein the third stent is coupled with a first end of the auxiliary branch, and wherein the third stent is configured to be coupled with the graft at the third opening after the graft has been positioned within a vasculature of a patient.

4. The prosthetic assembly of claim 3, further comprising a fourth stent coupled with a second end of the auxiliary branch.

5. A prosthetic assembly comprising:
a graft defining a first opening, a second opening, and a third opening;
a first stent attached to the graft at the first opening such that the first stent does not overlap the graft; and
a second stent attached to the graft at the second opening;
wherein the graft comprises a trunk and first and second branches that extend from the trunk at a bifurcation, wherein the first opening is at an end of the trunk, the second opening is at an end of the first branch, and the third opening is at an end of the second branch;
wherein the second branch is shorter than the first branch such that the first branch comprises a first portion extending from the bifurcation to a location aligned with the end of the second branch and a second portion extending longitudinally beyond the end of the second branch and wherein there are no supporting structures along the first portion of the first branch and along the second branch, thus providing a non-supported first portion of the first branch and a non-supported second branch; and
wherein the prosthetic assembly is configured such that, prior to, and during insertion into a patient, the non-supported second branch is fully extended, and the non-supported second branch is longitudinally spaced from the attached second stent.

6. The prosthetic assembly of claim 5, further comprising a third stent that is configured to be coupled with the graft at the third opening.

7. The prosthetic assembly of claim 6, further comprising an auxiliary branch, wherein the third stent is coupled with a first end of the auxiliary branch, and wherein the third stent is configured to be coupled with the graft at the third opening after the graft has been positioned within a vasculature of a patient.

8. The prosthetic assembly of claim 7, further comprising a fourth stent coupled with a second end of the auxiliary branch.

9. A prosthetic assembly comprising:
a graft in a constricted state, wherein the graft comprises a trunk and first and second branches that extend from the trunk at a bifurcation, the graft further comprising a first opening at an end of the trunk, a second opening at an end of the first branch, and a third opening at an end of the second branch;
a first stent in a constricted state, wherein the first stent is attached to the graft at the first opening such that the first stent does not overlap the graft;
a second stent in a constricted state, wherein the second stent is attached to the graft at the second opening; and
a sheath configured to encompass at least a portion of the graft, wherein the second branch is shorter than the first branch such that the first branch comprises a first portion extending from the bifurcation to a location aligned with the end of the second branch and a second portion extending longitudinally beyond the end of the second branch, and wherein there are no supporting structures along the first portion of the first branch and along the second branch; and
wherein the end of the second branch is longitudinally spaced from the second stent such that the second branch is fully extended and no portion of the second branch contacts the second stent.

10. The prosthetic assembly of claim 9, further comprising a third stent that is configured to be coupled with the graft at the third opening after the sheath has been removed.

11. The prosthetic assembly of claim 10, further comprising an auxiliary branch, wherein the third stent is coupled with a first end of the auxiliary branch.

12. The prosthetic assembly of claim 11, further comprising a fourth stent coupled with a second end of the auxiliary branch.

13. The prosthetic assembly of claim 9, wherein the sheath encompasses the graft, and wherein the first portion of the first branch is generally parallel to and coextensive with the second branch.

* * * * *